US007511009B2

(12) United States Patent
Tombran-Tink et al.

(10) Patent No.: US 7,511,009 B2
(45) Date of Patent: *Mar. 31, 2009

(54) RETINAL PIGMENTED EPITHELIUM DERIVED NEUROTROPHIC FACTOR

(75) Inventors: Joyce Tombran-Tink, Derwood, MD (US); Gerald J. Chader, Bethesda, MD (US); Sofia Patricia Becerra, Bethseda, MD (US); Ignacio R. Rodriguez, Rockville, MD (US); Fintan R. Steele, Washington, DC (US); Lincoln V. Johnson, Pasadena, CA (US)

(73) Assignee: The National Institutes of Health, Washington, DC (US)

( * ) Notice: Subject to any disclaimer, the term of this patent is extended or adjusted under 35 U.S.C. 154(b) by 992 days.

This patent is subject to a terminal disclaimer.

(21) Appl. No.: 10/216,373

(22) Filed: Aug. 9, 2002

(65) Prior Publication Data

US 2003/0096750 A1 May 22, 2003
US 2007/0281886 A9 Dec. 6, 2007

Related U.S. Application Data

(60) Division of application No. 08/520,373, filed on Aug. 29, 1995, now Pat. No. 6,451,763, which is a continuation of application No. 08/377,710, filed on Jan. 25, 1995, now abandoned, which is a continuation of application No. 08/279,979, filed on Jul. 25, 1994, now abandoned, and a continuation-in-part of application No. 07/952,796, filed on Sep. 24, 1992, now abandoned, which is a continuation-in-part of application No. 07/894,215, filed on Jun. 4, 1992, now abandoned.

(51) Int. Cl.
*A61K 38/00* (2006.01)
*A61K 38/02* (2006.01)
*A61K 38/18* (2006.01)

(52) U.S. Cl. .............................. 514/2; 514/12
(58) Field of Classification Search ....................... None
See application file for complete search history.

(56) References Cited

U.S. PATENT DOCUMENTS

| | | | |
|---|---|---|---|
| 1,700,691 | A | 1/1929 | Stuart |
| 4,477,435 | A | 10/1984 | Courtois et al. |
| 4,534,967 | A | 8/1985 | Jacobson et al. |
| 4,670,257 | A | 6/1987 | Guedon born Saglier et al. |
| 4,770,877 | A | 9/1988 | Jacobson |
| 4,818,542 | A | 4/1989 | DeLuca et al. |
| 4,996,159 | A | 2/1991 | Glaser |
| 5,244,902 | A | 9/1993 | Sharpe et al. |
| 5,840,686 | A | 11/1998 | Chader et al. |
| 6,319,781 | B1 | 11/2001 | Lee et al. |
| 6,451,763 | B1 * | 9/2002 | Tombran-Tink et al. ....... 514/12 |
| 6,457,563 | B1 | 10/2002 | Ahlbom et al. |

FOREIGN PATENT DOCUMENTS

| | | |
|---|---|---|
| EP | 0412554 B1 | 11/1994 |
| EP | 0662087 B1 | 10/2003 |
| EP | 1415994 A1 | 5/2004 |
| WO | WO 91/03568 A1 | 3/1991 |
| WO | WO9324529 | * 12/1993 |
| WO | WO 95/33480 | * 12/1995 |

OTHER PUBLICATIONS

Wells, 1990, Biochemistry 29:8509-8517.*
Ngo et al., 1994, The Protein Folding Problem and Tertiary Structure Prediction, pp. 491-495.*
Bork, 2000, Genome Research 10:398-400.*
Skolnick et al., 2000, Trends in Biotech. 18(1):34-39, especially p. 36 at Box 2.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Tombran-Tink and Barnstable. Trends Mol Med.; 2003: 9: 244-250.*
Dawson et al, Science. 1999: 285-245-248.*
Maik-Rachline et al. Blood; 2005: 105: 670-678.*
Ellsworth, RM. Trans Am Opthalmol Soc. 1969; 67: 462-534.*
Fax containing ATCC Certificate of Deposit; Dec. 13, 2000; 2 pages total.*
Tombran-Tink et al., "Localization of the Gene for Pigment Epithelium-Derived Factor (PEDF) to Chromosome 17p13.1 and Expression in Cultured Human Retinoblastoma Cells". *Genomics.* 19:266-272, 1994.
Zou, Z., et al., "Maspin, a Serpin with Turmor-Suppressing Activity in Human Mammary Epithelial Cells," *Science*, 263:526-530, 1994.
Becerra, S.P., et al., "Structure-Function Studies of Pigment Epithelium Derived Factor (PEDF)", *FASEB Journal (Abstract No. 192)*, vol. 7, Apr. 20, 1993.
Pignolo, R.J., et al., Senescent WI-38 Cells Fail to Express *EPC-1*, a Gene induced in Young Cells Upon Entry Into the $G_o$ State. *The Journal of Biological Chemistry* , 268:8949-8957, 1993.
Tombran-Tink, et al., "Neurotrophic Activity of Interphotoreceptor Matrix on Human Y79 Retinoblastoma Cells," *The Journal of Comparative Neurology*, 307 (1992) 175-186.
Genbank Data Bank, Accession No. M76979 (1991).

(Continued)

*Primary Examiner*—Elizabeth C. Kemmerer
*Assistant Examiner*—Christina Borgeest
(74) *Attorney, Agent, or Firm*—Woodcock Washburn LLP

(57) ABSTRACT

The present invention relates to a purified retinal pigmented epithelium derived neurotrophic factor composition and a method for purifying such a retinal pigmented epithelium neurotrophic factor. The present invention also relates to a recombinant DNA molecule comprising a gene encoding a retinal pigmented epithelium derived neurotrophic factor having the DNA sequence or the amino acid sequence in SEQ ID NO:1 and to an organism transformed with the recombinant DNA molecule.

In addition, the present invention relates to a method of treating tumors, ocular diseases, nerve injuries, and conditions resulting from the activity of serine proteases, which comprises administering PEDF.

13 Claims, No Drawings

OTHER PUBLICATIONS

Becerra, et al., "Recombinant Human Fetal Retinal Pigment Epithelium-Derived Factor (PEDF)," *Investigative Ophthalmology & Visual Science*, 33, 823 (1992) Abstract.

Tombran-Tink, et al., "RPE-54—A Unique RPE Product with Neuronal Differentiating Activity," *Investigative Ophthalmology & Visual Science*, 29:414, 1989.

Tombran-Tink, et al., "Neuronal Differentiation of Retinoblastoma Cells Induced by Medium Conditioned by Human RPE Cells," *Investigative Ophthalmology & Visual Science*, 30:1700-1707, 1989.

Tombran-Tink, et al., "PEDF: A Pigment Epithelium-derived Factor with Potent Neuronal Differentiative Activity," *Experimental Eye Research*, 53:411-414, 1991.

Tombran-Tink, et al., "Molecular Cloning and Chromosomal Localization of the Gene for Human Pigment Epithelium-Derived Factor (PEDF)," *Investigative Ophthalmology & Visual Science*, 33(4):828. 1992.

Becerra, et al., "A Novel Retinal Neurotrophic Factor (PEDF): A Serine Protease Inhibitor?", presented at NIH Research Festival 1992 (Sep. 21-25, 1992).

Tombran-Tink et al., "Partial Amino Acid Sequence and Neurotrophic Activity of a Novel Human Pigment Epithelium-Derived Factor (PEDF)," *Investigative Ophthalmology & Visual Science*, 32, 765 (1991) (Abstract.

Hewitt et al., "Photoreceptor Survival-promoting Activity in Interphotoreceptor Matrix Preparations: Characterization and Partial Purifications," *Experimental Eye Research*, 50 77-99 (1990).

Sheedlo et al., "Effects of a Putative RPE-Cell Trophic Factor(s) on Photoreceptor Cell Survival in RCS Dystrophic Rats," Abstract #2916-14 (p. 595).

Campochiaro et al., "Retinal Pigment Epithelial Cells Produce PDGF-like Proteins and Secrete Them Into Their Media," *Abstract* #13 (p. 305).

Elner, et al., "Neutrophil Chemotactic Factor (IL-8) Gene Expression by Cytokine Treated Human Retinal Pigment Epithelial (RPE) Cells," Abstract #367-85 (p. 74).

Connor et al., "RPE Cells Synthesize and Release Transforming Growth Factor-Beta, A Modulator of Endothelial Cell Growth and Wound Healing," Abstract #26 (p. 307).

Campochiaro et al., "A Retina-Derived Stimulator(s) of Retinal Pigment Epithelial Cell and Astrocyte Proliferation," *Exp. Eye Res.*, (1986) 43 449-457.

Liu et al., "Photoreceptor Cell Survival and Differentiation Stimulated by Rat Retinal Pigment Epithelium Conditioned Medium in Tissue Cultures," Abstract #368-86, NIH/NEI F 32 EY06172-01 (S.J.P.) (p. 75).

Lindsey, et al., "Photoreceptor Survival-Promoting Activity in Interphotoreceptor Matrix Preparations: Characterization and Partial Purification," Abstract #50 (p. 242).

Allen et al., "Differentation of Photoreceptor Cells in Cultures of Embryonic Chick Retina Supplemented with Pigment Epithelium Conditioned Medium," Abstract #51 (p. 242).

Wilcox, David K., "Extracellular Release of Acid Hydrolases from Cultured Retinal Pigmented Epithelium," *Investigavtive Ophthalmology Visual Science*, 28, 76-82 (1987).

Bryan et al., "A Retinal Pigment Epithelial Cell-Derived Growth Factor(s)." *Arch. Ophthalmol.*, 104, 422-425 (1986).

Elner et al., "Rapid Communication: Neutrophil Chemotactic Factor (IL-8) Gene Expression by Cytokine-treated Retinal Pigment Epithelial Cells," *Am. J. Path.*, 136, 745-750 (1990).

Pittack et al., *Development* 113:577-588 (1991).

Park, et al., "Induction of Retinal Regeneration *in vivo* by Growth Factors", *Developmental Biology*, 148, 322-333 (1991).

Allen et al., "Differentiation of Photoreceptor Cells in Culture of Embryonic Chick Retina Supplemented with Pigment Epithelium Conditioned Medium," Abstract #51, p. 242.

Massry et al., *Soc. Neuro* USC1, Abstract 15, 1330 (1989).

Li et al., *Invest. Ophthalmol. Vis. Sci.*, 32, 770 (1991).

Rotenberg et al., *Invest. Ophthalmol. Vis. Sci.* 32, 770 (1991).

Pignolo, M.O. et al., *Gerontologist* 32:123 (1992): Ann. Mtg. Gerontologist Society of America Nov. 18-22, 1992.

Doggett et al., *Mechanisms of Aging and Development*, 65 (1992) 239-255, Elseivier Scientific Publisher Ireland Ltd.

Cristofalo et al., *Experimental Gerontology*, vol. 27, pp. 429-432 (1992).

Klaidman et al., "Effects of Medium Conditioned by Retinal Pigmented Epithelial Cells on Neurotransmitter Phenotype in Retinoblastoma Cells," *Cancer Letters*, 68 (1993), 207-213.

Tombran-Tink et al., "Modulation of Catecholamines in Retinoblastoma Cells Induced to Differentiate by Retinal Pigmented Epithelial Cell Conditioned Medium." *Society for Neuroscience Abstracts*, vol. 15 (1989), p. 1330.

Tombran-Tink et al., "Changes in Neurotransmitter Phenotype During Neuronal Differentiation of Retinoblastoma Cells," *Invest. Ophthalmol. Vis. Sci.*, 31(4):586, Mar. 15, 1990.

Li, A. et al., "Expression of Pigment Epithelial-Derived Factor in *Escherichia coli.*" *Journal of Bio. Chem.*, vol. 268, No. 31, pp. 23148-23156, (1993).

Becerra et al., "Overexpression of Fetal Human Pigment Epithelium-derived Factor *Escherichia coli*," *Journal of Bio. Chem.*, vol. 268, No. 31, pp. 23148-23156. (1993).

Tombran-Tink et al., "Neuronal Differentiation of Retinoblastoma Cells Induced by RPE-Conditioned Medium." *41st Annual Symposium on Fundamental Cancer Research*. p. 114 (1988).

Tombran-Tink et al., "Localization of the Gene for a Novel Neurotrophic Factor to Chromosome," *Proceedings of the American Association for Cancer Research*, vol. 34, p. 29 (Mar. 1993).

Tombran-Tink et al., Retinoblastoma: Induction of Neuronal Differentiation by Human Retinal Pigmented Epithelial Cell Conditioned Medium. Dissertation Abstracts International. vol. 51, No. 11 (May 1991).

Tombran-Tink et al., "Collagen-Induced Alterations in Intercellular Adhesion and Antigen Expression in Reinoblastoma Cells," *Exp. Eye Res.*, vol. 48, pp. 549-559 (1989).

Tombran-Tink et al., "Induction of Neuron-like Differentiation of Retinoblastoma Cells by RPE-Conditioned Medium," *8th Int. Cong. of Eye Res.* (1988).

Tombran-Tink et al., "Effects of RPE-Conditioned Medium on Neuronal Differentiation in Retinoblastoma Cells," *Proc. Int. Soc. Eye Res.* 4:170 (1990).

Li, A. et al., "Expression of Pigment Epithelial-Derived Factor (PEDF) in Human Normal and Tumor Cells," *Invest. Opthalmol. Vis. Sci.* 34 (4):870. (1993).

Campochiaro, et al., "Retinal pigment epithelial cells produce PDGF-like proteins and secrete them into their media," Exp. Eye Res., 1989, 49, 217-227.

Jacobs, K. et al., "Isolation and characterization of genomic and cDNA clones of human erythropoietin," Nature, 1985, 313, 806-810.

Sambrook, et al., Molecular Cloning, 2nd Ed., Cold Spring Harbor Lab Press, 1989, 16.3—16.81.

Seeburg, P.H. et al., "Efficient Bacterial Expression of Bovine and Porcine Growth Hormones," DNA, 1983, 2(1), 37-45.

Wallace, et al., "Methods in enzymology," Academic Press, 1987, 432-442.

Steele, F.R., et al., "Pigment epithelium-derived factor: neurotrophic activity and identification as a member of the serine protease inhibitor gene family," Proc. Natl. Acad. Sci. USA, 1993, 90(4), 1526-1530.

Seigel, G.M., et al., "Differentiation of Y79 Retinoblastoma Cells with Pigment Epithelial-Derived Factor and Interphotoreceptor Matrix Wash: Effects on Tumorigenicity," Growth Factors, 1994, 10, 289-297.

Rudinger, in Peptide hormones, *Univ. Park Press, Baltimore*, 1976, Parsons, J.A. (Ed.), 1-7.

Becerra, et al., "Pigment epithelium-derived factor: characterization using a highly specific polyclonal antibody," *FASEB J.*, 1994, 8(7), p. A1302, Abstract No. 252.

Campbell, M., et al., "Retinoblastoma cells in tissue culture," *Opthalmic Paediatrics and Genetics*, 1988, 9(3), 171-199.

Donoso, L.A., "Immunohistochemistry of retinoblastoma," *Ophthalmic Paediatrics and Genetics*, 1989, 10, 3-32.

Gaur, et al., "RPE conditioned medium stimulates photoreceptor cell survival, neurite outgrowth and differentiation in vitro," *Exp. Eye. Res.*, 1992, 54(5), 645-659.

Seigel, G.M., "The golden age of retinal cell culture," *Molecular Vision*, 1999, 5(4), 10 pages.

Sugita, et al., "Effects of pigment epithelium-derived factor (PEDF) on astrocytes and microglia in culture," *Soc. of Neuroscience Abstracts*, 1994, 20(1-2), No. 365.7, p. 873.

Tombran-Tink et al., "Partial Amino Acid Sequence and Neurotrophic Activity of a Novel Human Pigment Epithelium-Derived Factor (PEDF)," Investigative Ophthalmology & Visual Science, 1991, vol. 32, No. 4, p. 755, abstract No. 444.

Inazawa, J. et al., "Simultaneous Existence of Double Minute Chromosomes and a Homogeneously Staining Region in a Retinoblastoma Cell Line (Y79) and Amplification of N-myc at HSR," Cancer Genet Cytogenet, 1989, 37, 133-137.

McFall, R. et al., "Characterization of a New Continuous Cell Line Derived from a Human Retinoblastoma," Cancer Research, 1977, 37, 1003-1010.

Figure by Pat Becerra showing pre-PEDF, mature secreted PEDF and rPEDF-BH.

Cohen, J. et al., "Recombinant Forms of the Neurotrophic Factor Pigment Epithelium-Derived Factor Activate Cellular Metabolism and Inhibit Proliferation of the RAW Macrophage Cell Line," Neuroimmunomodulation, 2000, 7, 51-58.

* cited by examiner

RETINAL PIGMENTED EPITHELIUM DERIVED NEUROTROPHIC FACTOR

RELATED APPLICATIONS

This application is a continuation in part of U.S. patent application Ser. No. 07/894,215, filed Jun. 4, 1992 and U.S. patent application Ser. No. 07/952,796, filed Sep. 24, 1992, which are incorporated herein by reference.

This invention was made with government support under grant EY04741, awarded by The National Institutes of Health. The United States government has certain rights in this invention.

FIELD OF THE INVENTION

This invention relates to the purification and use of a retinal pigmented epithelium derived neurotrophic factor (PEDF). This invention also relates to a truncated version of PEDF that is referred to as PEDF-BH. In addition to PEDF and PEDF-BH and functionally equivalent proteins, this invention relates to nucleic acids that encode PEDF, PEDF-BH and functionally equivalent proteins, to vectors comprising such nucleic acids, to host cells into which such vectors have been introduced, and to the use of these host cells to produce such proteins.

BACKGROUND OF THE INVENTION

Many types of neurons depend upon the availability of special regulatory molecules, known as neurotrophic factors, for their survival and well-being. The best characterized of the neurotrophic factors is nerve growth factor (NGF). NGF regulates the survival and specialized function of sympathetic and dorsal root ganglion neurons in the peripheral nervous system and of some cholinergic neurons in the central nervous system. Trophic factors, which act on other neurons, have also been identified, and two such factors, ciliary neurotrophic factor (CNTF) and brain-derived neurotrophic factor (BDNF) have been purified. Moreover, it has recently been shown that some growth factors, such as fibroblast growth factor (FGF) and epidermal growth factor (EGF), which initially were identified based on their mitogenic effects upon cells, also function as survival-promoting agents for some neurons. Post-synaptic target cells and satellite cells, such as glial cells, appear to be major sources of neurotrophic factors.

It has been proposed that the survival of retinal photoreceptor cells may also be regulated by specific neurotrophic factors. Evidence supporting this concept includes the observation that photoreceptors undergo developmental neuronal death in some species, a phenomenon which is generally considered to reflect the limited availability of neurotrophic factors. Photoreceptor development, as well as maintenance of normal function, has also been shown to require interactions with the retinal pigment epithelium (RPE), suggesting that RPE-derived molecules or factors could be necessary for photoreceptor function and survival.

The RPE develops in advance of and lies adjacent to the neural retina. A closed compartment between the two cell layers contains the interphotoreceptor matrix, and many soluble secretory products of RPE and neural retina cells are contained in the interphotoreceptor matrix. Nutrients, metabolites or trophic factors exchanged between the RPE and neural retina, must pass through the interphotoreceptor matrix. RPE cells, for example, are thought to synthesize and secrete a photoreceptor survival-promoting factor (PSPA).

Cultured RPE cells synthesize a number of well known trophic factors, including platelet derived growth factor (PDGF), FGF, transforming growth factor-$\alpha$ (TGF-$\alpha$), and transforming growth factor-$\beta$ (TGF-$\beta$). It is possible that these or other unknown factors derived from RPE could influence the development of the neural retina.

The neural-derived RPE forms a monolayer of cells interposed between the neural retina and circulating blood within the choroid. In this strategic location, the RPE forms a part of the blood-retina barrier, performs functions essential to retinal integrity and functions, and plays important roles in vascular, inflammatory, degenerative, and dystrophic diseases of the retina and choroid. The functions of the RPE in relation to the visual process are several-fold and include light-dark adaption, phagocytosis of shed photoreceptor outer segment membrane and nutrition. On the other hand, the close interdependence of the RPE and the neural retina during normal development has been known for a long time, but functionally is not well understood, although it is known that the RPE is important for retinal regeneration. It has been consistently observed that loss of contact of the neural retina with the RPE of many vertebrates (retinal detachment) results in degeneration of the retina. As a side effect of the retinal detachment, strong cell proliferation, originating from the RPE which underlies the areas of detachment, has often been observed.

Thus, identification of hypothetical survival-promoting factors for photoreceptor cells would potentially be of great importance for the treatment of pathological conditions which result in blindness due to photoreceptor degeneration of unknown etiology. While these types of selective photoreceptor degenerations could be due to a variety of different mechanisms, analogies with neuronal degenerations in other regions of the nervous system suggest the possible involvement of a neurotrophic activity in the retina.

SUMMARY OF THE INVENTION

The present invention relates to a purified retinal pigmented epithelium derived neurotrophic factor composition and a method for purifying such a retinal pigmented epithelium neurotrophic factor. The purification procedure comprises providing an impure protein fraction containing retinal pigmented epithelium derived neurotrophic factor and applying the impure protein fraction containing retinal pigmented epithelium derived neurotrophic factor to a cation-exchange chromatography medium. The cation-exchange chromatography medium is then washed to elute any unbound proteins and the retinal pigmented epithelium derived neurotrophic factor is eluted from the cation-exchange chromatography medium and collected.

The present invention also relates to a recombinant DNA molecule comprising a gene encoding a retinal pigmented epithelium derived neurotrophic factor having the DNA sequence or the amino acid sequence in SEQ ID NO:1 and to an organism transformed with a recombinant DNA molecule comprising a retinal pigmented epithelium derived neurotrophic factor gene having a DNA sequence identified in SEQ ID NO:1.

The present invention also relates to a method of treating tumors, ocular diseases and conditions resulting from the activity of serine proteases which comprises administering PEDF.

DETAILED DESCRIPTION

Cells of the retinal pigmented epithelium are closely associated with differentiating retinoblasts in vivo and contribute to an environment essential to their development and normal function, both in vivo and in vitro. Retinoblastoma cells exhibit a multi-potential differentiative nature paralleling that of their precursor, the primitive retinoblast, as evidenced by the fact that agents, such as laminin, sodium butyrate and dibutyryl cAMP, can induce the expression of neuronal, glial, and pigmented epithelial characteristics in vitro.

A human retinoblastoma cultured cell line, Y79 cells, when exposed to RPE-conditioned medium (RPE-CM), exhibits a high degree of neuronal-like differentiation. The differentiation is observed in both the morphological and biochemical characteristics of the cells. The exposed cells extend arborizing neuritic processes from their cell bodies and express elevated levels of neuron-specific enolase (NSE) and neurofilament proteins. In addition, RPE-CM extends the life of the attached, differentiated cells for more than 30 days as compared to 10 to 15 days for non-treated cells.

RPE-secreted proteins have been fractionated from RPE-CM, and a protein doublet, with an apparent molecular weight of about 50,000 to about 55,000, that is unique to RPE-CM has been identified. This pigment epithelium derived neurotrophic factor (PEDF), which is a major secretory product of human fetal RPE cells, has been isolated and shown to have neurotrophic effects on Y79 retinoblastoma cells. Additionally, a smaller 36,000 molecular weight, form of PEDF has also been identified.

PEDF has uses in the treatment of retinal diseases including, but not limited to, retinoblastoma and other ocular tumors, retinitis pigmentosa, various forms of retinal detachment, macular degeneration, diabetic retinopathy, and other inherited and age-related pathologies of retinal cells.

In the case of retinal tumors, PEDF induces the tumor cells to display biochemical and phenotypic characteristics of mature neuronal cells. Such changes are identified by a cessation or reduction in the rate of cell division, which leads to tumor regression or a slowing in the rate of tumor growth. In the case of non-tumorous retinal diseases, the neurotrophic properties of PEDF enhance survival and well-being of photoreceptor or other retinal cells, prolonging their functional life span and delaying the rate of the onset of impaired vision and ultimate blindness. In the case of retinal detachment, PEDF prolongs the life span of photoreceptor cells sufficiently to allow standard reattachment procedures to be effective in re-establishing the retina-RPE interface, thereby restoring normal vision.

1. Preparation of an Impure Protein Fraction Containing Retinal Pigmented Epithelium Derived Neurotrophic Factor Retinal pigmented epithelium derived neurotrophic factor (PEDF) may be isolated from any tissue or cell producing PEDF.

Naturally-occurring cells that produce PEDF are retinal pigmented epithelium cells. Such cells may be grown in culture to secrete PEDF into the medium in which they are growing. The medium may be harvested periodically, and the PEDF isolated from the media. Suitable cell cultures may be established from retinal pigmented epithelium cells derived from humans, monkeys, and other primates or other animals, such as chickens, mice, rats, cows and pigs. PDEF may also be isolated from the vitreous humor of human, bovine, monkey and other primates. The vitreous contains an abundance of PEDF and is very easy to remove from the eye cup. This is probably the easiest source from which to isolate PEDF PEDF may also be isolated by extraction of the interphotoreceptor matrix (IPM) or from the retina of humans, monkeys, and other primates or other animals, such as chickens, mice, rats, cows and pigs.

Alternatively PEDF may be derived from sources in which it is not naturally-occurring, such as organisms transfected with a recombinant DNA molecule constructed to result in the expression of PEDF or a PEDF equivalent protein in the host cells chosen for the expression of the gene. It is well known in the art that proteins can be modified by deletion, addition or substitution of amino acids without changing the function of the protein. Such proteins which retain the specificity of PEDF are considered to be equivalent.

A. Culturing of Human Retinal Pigmented Epithelium (RPE) Cells

Cultures of RPE cells are established by harvesting postmortem eyes by aseptically opening the eyes and removing the vitreous body and retina. The exposed RPE is washed with a buffered solution such as modified Earle's balanced salt solution (MEBS: 115.5 mM NaCl, 3.5 mM KCl, 1 mM $NaH_2PO_4$, 0.5 mM $CaCl_2$, 0.27 mM $MgCl_2$, 0.37 $MgSO_4$, 15 mM HEPES, 14 mM $NaHCO_3$, 12 mM glucose, pH 7.2). RPE cells are scraped from Bruch's membrane or are dislodged by a stream of fluid such as MEBS or cell culture medium, applied using a Pasteur or similar pipette. This step may be preceded by exposure to proteolytic or other enzyme(s), such as Dispase (Boehringer-Mannheim, Indianapolis, Ind. Catalog #295 825). Alternatively, RPE cells may be isolated by detaching sections of sclera from an intact eye to expose choroidal tissue and treating this choroidal surface with proteolytic or other enzymes such as Dispase prior to removal of the vitreous and retina and dislodging RPE cells by the spraying of cell culture medium as described by Pfeffer et al., *J. Cell. Physiol.* 117 333-341 (1983). Tissue fragments are transferred to tissue culture dishes in a medium such as "low $Ca^{++}$" or "high $Ca^{++}$" complete RPE-47 medium, as described by Pfeffer et al., *J. Cell. Physiol.* 117 333-341 (1983), or Eagles's minimal essential medium (MEM, supplied by GIBCO of Grand Island, N.Y.) supplemented with about 0.5% to about 20% v/v fetal calf serum. At concentrations below about 0.5% v/v fetal calf serum, the serum concentrations are too low to effectively support the growth of the cells. At concentrations above about 20% v/v serum, no additional benefit, with respect to cell growth, is conferred on the cells.

The medium may also be supplemented with antibiotics and/or fungicides to prevent the growth of bacteria and/or fungi in the cultures. Antibiotics and fungicides suitable for use in the present invention are about 1,000 units/ml penicillin, about 100 μg/ml streptomycin, about 0.25 μg amphotericin, and about 50 μg/ml gentamicin, or other suitable such agents known in the art. These antibiotics may be used individually or in combination, as desired.

The cells are incubated at about 37° C. in an atmosphere of about 5% v/v $CO_2$. Retinal pigmented epithelium (RPE) cells attach to the surface of the dishes, proliferate, and eventually form confluent monolayers.

When the cells have grown to confluence, about 3-7 days from the initial culturing of the cells, they are harvested, for example, by trypsinizing the cell monolayer, or by other methods known to those skilled in the art, and resuspending the cells in a medium such as MEM, supplied by GIBCO, supplemented with about 5% v/v to about 20% v/v fetal calf serum. A portion of the cells are reseeded into sterile tissue culture flasks, after which time the cells are again grown in an atmosphere of about 5% v/v $CO_2$ at about 37° C.

Alternatively, RPE cells may be isolated by removing the cornea, the 2 mm scleral ring, and the vitreous and neural retina from the eyes. The eyes are washed with calcium and magnesium-free Hanks Balanced Salt Solution (HBSS: 1.3 mM $CaCl_2$, 5 mM KCl, 0.3 mM $KH_2PO_4$, 0.5 mM $MgCl_2$, 0.4 mM MgSO$_4$, 138 mM NaCl, 4 mM NaHCO$_3$, 0.3 mM Na$_2$HPO$_4$, 5.6 mM D-glucose and 0.03 mM Phenol Red, supplied by GIBCO/BRL of Gaithersburg, Md.). The eye cup is filled with a solution comprising about 0.1% w/v trypsin, about 0.1% w/v hyaluronidase in calcium and magnesium-free Hanks balanced salt solution, and the eye is incubated at about 37° C. for about 15 to about 30 minutes.

The loose RPE cells are collected by gentle aspiration, and the procedure is repeated until the RPE cells are released. The trypsin is inactivated by adding about 5% v/v to about 20% v/v fetal calf serum to the cell sample. The cells are collected by centrifugation at about 1,200 rpm for about 7 minutes.

The RPE cells are then plated onto sterile tissue culture plates at a density of about 1×10$^5$ cells for a 35 mm plate. (Proportionally more or less cells are plated if larger or smaller plates or containers are used.) The cells are grown in DulBecco's Modified Eagles Medium (DMEM), supplied by GIBCO, or other suitable medium. The medium may be supplemented with an equal volume of HAM's F12 medium (supplied by GIBCO),—about 1 mM sodium pyruvate, about 0.625 mM Hepes, about 6 mM L-glutamine, about 1% w/v non-essential amino acids, about 5 µg/ml insulin, about 5 µg/ml transferrin, about 5 ng/ml selenium, antibiotics as described above, and about 0.5% v/v to about 20% v/v fetal calf serum, as described above. The insulin, transferrin, and selenium are supplied by Collaborative Research of Lexington, Mass. Other reagents suitable for use in the present invention, unless otherwise specified, are supplied by Sigma Chemical Co. of St Louis, Mo.

When the cells have grown to confluence (about 3-7 days from the initial culturing of the cells), they are harvested, for example, by trypsinizing the cell monolayer or by other methods known to those skilled in the art, and resuspending the cells in a medium such as MEM supplemented with about 0.5% v/v to about 20% v/v fetal calf serum. A portion of the cells are reseeded into sterile tissue culture flasks, after which time the cells are again grown in an atmosphere of about 5% v/v CO$_2$ at about 37° C.

While only two methods for the culturing of RPE cells are described, other suitable methods for culturing RPE cells are known in the art. Such methods are also suitable for use in the practice of the present invention.

B. Preparation of Retinal Pigmented Epithelium Conditioned Medium (RPE-CM)

PEDF is a secreted protein, and RPE cells secrete PEDF into the medium in which they are grown. Therefore, a convenient method of producing PEDF is to grow RPE cells in culture and to periodically harvest the media from the cultures.

A method suitable for use in the present invention for isolating PEDF from medium is to allow RPE cells to grow to confluence in a medium such as DMEM supplemented with about 1 mM sodium pyruvate, about 0.625 mM Hepes, about 6 mM L-glutamine, about 1% w/v non-essential amino acids, about 5 µg/ml insulin, about 5 µg/ml transferrin, about 5 ng/ml selenium, antibiotics and/or fungicides as described above, and about 0.5% v/v to about 20% v/v fetal calf serum, as described above. The confluent cultures of RPE cells are washed extensively with Hank's balanced salt solution, or other suitable wash solutions, to remove serum proteins derived from the fetal calf serum present in the media used to culture the RPE cells. About 1 ml, per cm$^2$ of cell surface area, of serum-free medium such as DMEM supplemented with about 1 mM sodium pyruvate, about 0.625 mM Hepes, about 6 mM L-glutamine about 1% w/v non-essential amino acids, about 5 µg/ml insulin, about 5 µg/ml transferrin, about 5 ng/ml selenium, and antibiotics and/or fungicides as described above, is added to the cultures, and they are incubated in an atmosphere of about 5% v/v CO$_2$ at about 37° C. for about 1 to about 10 days. Alternatively, PEDF can be isolated from serum-containing medium such as DMEM supplemented with about 1 mM sodium pyruvate, about 0.625 mM Hepes, about 6 mM L-glutamine, about 1% w/v non-essential amino acids, about 5 µg/ml insulin, about 5 µg/ml transferring about 5 ng/ml selenium, antibiotics and/or fungicides as described above, and about 0.5% v/v to about 20% v/v fetal calf serum as described above.

The medium is then collected by pouring the medium into plastic centrifuge tubes, and the medium is centrifuged at about 3,000 rpm for about 10 minutes to remove any free cells and other particulate matter from the medium, and filtered to provide an impure PEDF protein solution. The medium may be used directly for the purification or testing of PEDF or it may be stored at −20° C. until required.

C. Isolation of PEDF from Tissue Samples

PEDF may be isolated directly from eyes by opening the eyes and removing the vitreous body and retina. The retinal pigmented epithelium is scraped off the Bruch's membrane using a disposable cell scraper. Tissue fragments are transferred to a Teflon or glass homogenizer in a solution such as 10 mM phosphate-buffered saline (PBS) and homogenized to break the cells. The solution is then centrifuged at about 10,000 rpm for about 10 minutes and filtered to remove cell debris. The supernatant, which contains PEDF, is collected to provide an impure PEDF protein solution. The medium may be used directly for the purification or testing of PEDF or it may be stored at −20° C. until required.

D. Isolation of PEDF from Bovine Vitreous

The vitreous is a gel like substance which fills the eye cup. The vitreaous is removed from the eye and solubilized by freezing and thawing. About 20 ml of solubilized vitreous are obtained per bovine eye cup and this volume contains about 16 g/100 µl of vitreous.

F. Isolation of PEDF from Recombinant Cells

PEDF may also be isolated from recombinant cells which have been constructed to express the PEDF gene. The PEDF may be expressed as an intracellular or an extracellular protein.

Intracellular PEDF is isolated by homogenizing the cells in a Dounce or other suitable homogenizer in a buffer, such as PBS, that may contain detergents or other solubilizing agents such as urea or guanidine hydrochloride, and centrifuging at about 10,000 rpm for about 20 minutes to remove cellular debris, to provide an impure PEDF protein fraction.

Extracellular PEDF is isolated by collecting the medium in which cells expressing PEDF are grown. This is most conveniently performed in a continuous centrifugation process, such as with a Sharples centrifuge. The supernatant is collected to provide an impure PEDF protein fraction. The medium may be used directly for the purification or testing of PEDF or it may be stored at −20° C. until required.

2. Purification of PEDF

A. Small Scale Purification of PEDF i. Ammonium Sulfate Precipitation

An impure PEDF protein fraction may be partially purified by ammonium sulfate precipitation to provide an ammonium sulfate purified PEDF protein fraction. Percent ammonium sulfate refers to % saturation of ammonium sulfate at 20° C. and is based on a 100% saturation of 767 g/l.

An impure PEDF protein fraction is brought to about 50% saturation with ammonium sulfate by the addition of about 313 g of solid ammonium sulfate per liter of impure protein fraction at about 20° C. The ammonium sulfate is preferably added slowly to the impure protein fraction while the solution is stirred, such as with a stir bar on a mechanical stirrer. The ammonium sulfate is added slowly to prevent localized high concentrations of ammonium sulfate that may result in rapid precipitation and denaturation of proteins present in the impure protein fraction. After all the ammonium sulfate is added, the about-50% ammonium sulfate solution is stirred for about 30 minutes at about 20° C. The about-50% ammonium sulfate solution is then centrifuged at about 10,000 g, at about 20° C. for about 20 minutes. The supernatant is collected for further processing. Alternatively, the about-50% ammonium sulfate solution may be filtered through filter paper such as Whatman #1, to remove the precipitate. In this case, the filtrate is collected for further processing.

The about-50% ammonium sulfate solution is then brought to about 70% saturation by the addition of about 137 g/l of ammonium sulfate. The ammonium sulfate is added slowly, and after all the ammonium sulfate is added, the about-70% ammonium sulfate solution is stirred for about 30 minutes at about 20° C. The about-70% ammonium sulfate solution is centrifuged or filtered, as described above, and the precipitate is collected.

The ammonium sulfate precipitate is then redissolved in a buffer such as about 10 mM phosphate, pH 7, to form a 50-70% ammonium sulfate fraction. The solution is then diafiltered using an Amicon Diaflo ultrafiltration unit, or dialyzed against a buffer such as about 10 mM phosphate, pH 7, to remove the residual ammonium sulfate from the redissolved 50%-70% ammonium sulfate fraction.

ii. Purification of PEDF by SDS Gel Electrophoresis

A small-scale isolation of PEDF is conducted by SDS-polyacrylamide slab gels. Such polyacrylamide gels are well known in the art, and the preparation of such gels has been described by Weber and Osborn, J. Biol. Chem. 244 4406 (1969), as modified by Laemmli, Nature 277 680 (1970).

Samples of an impure PEDF protein fraction or ammonium sulfate purified PEDF protein fraction are dialyzed against a buffer such as about 10 mM sodium phosphate buffer, pH 7.5, lyophilized and resuspended in 62.5 mM Tris, pH 6.8, 2% w/v SDS, 10% v/v glycerol, 0.001% w/v bromophenol blue, and 0.1 M 2-mercaptoethanol, wherein the bromophenol blue is a migration marker. Additional samples to be loaded on the gel include molecular-weight standards such as phosphorylase B, bovine serum albumin, ovalbumin, carbonic anhydrase, soybean trypsin inhibitor and lysozyme (such as supplied by Bio-Rad, catalog #161-0304), and controls as may be necessary. In cases where conditioned media are used as samples, media which have not been exposed to RPE cells (unconditioned media) are included as controls.

The samples are then incubated in a boiling-water bath for about 5 minutes and loaded onto SDS-polyacrylamide slab gels. The markers and unconditioned media are loaded into wells on the outside of the gel, and the impure PEDF protein fractions or the ammonium sulfate purified PEDF protein fraction are loaded on the remaining inside wells. The samples are then subjected to electrophoresis. The electrophoresis is continued until the bromphenol blue marker has reached the bottom of the gel. At the completion of electrophoresis, strips from each outside edge of the gels, which included the markers and a lane each of an impure PEDF protein fraction and an unconditioned media control, are stained with Coomassie blue. The stained protein bands which develop on the stained strips are aligned with the unstained portion of the gel to locate the position of the proteins present in the impure PEDF protein fraction or the ammonium sulfate purified PEDF protein fraction but absent from control media.

A PEDF protein doublet, with an apparent molecular weight of about 50,000 to about 55,000, unique to the impure PEDF protein fraction, is excised and the proteins electroeluted, by methods known in the art, from the unstained portion of the gel. The eluant is centrifuged to remove gel fragments and the supernatant dialyzed against 10 mM phosphate-buffered saline (145 mM NaCl, 8.1 mM $Na_2HPO_4$, and 1.9 mM $NAH_2PO_4.H_2O$) to provide an SDS-polyacrylamide purified PEDF protein fraction.

iii. Purification of PEDF Using BioRad PREP CELL large quantities of PEDF can be purified by using BioRad PREP CELL which is an electrophoresis unit containing a tube gel. Samples are loaded onto the top of the tube gel and fractions are collected from the bottom. Individual fractions are examined by SDS gel electrophoresis for a 50,000 molecular weight protein. Fractions containing a 50,000 molecular weight protein are collected and pooled.

iv. Purification of PEDF by Cation-Exchange HPLC

An impure PEDF protein fraction or an ammonium sulfate purified PEDF protein fraction is dialyzed against water or a buffer such as about 10 mM phosphate buffer, pH 7.2, or other suitable buffer, to remove media and salts from the impure protein sample. PEDF may be purified by cation-exchange HPLC using a column chromatography medium, such as that supplied under the trade name "Brownlee Aquapore CX-300", by Western Analytical, Temecula, Calif., packed into a column, such as a 4.6×30 mm column, or other suitable cation-exchange HPLC chromatography medium.

The chromatography medium is equilibrated with a buffer such as about 10 mM phosphate, pH 7.2. The dialyzed impure PEDF protein fraction or ammonium sulfate purified PEDF protein fraction is loaded onto the chromatography medium, and the chromatography medium with PEDF bound to it is washed with a buffer such as about 10 mM phosphate, pH 7.2, until all unbound proteins are washed from the chromatography medium. PEDF is eluted from the chromatograph medium with a linear salt gradient from about 0.0 to about 0.5 M NaCl. PEDF elutes as a single peak with a NaCl concentration of about 0.25 M.

The eluted PEDF is concentrated by lyophilization and resolubilized in water or a buffer such as about 10 mM phosphate buffer, pH 7.2, or other suitable buffer, to form a cation-exchange HPLC purified PEDF protein fraction.

iv. Purification of PEDF by Reverse-Phase HPLC

An impure PEDF protein fraction or ammonium sulfate purified PEDF protein fraction is dialyzed against a buffer such as about 10 mM phosphate buffer, pH 7.2, or other suitable buffer, to remove media and salts from the impure protein sample. PEDF may be purified by reverse-phase HPLC using a column chromatography medium such as a chromatography medium supplied under the trade name "Vydac C8" by The Separation Group of Hesperia, Calif., packed into a column such as a 4.6×250 mm column or other suitable reverse-phase HPLC chromatography medium.

The chromatography medium is equilibrated with a solution such as about 0.1% v/v trifluoroacetic acid (TFA). The dialyzed impure PEDF protein fraction or ammonium sulfate purified PEDF protein fraction is loaded onto the chromatography medium, and the chromatography medium with PEDF bound to it is washed with an eluant such as 0.1% v/v TFA, until all unbound proteins are washed from the chromatography medium. PEDF is eluted from the chromatograph medium with a linear gradient from about 0.1% v/v TFA in water to about 95% v/v acetonitrile ($CH_3CN$), 0.1% v/v TFA, 5% v/v H₂O. PEDF elutes as a single peak with a $CH_3CN$ concentration of about 70% v/v.

The eluted PEDF is concentrated by lyophilization and resolubilized in water or a buffer such as about 10 mM phosphate buffer, pH 7.2, or other suitable buffer, to form a reverse-phase HPLC purified PEDF protein fraction.

V. Size-Exclusion HPLC

An impure PEDF protein fraction, an ammonium sulfate purified PEDF protein fraction, a cation-exchange HPLC purified PEDF protein fraction, or a reverse-phase HPLC purified PEDF protein fraction may be purified by size-exclusion chromatograph using a chromatography medium, such as that supplied under the trade name "Bio-Rad TSK-250" by Bio-Rad of Richmond, Calif., packed into a column such as a 7.5×300 mm column. The impure PEDF protein fraction, the ammonium sulfate purified PEDF protein fraction, the cation-exchange HPLC purified PEDF protein fraction, or the reverse-phase HPLC purified PEDF protein fraction is loaded onto the size-exclusion chromatography medium, which has been equilibrated with a buffer such as 0.02 M Tris-HCl, pH 7.0, 0.6 M NaCl. PEDF-containing fractions are collected and dialyzed against a buffer such as about 10 mM phosphate buffer, pH 7.2 to provide a size-exclusion purified PEDF protein fraction.

vi. Heparin Chromatography

An impure PEDF protein fraction or an ammonium sulfate purified PEDF protein fraction may also be purified by heparin chromatography. A heparin chromatography medium such as heparin agarose, supplied by Sigma Chemical Co. of St Louis, Mo. (Cat. No. H-5380), is equilibrated with a buffer such as about 10 mM Tris-HCl, pH 7.5.

An impure PEDF protein fraction or an ammonium sulfate purified PEDF protein fraction is dialyzed against a buffer such as about 10 mM Tris, pH 7.5, to remove any salts or media from the samples, and the dialyzed PEDF solution is applied to the equilibrated heparin agarose. After the PEDF solution has been applied to the heparin agarose, the heparin agarose is washed with a buffer such as about 10 mM Tris-HCl, pH 7.5, until all unbound proteins are eluted from the heparin agarose. PEDF is then eluted from the heparin agarose with a buffer such as about 10 mM Tris-HCl, pH 7.5, 0.5 M NaCl.

The eluate containing PEDF is then diafiltered in an Amicon Diaflo ultrafiltration unit, or is dialyzed against a buffer such as about 10 mM Tris-HCl, pH 7.5, to remove NaCl present in the eluate, thereby providing a heparin purified PEDF protein fraction.

The above-described purification procedures may use an impure PEDF protein fraction or an ammonium sulfate purified PEDF protein fraction as the starting material for the subsequent column purification. Alternatively, a protein fraction which has already been purified by one or more of the described chromatography steps could also be used. Therefore, the purification procedures may be used alone or in combination with each other or with other purification techniques known in the art to produce a PEDF protein fraction of the desired purity.

B. Large-Scale Preparation of PEDF i. Ammonium Sulfate Precipitation

Large-scale purification of PEDF may be prepared by ammonium sulfate precipitation to provide an ammonium sulfate purified PEDF protein fraction.

An impure PEDF protein fraction is brought to about 50% saturation with ammonium sulfate by the addition of about 313 g of solid ammonium sulfate per liter of impure PEDF protein fraction. The ammonium sulfate is preferably added slowly to the impure protein fraction while the solution is stirred, such as with a stir bar on a mechanical stirrer. The ammonium sulfate is added slowly to prevent localized high concentrations of ammonium sulfate which may result in rapid precipitation, and denaturation of proteins present in the impure protein fraction. After all the ammonium sulfate is added, the 50% ammonium sulfate solution is stirred for about 30 minutes at 20° C. The 50% ammonium sulfate solution is then centrifuged at about 10,000 g, at 20° C. for about 20 minutes. The supernatant is collected for further processing. Alternatively, the 50% ammonium sulfate solution may be filtered through filter paper, such as Whatman #1, to remove the precipitate. The filtrate is collected for further processing.

The 50% ammonium sulfate solution is then brought to about 70% saturation by the addition of about 137 g/l of ammonium sulfate. The ammonium sulfate is added slowly, and after all the ammonium sulfate is added, the 70% ammonium sulfate solution is stirred for about 30 minutes at 20° C. The 70% ammonium sulfate solution is centrifuged or filtered, as described above, and the precipitate is collected.

The ammonium sulfate precipitate is then redissolved in a buffer such as about 10 mM phosphate, pH 7, to form a 50-70% ammonium sulphate fraction, then diafiltered using an Amicon Diaflo ultrafiltration unit, or dialyzed against about 10 mM sodium phosphate, pH 7, to remove the ammonium sulfate from the redissolved 50-70% fraction to provide an ammonium sulfate purified PEDF protein fraction.

ii. Anion-Exchange Chromatography

The pI of the PEDF protein is about 3.9 to about 7.2. Therefore, at a pH of about 7.5, the protein has a net negative charge and binds to an anion-exchange chromatography medium such as DEAE (diethylaminoethyl) cellulose.

For use, an anion-exchange chromatography medium such as DEAE cellulose is equilibrated with a buffer such as about 10 mM Tris, pH 7.5. The PEDF is applied to the anion-exchange chromatography medium, and the medium is washed with a buffer such as about 10 mM Tris, pH 7.5, until all unbound proteins are eluted from the column. After all the unbound proteins are eluted, PEDF is eluted with a linear salt gradient from about 0 to about 1 M NaCl in a buffer such as about 10 mM Tris-HCl, pH 7.5. The fractions containing PEDF are collected and pooled. These fractions are then diafiltered or dialyzed against a buffer such as about 10 mM Tris-HCl, pH 7.5, to remove NaCl, thereby providing an anion-exchange chromatography purified PEDF protein fraction.

Anion-exchange chromatography may be conducted by either batch or column chromatography techniques.

iii. Heparin Chromatography

Heparin chromatography may also be used for the large-scale purification of PEDF. A heparin chromatography medium such as heparin agarose, supplied by Sigma Chemical Co. (Cat. No. H-5380), is equilibrated with a buffer such as about 10 mM Tris-HCl, pH 7.5.

An impure PEDF protein fraction or an ammonium sulfate purified PEDF protein fraction is dialyzed against a buffer such as about 10 mM Tris-HCl, pH 7.5, and then applied to the heparin agarose. After the PEDF solution has been applied to the heparin agarose, the heparin agarose is washed with a buffer such as about 10 mM Tris-HCl, pH 7.5, until all unbound proteins are eluted from the heparin agarose. PEDF is then eluted from the heparin agarose with a buffer such as about 10 mM Tris-HCl, pH 7.5, 0.5 M NaCl.

The eluant containing PEDF is collected and diafiltered in an Amicon Diaflo ultrafiltration unit, or dialyzed against a buffer such as about 10 mM Tris-HCl, pH 7.5, to remove the NaCl present in the eluate, to provide a heparin purified PEDF protein fraction.

The above-described purification procedures may use an impure PEDF protein fraction or an ammonium sulfate purified PEDF protein fraction as the starting material for the subsequent column purification. Alternatively, a protein fraction which has already been purified by one or more of the described chromatography steps could also be used. Therefore, the purification procedures may be used alone or in combination with each other or with other purification techniques known in the art to produce a PEDF protein fraction of the desired purity.

3. PEDF Assays

A. SDS Gel Electrophoresis

PEDF may be identified by SDS-polyacrylamide gel electrophoresis on, for example, 7.5%, 10%, 12.5% w/v SDS-polyacrylamide gels. The preparation of such gels has been described by Weber and Osborn *J. Biol. Chem.* 244 4406 (1969), as modified by Laemmli, *Nature* 277 680 (1970), and the preparation and use of such gels are well known in the art.

The PEDF protein samples are mixed with about 5 µl of 62.5 mM Tris, pH 6.8, 12% w/v SDS, 0.001% w/v bromophenol blue, 10% v/v glycerol, and 0.1 M 2-mercaptoethanol, wherein the bromophenol blue is a marker. Molecular-weight marker samples which include molecular-weight standards such as phosphorylase B, bovine serum albumin, ovalbumin, carbonic anhydrase, soybean trypsin inhibitor and lysozyme (such as supplied by Bio-Rad, catalog #161-0304) are included on the gels as controls. The PEDF protein samples and the molecular-weight standards are boiled for about 5 minutes and loaded onto separate wells on the SDS-polyacrylamide slab gels. The samples are then subjected to electrophoresis until the bromphenol blue has migrated to the bottom of the gel. At the completion of electrophoresis, the gel is silver-stained, stained with Coomassie blue, or stained by other suitable protein staining methods. The molecular weight of proteins in the PEDF sample is then compared to the molecular-weight standards.

Alternatively, larger quantities of PEDF can be collected from SDS-PAGE tube gels using BioRad PREP CELL equipment and a fraction collector.

PEDF migrates as a protein doublet, with an apparent molecular weight of from about 50,000 to about 55,000 on SDS polyacrylamide gels.

B. Neuronal Inductivity

PEDF activity in protein samples may be assayed by its neuronal inductivity. Various concentrations of PEDF are added to cultures of cells such as Y79 retinoblastoma (RB) cells, supplied by the American Type Culture Collection, Access No. HTB 18, of Rockville, Md.

The Y79 RB cells are grown in suspension culture. The cells are harvested by centrifugation for about 5 minutes at about 900 rpm at room temperature and resuspended in a serum-free medium such as Dulbecco's modified Eagle's medium supplemented with 5 ug/ml insulin, 5 ug/ml transferrin, 5 ng/ml selenous acid, and 876.6 ug/ml L-glutamine (serum-free medium), which has previously been warmed to about 37° C. The collected cells are resuspended at a concentration of about $10^6$ cells/ml in serum-free medium. About 50 to about 500 ng/ml of PEDF is added to about 25 ml aliquots of the cells. The cells are incubated for about 7 days at about 37° C., then attached to poly-D-lysine-coated flasks or glass coverslips. The poly-D-lysine-coated flasks are prepared by coating with a solution containing about 200 ug/ml poly-D-lysine (such as that supplied by Sigma, Catalog #P7405) for about 1-24 hours, followed by rinsing with water and serum-free medium. Other cells may be used and it will be clear to one skilled in the art that testing other cells is a routine matter of following the methods set out above with the desired cell line.

i. Cell Analyses

Morphology of attached cells is monitored daily by phase contrast microscopy of living cells using a microscope such as an inverted Diaphot TMD microscope, supplied by Nikon of Tokyo, Japan, or by differential interference contrast microscopy of cells, fixed with a fixative such as about 4% v/v paraformaldehyde in 0.1 M sodium cacodylate buffer, using a microscope, such as a BHS-BH2 microscope, supplied by Olympus of Tokyo, Japan.

Differentiation is assessed by calculating the percentage of cellular aggregates (more than 90% of Y79 cells plated from suspension culture attach to poly-D-lysine-coated flasks as aggregates containing more than 5 cells) in which cells extend processes at day 1, 3, 7 and 11 after attachment. Experiments are performed in replicates of 3 and are repeated twice.

Expression of neuron-specific enolase (NSE) and neurofilament 200,000 molecular weight protein subunit (NF 200) is monitored by immunofluorescence and viewed by either epifluorescence microscopy (Olympus BHS-BH2 microscope) or microspectrofluorometry (MSA, Farrand Microscope Spectrum Analyzer). Quantification is by 1) visual scoring of intensity of fluorescence at 485 nm excitation as +=weak; ++=moderate; +++=strong; ++++=very intense, and 2) microspectrofluorometric analysis (MSA) readings (µA×100, time constant of about 0.3 seconds; specimen size of approximately 2 mm or about 100 cells/aggregate; target size of about 15 µm or approximately that of 1 cell).

The presence of PEDF in the protein sample results in the Y79 RB cells, extending neurite-like processes. At a concentration of about 500 ng/ml, about 70% of the cells extend neurite-like processes.

ii. Differentiation

Cells were cultured as described above. The cells were then monitored daily by phase-contrast microscopy of living cells (Olympus IMT-2) and by differential interference contrast microscopy (Olympus BHS) of cells fixed with a fixative such as about 4% v/v paraformaldehyde. The percentage of differentiating cells is estimated by calculating the number of cellular aggregates containing five or more cells exhibiting neurite outgrowths following 8-10 days of culture on a poly-D-lysine substratum.

With about 50 to about 500 ng/ml PEDF, approximately 80% of the cells undergo morphological differentiation within about 3 days.

4. Characterization of the PEDF Protein

A. Isolation of PEDF Peptides

Purified PEDF, about 500 µg, is concentrated using Centricon 10 microconcentrators (Amicon, Danvers, Mass.), and then diluted in a suitable digestion buffer such as about 25 mM Tris, pH 8.5, 1 mM EDTA. To the protein sample is added a proteolytic enzyme, such as endoproteinase Lys-C, supplied by Boehringer-Mannheim of Indianapolis, Ind. The PEDF/proteinase mixture is incubated for about 18 hours at about 30° C., or until the reaction has gone to completion, i.e., until all the PEDF is completely digested by the proteinase. Alternatively, the protein may be digested with trypsin in a buffer comprising about 10 mM PBS or by using other proteinases known in the art.

The resulting PEDF polypeptide fragments are separated by using a separation system such as HPLC on a Vydac C8 reverse-phase column. A 4.6×250 mm column is suitable for use in the present invention. The column is equilibrated with about 0.1% v/v TFA in water. The polypeptides are eluted with about 90% v/v $CH_3CN$, 0.1% v/v TFA and 5% v/v $H_2O$.

Polypeptides eluted from the column which are well separated from other polypeptides are collected and subjected to protein sequencing analysis.

B. Protein Sequencing Analysis

The purified polypeptide fragments are subjected to amino-acid sequence analysis by methods known in the art. Alternatively, the amino-acid sequence analysis is conveniently performed under contract at an amino-acid sequencing facility, such as the Microsequencing Facility of Beckman Research Institute at the City of Hope in Duarte, Calif.

5. Characterization of the PEDF Gene

The present invention provides, among other things, a nucleic acid which encodes PEDF. In particular, a cDNA sequence is provided for human PEDF as set forth in SEQ ID NO:1, for mouse PEDF as set forth in SEQ ID NO:7 and for human PEDF as set forth in SEQ ID NO:8. This cDNA sequence codes for PEDF, which has the amino acid sequence set forth in SEQ ID NO:2. The cDNA and amino acid sequences are listed in the GenBank® Data Bank under accession number M76979.

The term "nucleic acid" refers to a polymer of deoxyribonucleic acid (DNA) or ribonucleic acid (RNA), which can be derived from any source, can be single- or double-stranded, and can optionally contain synthetic, non-natural, or altered nucleotides which are capable of being incorporated into DNA or RNA polymers. The nucleic acid of the present invention is preferably a segment of DNA.

The present invention further provides a truncated version of PEDF, which is referred to as PEDF-BH. PEDF-BH comprises the amino acid sequence Met-Asn-Arg-Ile (SEQ ID NO:48) fused to $Asp^{44}$ . . . $Pro^{418}$ of PEDF, the amino terminus of which has been deleted. The truncated protein comprises the amino acid sequence of SEQ ID NO:3. The present invention also provides a nucleic acid which encodes a protein comprising the amino acid sequence of PEDF-BH, i.e., the amino acid sequence of SEQ ID NO:3.

One who is skilled in the art will appreciate that more than one nucleic acid may encode any given protein in view of the degeneracy of the genetic code and the allowance of exceptions to classical base pairing in the third position of the codon, as given by the so-called "Wobble rules." Moreover, nucleic acids that include more or less nucleotides can result in the same or equivalent proteins. Accordingly, it is intended that the present invention encompass all nucleic acids that encode the amino acid sequences of SEQ ID NO:2 and SEQ ID NO:3, as well as equivalent proteins. The phrase "equivalent nucleic acids" is intended to encompass all of these nucleic acids.

It also will be appreciated by one skilled in the art that amino acid sequences may be altered without adversely affecting the function of a particular protein. In fact, some alterations in amino acid sequence may result in a protein with improved characteristics. The determination of which amino acids may be altered without adversely affecting the function of a protein is well within the ordinary skill in the art. Moreover, proteins that include more or less amino acids can result in proteins that are functionally equivalent. Accordingly, it is intended that the present invention encompass all amino acid sequences that result in the PEDF and PEDF-BH proteins, proteins that are functionally equivalent to PEDF and PEDF-BH, and proteins derived therefrom. The phrase "equivalent proteins" is intended to encompass all of these amino acid sequences.

Some examples of possible equivalent nucleic acids and equivalent proteins include nucleic acids with substitutions, additions, or deletions which direct the synthesis of the PEDF and PEDF-BH proteins and equivalent proteins; nucleic acids with different regulatory sequences that direct the production of the PEDF and PEDF-BH proteins; variants of PEDF-BH which possess different amino acids and/or a number of amino acids other than four fused to the amino terminal end of the protein; and PEDF and PEDF-BH proteins with amino acid substitutions, additions, deletions, modifications, and/or posttranslational modifications, such as glycosylations, that do not adversely affect activity.

The present invention also provides a vector which comprises a nucleic acid of SEQ ID NO:1, a nucleic acid which encodes a protein comprising the amino acid sequence of SEQ ID NO:2 or an equivalent protein, a nucleic acid which encodes a protein comprising the amino acid sequence of SEQ ID NO:3 or an equivalent protein, and equivalent nucleic acids thereof.

A. Cloning of the PEDF cDNA

Oligonucleotides are constructed from the sequence derived for the isolated polypeptide of PEDF on an ABI 392 DNA/RNA Synthesizer or by methods well known in the art.

The oligonucleotides are used as primers for a polymerase chain reaction (PCR) by using a Techne thermal cycler and standard reagents and methodologies, supplied under the trade name "GeneAMP" by Perkin-Elmer/Cetus of Emeryville, Calif.

A human fetal eye Charon BS cDNA library is screened by PCR techniques using a Techne thermal cycler and standard reagents and methodologies. The cDNA fragment generated by the reaction is isolated on a 3% w/v NuSieve 3:1 gel (FMC Biochemicals) using NA-45 DEAE-cellulose paper (Schleicher and Schull) as described by Sambrook et al., 1989 In: *Molecular Cloning: A Laboratory Manual* 2nd ed. Cold Spring Harbor Press, Cold Spring Harbor, N.Y. Briefly, the screening procedure is performed by taking about 1, 5 and 50 μl aliquots of the library and placing them in 600 μl siliconized reaction tubes and then bringing them to a final volume of about 74 μl with double-distilled sterile water. The phage particles are disrupted by incubation at about 70° C. for about 5 minutes and then cooling on wet ice.

PCR master mix is made up in a 600 μl reaction tube for 3 reaction tubes as follows:
- 30 μl of 10×Taq polymerase buffer;
- 24 μl of dNTP mix; and an appropriate volume of double-distilled water is added to bring the master mix to a final volume of about 78 μl.

The final solution, therefore, comprises about 192 mM KCl, 38.5 mM Tris-HCl, pH 8.3, 51.8 mM $MgCl_2$, 0.038% w/v gelatin, 0.77 mM of each dNTP, and 3.8 μl of each oligonucleotide primer. About 26 μl of master mix is added to each reaction tube. The library aliquots and the master mix solutions are overlayed with about 100 μl of mineral oil and heated to about 94° C. for about 5 minutes. The solutions are then equilibrated to the desired primer annealing temperature.

After the solutions have been equilibrated to the desired primer annealing temperature, about 1.5 μl of Taq polymerase is added to the solution and incubated for about 20 minutes. Thermal cycling is continued by incubating: at about 72° C. for about 3 minutes for primer extension, however, this primer extension time may be varied if desired; at about 94° C. for about 1 minutes about 20 seconds to denature the extension product from the template; at about 37° C. for about 2 minutes to anneal the primers to a template; and at about 72° C. for about 3 minutes for primer extension. The "cycle" is the repeated for a total of about 25 to about 30 cycles. At the end of the last cycle, a final primer extension step, of about 7 minutes at 72° C. is added.

The fragment is labelled with $^{32}$P by random priming using a kit supplied under the trade name "Prime-It Random Primer Labeling Kit" supplied by Stratagene Inc., La Jolla, Calif. The labelled probe is used to screen about 200,000 plaque-forming units of the Charon BS cDNA library by methods well known in the art.

Positive clones are isolated, and the DNA purified, with reagents supplied under the trade name "Qiagen Maxi" by Qiagen Inc. of Studio City, Calif.

The inserts within the phage vector are excised with an appropriate restriction enzyme, circularized with T4 DNA ligase supplied by New England Biolabs of Beverly, Mass. and transformed into competent *E. coli* Sure cells supplied by Stratagene. The cells are then plated on ampicillin/5-bromo-4-chloro-3-indolyl-β-D-galactoside (X-gal) plates.

White colonies are selected and mini-prepped using a plasmid miniprep reagent supplied by Qiagen. Purified plasmids are digested to excise the insert, and the fragments are separated by gel electrophoresis to determine the size of the inserts. A clone with an appropriately-sized insert is then chosen for further investigation.

The cDNA's for mouse and bovine PEDF were obtained following similar procedures.

B. Cloning of the Genomic DNA Sequence

The cDNA insert is labeled ith α-$^{32}$P dCTP and used to screen two genomic DNA libraries: a cosmid library constructed from MboI partial digests of human placental DNA (Clonetech) and a human placental genomic library constructed in λ DASH II (Stratagene). Positively hybridizing clones are analyzed by Southern blot analysis. Two strongly hybridizing fragments: a 7.1 kb BamHI fragment from the cosmid clone and a 7.2 kb Not1 fragment from the λ DASH II clone are selected for subcloning and DNA sequencing.

In an alternative embodiment of the present invention, primers, designed from the internal coding region of the PEDF cDNA sequence are synthesized using an ABI 392 DNA/RNA synthesizer and used as primers in polymerase chain reaction (PCR) experiments. The primer sequences are as follows: primer 603:

5'-ACAAGCTGGC AGCGGCTGTC-3' (SEQ ID NO:9)

is located in SEQ ID NO:1 at 271-290; primer 604:

5'-CAGAGGTGCC ACAAAGCTGG-3' (SEQ ID NO:10)

is located on the antisense strand in SEQ ID NO:1 at 570-590; primer 605:

5'-CCAGCTTTGT GGCACCTCTG-3' (SEQ ID NO:11)

is located in SEQ ID NO:1 at 570-590; primer 606:

5'-CATCATGGGG ACCCTCACGG-3' (SEQ ID NO:12)

is located on the antisense strand in SEQ ID NO:1 at 829-848; primer 2213:

5'-AGGATGCAGG CCCTGGTGCT-3' (SEQ ID NO:13)

is located in SEQ ID NO:1 at 114-133; primer 2744:

5'-CCTCCTCCAC CAGCGCCCCT-3' (SEQ ID NO:14)

is located on the antisense strand in SEQ ID NO:1 at 224-244; primer 2238:

5'-ATGTCGGACC CTAAGGCTGT T-3' (SEQ ID NO:15)

is located in SEQ ID NO:1 at 846-866; primer 354:

5'-TGGGGACAGT GAGGACCGCC-3' (SEQ ID NO:16)

is located on the antisense strand in SEQ ID NO:1 at 1043-1062. The primer pairs 603:604 amplified a single 2 kb PCR product (jt108); 605:606 amplified a single 3.3 kb PCR product (jt109); 2213:2744 amplified a single 2.3 kb PCR product (jt115) and 2238:354 amplified a single 1.5 kb PCR product (jt116).

In an alternative embodiment of the present invention, two sets of primers JT10-UP01:JT10-DP01 corresponding to bases 6536-6559 of jt106 genomic sequence and 1590:1591 corresponding to bases 1-89 of SEQ ID NO:1 are used in PCR reactions to isolate P1 clones (Genome Systems). The primer sequences are as follows: primer JT10-UP01:

5'-GGTGTGCAAA TGTGTGCGCC TTAG-3' (SEQ ID NO:17)

is located in SEQ ID NO: 4 at 6536; primer JT10-DP01:

5'-GGGAGCTGCT TTACCTGTGG ATAC-3' (SEQ ID NO:18)

is located in SEQ ID NO: 4 at 7175; primer 1590:

5'-GGACGCTGGA TTAGAAGGCA GCAAA-3' (SEQ ID NO:19)

is located in SEQ ID NO: 1 at 1-25; and primer 1591:

5'-CCACACCCAG CCTAGTCCC-3' (SEQ ID NO:20)

is located in SEQ ID NO: 1 at 71-89.

Positive clones are screened by PCR and Southern blot analysis and isolated.

C. DNA Sequence Analysis

Sequence analysis is performed with an automated sequencer or by other techniques well known in the art.

6. Expression of the PEDF Gene in Recombinant Cells

Commercial or large-scale production of PEDF may be achieved by expression of the gene, after cloning into an appropriate vector, in a suitable host cell. One such suitable vector/host system is the baculovirus/insect cell systems.

In one embodiment of the present invention, the PEDF gene is cloned into a baculovirus transfer vector such as pAC373, described by Lithgow et al., *DNA and Cell Biology* 10 443-449 (1991); pVL941, described by Ghiasi et al., *Virology* 185 187-194 (1991); or other such baculovirus transfer vectors that are well known by those skilled in the art.

Generally, such vectors comprise the polyhedron promoter of the *Autographa californica* nuclear polyhedrosis virus (AcNPV), inserted into a transfer vector such as pAc373, described by Summers and Smith (A manual for baculovirus vector and insect cell culture procedures, Texas Agric. Exp. Station Bull. No. 1555). Recombinant plasmids are prepared by methods well known in the art, such as those described by Maniatis et al. In: *Molecular Cloning: A Laboratory Manual* 2nd ed., Cold Spring Harbor Laboratory, Cold Spring Harbor, N.Y. (1982).

The host cells, such as *S. frugiperda* (Sf9), are grown in TC100 medium supplied by GIBCO, supplemented with 10% v/v fetal calf serum. The Sf9 cells are co-transfected with purified infectious AcNPV DNA, about 1 μg, and about 50 μl of the recombinant DNA. Culture supernatants are harvested about 4 days after transfection. Recombinant viruses are identified by plaque hybridization or radiolabelling of the proteins produced.

The above description provides an example of the expression of the PEDF gene in a vector/host expression system. Other expression systems are known in the art; for example, *Saccharomyces cerevisiae* has been used in conjunction with a number of vectors such as those described by Silar et al., *Gene* 104 99-102 (1991), Dietrich et al., *Eur. J. Biochem.* 201 399-407 (1991), or Akiyoshi-Shibata et al., *DNA and Cell Biology* 10 613-612 (1991); recombinant vaccinia virus vectors in HeLa host cells such as those described by Nakano et al., *Gene* 105 173-178 (1991). Any such methods or other methods known in the art are suitable for use in the present invention for expression of the PEDF gene.

The PEDF gene may be expressed as a transported protein where the PEDF is isolated from the medium in which the recombinant expression host is grown, or may be expressed as an intracellular protein by deleting the leader or other peptides, in which case the PEDF is isolated from the host cells. The PEDF so isolated is then purified by the methods described above.

In another embodiment of the present invention the vector πFS17, ATCC Deposit No. PTA-2753, which comprises the nucleic acid of SEQ ID NO: 1, and the vector pEV-BH, which comprises a nucleic acid which encodes a protein comprising the amino acid sequence of SEQ ID NO: 3. It will be appreciated by those skilled in the art that the cDNA inserts described can be present in alternative vectors. For example, inserts can be in vectors of different nature, such as phages, viral capsids, plasmids, cosmids, phagemids, YACs, or even attached to the outside of a phage or viral capsid. The vectors can differ in host range, stability, replication, and maintenance. Moreover, the vectors can differ in the types of control exerted over cloned inserts. For example, vectors can place cloned inserts under the control of a different promoter, enhancer, or ribosome binding site, or even organize it as part of a transposon or mobile genetic element.

The present invention also provides a host cell into which a vector, which comprises a nucleic acid of SEQ ID NO:1, a nucleic acid which encodes a protein comprising the amino acid sequence of SEQ ID NO:2 or an equivalent protein, a nucleic acid which encodes a protein comprising the amino acid of SEQ ID NO:3 or an equivalent protein, or an equivalent nucleic acid thereof, has been introduced. In particular, the host cell may have the vector πFS17, which comprises the nucleic acid of SEQ ID NO:1, or the vector pEV-BH, which comprises a nucleic acid which encodes a protein comprising the amino acid sequence of SEQ ID NO:3.

The vectors of the present invention can be introduced into any suitable host cell, whether eukaryotic or prokaryotic. These host cells may differ in their preferred conditions for growth, their nutritive requirements, and their sensitivity to environmental agents. Any appropriate means of introducing the vectors into the host cells may be employed. In the case of prokaryotic cells, vector introduction may be accomplished, for example, by electroporation, transformation, transduction, conjugation, or mobilization. For eukaryotic cells, vectors may be introduced through the use of, for example, electroporation, transfection, infection, DNA coated microprojectiles, or protoplast fusion.

The form of the introduced nucleic acid may vary with the method used to introduce the vector into a host cell. For example, the nucleic acid may be closed circular, nicked, or linearized, depending upon whether the vector is to be maintained as an autonomously replicating element, integrated as provirus or prophage, transiently transfected, transiently infected as with a replication-disabled virus or phage, or stably introduced through single or double crossover recombination events.

The present invention also provides a method of producing PEDF, PEDF-BH, and equivalent proteins, which method comprises expressing the protein in a host cell. For example, a host cell into which has been introduced a vector which comprises a nucleic acid of SEQ ID NO:1, a nucleic acid which encodes a protein comprising the amino acid sequence of SEQ ID NO:2 or an equivalent protein, a nucleic acid which encodes a protein comprising the amino acid of SEQ ID NO:3 or an equivalent protein, or an equivalent nucleic acid thereof, may be cultured under suitable conditions to produce the desired protein. In particular, a host cell into which has been introduced the vector πFS17, which comprises the nucleic acid of SEQ ID NO:1, or the vector pEV-BH, which comprises a nucleic acid which encodes a protein comprising the amino acid sequence of SEQ ID NO:3, may be cultured under suitable conditions to produce the proteins comprising the amino acid sequences of SEQ ID NO:2 and SEQ ID NO:3, respectively.

The present invention also provides recombinantly produced PEDF, PEDF-BH, and equivalent proteins, which have been produced in accordance with the aforementioned present inventive method of culturing an appropriate host cell to produce the desired protein. The production of a protein such as PEDF by recombinant means enables the obtention of large quantities of the protein in a highly purified state, free from any disease-causing agents which may accompany the protein isolated or purified from a naturally occurring source organism, and obviates the need to use, for example, fetal tissue as a source for such a protein.

The provision of cDNA sequences in the present invention also enables the obtention of human genomic DNA sequences that encode PEDF or that have substantial sequence homology to PEDF-BH.

The obtention of genomic DNA sequences from cDNA sequences can be accomplished using standard techniques.

Recombinant PEDF, PEDF-BH, and equivalent proteins may be supplied as active agents to cells by a variety of means, including, for example, the introduction of nucleic acids, such as DNA or RNA, which encode the protein and may be accordingly transcribed and/or translated within the host cell, the addition of exogenous protein, and other suitable means of administration as are known to those skilled in the art. In whatever form in which supplied, the active agent can be used either alone or in combination with other active agents, using pharmaceutical compositions and formulations of the active agent which are appropriate to the method of administration. Pharmaceutically acceptable excipients, i.e., vehicles, adjuvants, carriers or diluents, are well-known to those who are skilled in the art, and are readily available. The choice of excipient will be determined in part by the particular compound, as well as by the particular method used to administer the compound. Accordingly, there is a wide variety of suitable formulations which can be prepared in the context of the present invention. However, pharmaceutically acceptable excipients not altering the neurotrophic activity of the recombinant protein are preferred.

7. Treatment with PEDF

A. Treatment of Tumors

PEDF is administered, alone or in conjunction with other clinical (such as surgical) procedures. PEDF is administered by intravitreal, subretinal, intravenous or intramuscular injection or injected or applied at sites of tumor growth. The PEDF may be administered alone or in conjunction with compounds, such as polylactic acid, which facilitate a slow, "time release" of the PEDF. Typically, about 0.01 to about 10 μg of PEDF at a concentration of about 1 to about 100 μg/ml in a physiologic saline solution or other buffered solution is administered per dose, and about 0 to about 10 doses are administered per day. When time-release compounds are included in the composition, they are used at a concentration of about 1 to about 100 μg/ml. Treatment is continued until cessation of tumor growth and/or tumor regression is observed.

Treatment with PEDF is effective for retinal tumors such as retinoblastoma, other neuronal tumors such as neuroblastoma, or tumors of non-neuronal origin. The treatment results in a cessation or reduction in the rate of cell division and a concomitant reduction in the rate of tumor growth, which in turn results in tumor regression.

B. Neurotrophic Treatment of Ocular Disease

PEDF is administered, alone or in conjunction with other clinical (such as surgical) procedures. PEDF is administered by intravitreal or subretinal injection. The PEDF may be administered alone or in conjunction with compounds such as polylactic acid which facilitate a slow, "time release" of the PEDF. Typically, about 0.01 to about 10 µg of PEDF at a concentration of about 1 to about 100 µg/ml in a physiologic saline solution or other buffered solution is administered per dose, and about 0 to about 10 doses are administered per day. When time-release compounds are included in the composition, they are used at a concentration of about 1 to about 100 µg/ml. Treatment is continued until the progress of the pathology is halted and/or reversed.

Treatment with PEDF is directed at diseases of the neural retina, retinal pigmented epithelium, and other ocular tissue. Treatment results in enhanced survival and well-being of the photoreceptors and other ocular cells, prolonging their functional life span and delaying the onset of impaired vision and ultimate blindness.

C. Neurotrophic Treatment of Neuronal Cell Pathology

PEDF is administered, alone or in conjunction with other clinical (such as surgical) procedures. PEDF is administered by intravenous or intramuscular injection or application or injection at the site of neuronal cell pathology. The PEDF may be administered alone or in conjunction with compounds such as polylactic acid which facilitate a slow, "time release" of the PEDF. Typically, about 0.01 to about 10 µg of PEDF at a concentration of about 1 to about 100 µg/ml in a physiologic saline solution or other buffered solution is administered per dose, and about 0 to about 10 doses are administered per day. When time-release compounds are included in the composition, they are used at a concentration of about 1 to about 100 µg/ml. Treatment is continued until nerve regeneration is completed.

Treatment with PEDF is directed at injuries to nerves and pathologies of cells. Treatment results in enhanced survival of nerve cells and promotion of neurite outgrowth and nerve regeneration.

D. Treatment of Conditions Related to Serine Proteinases

PEDF is a serine proteinase inhibitor. As such, it is effective in the treatment of conditions caused by serine proteinases or where a serine proteinase inhibitor would be advantageous. Serine proteinases include, but are not limited to, chymotrypsin, trypsin, subtilisin, elastin, thrombin, and plasmin. Therefore, PEDF is useful as: an anti-coagulant, an anti-thrombotic, an anti-microbial, an anti-fungal, an anti-parasitic, and a contraceptive; in cosmetic preparations as a proteinase inhibitor; as a weight-gain promoter; in treatments for elastosis, vascular disorders involving fibrinoid formation, coagulation disorders, arteriosclerosis, ischemia, arthroses diabetes, emphysema, arthritis, septic shock, lung diseases, excessive complement activation, ulcers, ulcerative colitis, pancreatitis, psoriasis, fibrinolytic disease, arthropathy, bone resorption, hypertension, congestive heart failure, cirrhosis, or allergy caused by proteases, as a dermatological agent for skin discoloration and age-related wrinkling.

For use as an anti-coagulant, an anti-thrombotic, an anti-microbial, an anti-parasitic, or a contraceptive, or in treatment of elastosis, vascular disorders involving fibrinoid formation, coagulation disorders, arteriosclerosis, ischemia, arthroses diabetes, emphysema, arthritis, septic shock, lung diseases, excessive complement activation, pancreatitis, psoriasis, fibrinolytic disease, arthropathy, bone resorption, hypertension, congestive heart failure, cirrhosis, or allergy caused by proteases, PEDF is administered by intravenous or intramuscular injection or site-directed injection or application. The PEDF may be administered alone or in conjunction with compounds such as polylactic acid which facilitate a slow "time release" of the PEDF. Typically, about 0.01 to about 10 µg of PEDF at a concentration of about 1 to about 100 µg/ml in a physiologic saline solution or other buffered solution are administered per dose, and about 0 to about 10 doses are administered per day. When time-release compounds are included in the composition, they are used at a concentration of about 1 to about 100 µg/ml. Treatment is continued until progress of the pathology is halted and/or reversed.

Treatment with PEDF is directed at injuries to nerves. Treatment results in promotion of neurite outgrowth and nerve regeneration.

For use in cosmetic preparations as a proteinase inhibitor, arthritis or elastosis PEDF is added to the preparations to a concentration of about 0.01 to about 100 µg/ml.

For use in treatment as a weight-gain promoter, ulcers, ulcerative colitis, or pancreatitis, PEDF may be administered orally at a concentration of about 0.01 to about 10 µg per kg of body weight per day.

For use as a treatment for conditions such as psoriasis, PEDF may be administered topically at a concentration of about 0.01 to about 100 µg/ml, formulated in a suitable carrier.

EXAMPLE 1

Establishment of RPE Cell Cultures

RPE cells were harvested from post-mortem human eyes, as described by Pfeffer et al., *J. Cell. Physiol.* 117 333-341 (1983). The cells were grown in 75 cm flasks with Eagles's minimal essential medium supplemented with 15% v/v fetal calf serum and 5% v/v $CO_2$ at 37° C. Cells were grown to confluence, harvested by trypsinizing the cell monolayer, and resuspended in MEM supplemented with 15% v/v fetal calf serum. A portion of the cells (about 5%) were reseeded into new 75 cm, where the cells were again grown in 5% v/v $CO_2$ at 37° C.

EXAMPLE 2

Preparation of RPE-Conditioned Medium

Confluent cultures of RPE cells were washed extensively with HBSS, before conditioning, to remove serum proteins. Twenty-five ml of serum-free MEM was added, and the cultures were incubated with 5% v/v $CO_2$ at 37° C. for about 48 hours. The conditioned medium was then collected and centrifuged at 1,000 rpm at room temperature, to remove any free cells and other particulate matter, to provide an impure PEDF protein fraction.

EXAMPLE 3

Purification of PEDF by SDS Gel Electrophoresis

Proteins contained in human fetal RPE-conditioned medium, prepared as described in Example 2, and in control non-conditioned medium were analyzed on an SDS-polyacrylamide slab gel.

The conditioned and non-conditioned media samples were mixed with an electrophoresis sample buffer (62.5 mM Tris, pH 6.8, 2% w/v SDS, 10% v/v glycerol, 0.001% w/v bromophenol blue, and 0.1 M 2-mercaptoethanol). Molecular-weight markers, such as phosphorylase B, bovine serum albumin, ovalbumin, carbonic anhydrase, soybean trypsin inhibitor and lysozyme (such as that supplied by Bio-Rad), were also mixed with an electrophoresis sample buffer. All the samples were denatured at 100° C., in a boiling water bath, for 5 minutes and loaded onto a SDS containing 7.5% w/v polyacrylamide gel. The electrophoresis was conducted at 20 mA until the bromphenol blue marker dye migrated to the bottom of the gel.

At the completion of electrophoresis, strips from each outside edge of the gels, which included the markers and a lane each of conditioned and non-conditioned media, were stained with Coomassie blue. The stained protein bands which developed on the stained strips were used to align with the unstained portion of the gel, to locate the proteins present in conditioned medium but absent from non-conditioned medium.

The about 50,000 to about 55,000 molecular-weight PEDF protein doublet, unique to RPE-CM, were excised, and the proteins were electro-eluted from the unstained portion of the gel. A strip of the same gel excised from the region containing bovine serum albumin was treated similarly to serve as a control. The eluant was centrifuged to remove gel fragments, and the supernatant was dialyzed and analyzed by gel electrophoresis to assess its purity.

The electrophoretic patterns of human fetal RPE-CM and non-conditioned control medium show the presence of the prominent about 50,000 to about 55,000 molecular-weight PEDF doublet unique to the conditioned medium.

EXAMPLE 4

Small Scale Ammonium Sulfate Precipitation

An impure PEDF protein fraction, prepared as described in Example 2, was divided into six 10 ml aliquots. One of the aliquots was brought to 40% saturation, at 20° C., by the addition of 2.42 g of ammonium sulfate; another aliquot was brought to 50% saturation, at 20° C., by the addition of 3.14 g of ammonium sulfate; another aliquot was brought to 60% saturation, at 20° C., by the addition of 3.90 g of ammonium sulfate; another aliquot was brought to 70% saturation, at 20° C., by the addition of 4.72 g of ammonium sulfate; another aliquot was brought to 80% saturation, at 20° C., by the addition of 5.61 g of ammonium sulfate; and the final aliquot was brought to 90% saturation, at 20° C., by the addition of 6.57 g of ammonium sulfate. The aliquots were mixed until the ammonium sulfate was completely dissolved. The precipitates which formed in each of the tubes were collected by centrifugation at 10,000 rpm for 20 minutes. The precipitates were each resuspended in 10 mM sodium phosphate buffer, pH 7.5, and dialyzed against 2 l of 10 mM sodium phosphate buffer, pH 7.5, for 24 hours.

The samples were then collected and subjected to SDS-polyacrylamide gel electrophoresis on a 10% w/v SDS-polyacrylamide gel, as described in Example 3.

The results are summarized in Table I.

TABLE I

| % Saturation Ammonium Sulfate | Relative concentration of PEDF |
|---|---|
| 40 | − |
| 50 | − |

TABLE I-continued

| % Saturation Ammonium Sulfate | Relative concentration of PEDF |
|---|---|
| 60 | + |
| 70 | +++ |
| 80 | − |
| 90 | − |

The results indicate that the PEDF precipitates with an ammonium sulfate saturation of 60% to 70%. The small amount of PEDF in the 50% to 60% sample indicates that some PEDF is present, and that a suitable ammonium sulfate "cut" is from 50% to 70% saturation. The samples were subjected to SDS-polyacrylamide gel electrophoresis, as described in Example 3. It was estimated that the purity of the PEDF in the 60% to 70% ammonium sulfate fraction was about 50%.

EXAMPLE 5

Ammonium Sulfate Precipitation

An impure protein fraction, prepared as described in Example 2, was brought to 50% saturation with ammonium sulfate by the addition of 313 g/l of solid ammonium sulfate. The ammonium sulfate was added slowly to the impure protein fraction while the solution was stirred with a stir bar on a mechanical stirrer. After all the ammonium sulfate was added, the 50% ammonium sulfate solution was stirred for 30 minutes at 20° C. The 50% ammonium sulfate solution was then centrifuged at 10,000 g, at 20° C. for 20 minutes. The supernatant was collected.

The 50% ammonium sulfate solution was then brought to 70% saturation by the addition of 137 g/l of ammonium sulfate. The ammonium sulfate was added slowly, and after all the ammonium sulfate was added, the 70% ammonium sulfate solution was stirred for 30 minutes at 20° C. The 70% ammonium sulfate solution was centrifuged or filtered, as described above, and the precipitate was collected.

The ammonium sulfate precipitate was then redissolved in 10 mM sodium phosphate, pH 7, to form a 50%-70% ammonium sulphate fraction, then diafiltered using an Amicon Diaflo ultrafiltration unit, or dialyzed against 10 mM sodium phosphate, pH 7, to remove the ammonium sulfate from the redissolved 50-70% fraction.

The samples were subjected to SDS-polyacrylamide gel electrophoresis, as described in Example 3. It was estimated that the purity of the PEDF in the 50% to 70% ammonium sulfate fraction was about 50%.

EXAMPLE 6

Purification of PEDF by Cation Exchange HPLC

RPE-CM, prepared as described in Example 2, was dialyzed against 10 mM sodium phosphate buffer, pH 6.5, to remove media and salts from the impure protein sample. The dialyzed PEDF sample was then loaded onto a Brownlee Aquapore CX-300 HPLC chromatography medium, packed into a 4.6×30 mm column. The chromatography medium was previously equilibrated with 10 mM phosphate, pH 6.5. The dialyzed RPE-CM was loaded onto the chromatography medium, and the chromatography medium, with PEDF, was washed with 10 mM phosphate, pH 6.5, until all unbound proteins were washed from the chromatography medium.

PEDF was eluted from the chromatography medium with a linear salt gradient from 0.0 to 0.5 M NaCl in 10 mM phosphate, pH 6.5. PEDF, eluted with a NaCl concentration of 0.25 M.

The eluted PEDF was concentrated by lyophilization and resolubilized in 10 mM phosphate, pH 6.5. The eluted PEDF was analyzed by SDS gel electrophoresis, as described in Example 3. The eluted PEDF was estimated to be approximately 70% pure.

EXAMPLE 7

Purification of PEDF by Cation-Exchange HPLC

Ammonium sulfate-precipitated RPE-CM, prepared as described in Example 5, was dialyzed against 10 mM sodium phosphate buffer, pH 6.5, to remove ammonium sulfate. An 80 μl sample of the dialyzed ammonium sulfate-purified PEDF protein fraction was loaded onto a Brownlee Aquapore CX-300 chromatography medium, packed into a 4.6×30 mm column. The chromatography medium was previously equilibrated with 10 mM phosphate, pH 7.2. The PEDF/chromatography medium was washed with 10 mM sodium phosphate buffer, pH 7.2, until all unbound proteins were washed from the chromatography medium. PEDF was eluted from the chromatography medium with a linear salt gradient from 0.0 to 0.5 M NaCl in 10 mM sodium phosphate buffer, pH 7.2. PEDF eluted as a single peak with a NaCl concentration of about 0.25 M.

The eluted PEDF was dialyzed against 10 mM sodium phosphate buffer, pH 7.2, lyophilized, and resolubilized in water. The sample was then subjected to SDS-polyacrylamide gel electrophoresis, as described in Example 3.

The eluted PEDF was estimated to be about 70% pure.

EXAMPLE 8

Purification of PEDF by Reverse-Phase HPLC

Ammonium sulfate-precipitated RPE-CM, prepared as described in Example 5, was dialyzed against 10 mM sodium phosphate buffer, pH 6.5, to remove ammonium sulfate. An 80 μl PEDF-containing sample was then loaded onto a Vydac C8 chromatography medium, packed into a 4.6×250 mm column. The chromatography medium was previously equilibrated with 0.1 v/v TFA in water. The PEDF/chromatography medium was washed with 0.1% v/v TFA in water until all unbound proteins were washed from the chromatography medium. PEDF was eluted from the chromatography medium with a linear gradient from 0.0 to 95% v/v CH$_3$CN, 0.1% v/v TFA in water, and 5% v/v H$_2$O.

The eluted PEDF was dialyzed against 10 mM sodium phosphate buffer, pH 7.2, lyophilized, and resolubilized in water. The sample was then subjected to SDS-polyacrylamide gel electrophoresis, as described in Example 3.

The PEDF eluted from the column was estimated to be about 80% pure.

EXAMPLE 9

Purification of PEDF by Reverse-Phase HPLC

A PEDF-containing sample, partially purified as described in Example 2, was then loaded onto a Vydac C8 chromatography medium, packed into a 4.6×250 mm column. The chromatography medium was previously equilibrated with 0.1% v/v TFA in water. The PEDF/chromatography medium was washed with 0.1% v/v TFA in water until all unbound proteins were washed from the chromatography medium. PEDF was eluted from the chromatography medium with a linear gradient from 0.0 to 95% v/v CH$_3$CN in 0.1% v/v TFA and 5% v/v H$_2$O.

The eluted PEDF was dialyzed against 10 mM sodium phosphate buffer, pH 7.2, lyophilized, and resolubilized in water. The sample was then subjected to SDS-polyacrylamide gel electrophoresis, as described in Example 3.

The PEDF eluted from the column was estimated to be about 60% pure.

EXAMPLE 10

Purification of PEDF by Reverse-Phase HPLC

A PEDF-containing sample, partially purified as described in Example 6, was then loaded onto a Vydac C8 chromatography medium, packed into a 4.6×250 mm column. The chromatography medium was previously equilibrated with 0.1% v/v TFA in water. The PEDF/chromatography medium was washed with 0.1% v/v TFA in water until all unbound proteins were washed from the chromatography medium. PEDF was eluted from the chromatography medium with a linear gradient from 0.0 to 95% v/v CH$_3$CN in 0.1% v/v TFA and 5% v/v H$_2$O.

The eluted PEDF was dialyzed against 10 mM sodium phosphate buffer, pH 7.2, lyophilized, and resolubilized in water. The sample was then subjected to SDS-polyacrylamide gel electrophoresis, as described in Example 3.

The PEDF eluted from the column was estimated to be about 80% pure.

EXAMPLE 11

Purification of PEDF by Reverse-Phase HPLC

A PEDF-containing sample, prepared as described in Example 6, was loaded onto Brownlee RP-300 chromatography medium, packed into a 4.6×250 mm column. The chromatography medium was previously equilibrated with 0.1% v/v TFA in water. The PEDF/chromatography medium was washed with 0.1% v/v TFA in water until all unbound proteins were washed from the chromatography medium. PEDF was eluted from the chromatography medium with a linear gradient from 0.0 to 95% v/v CH$_3$CN in 0.1% v/v TFA and 5% v/v H$_2$O.

The eluted PEDF was dialyzed against 10 mM sodium phosphate buffer, pH 7.2, lyophilized, and resolubilized in water. The sample was then subjected to SDS-polyacrylamide gel electrophoresis, as described in Example 3.

The PEDF eluted from the column was estimated to be about 90% pure.

EXAMPLE 12

Purification of PEDF by Size-Exclusion Chromatography

Partially-purified PEDF, prepared as described in Example 5 or 6, was purified further by chromatography on Bio-Rad TSK-250 chromatography medium, packed into a 7.5×300 mm column. A 40 μl sample of resolubilized PEDF was loaded onto the size-exclusion chromatography medium, which had been previously equilibrated with 20 mM Tris, pH 7.0, 0.6 M NaCl. PEDF was eluted with 20 mM Tris, pH 7.0, 0.6 M NaCl.

The eluted PEDF was dialyzed against 10 mM sodium phosphate buffer, pH 7.2, lyophilized, and resolubilized in water. The sample was then subjected to SDS-polyacrylamide gel electrophoresis, as described in Example 3.

The PEDF eluted from the column was estimated to be about 75% pure.

EXAMPLE 13

Anion-Exchange Chromatography

DEAE cellulose is equilibrated with 10 mM Tris, pH 7.5. PEDF, prepared as described in Example 5, is applied to the column, and the column is washed with 10 mM Tris, pH 7.5, until all unbound proteins are eluted from the column. After all the unbound proteins are eluted, the PEDF is eluted with a linear gradient from 0 to 1 M NaCl in 10 mM Tris-HCl, pH 7.5. The fractions containing PEDF are collected and pooled. These fractions are then diafiltered against 10 mM Tris-HCl, pH 7.5 to remove NaCl.

EXAMPLE 14

Anion-Exchange Chromatography

DEAE cellulose is equilibrated with 10 mM Tris, pH 7.5. PEDF, prepared as described in Example 2, is applied to the column, and the column is washed with 10 mM Tris, pH 7.5, until all unbound proteins are eluted from the column. After all the unbound proteins are eluted, the PEDF is eluted with a linear gradient from 0 to 1 M NaCl in 10 mM Tris-HCl, pH 7.5. The fractions containing PEDF are collected and pooled. These fractions are then diafiltered against 10 mM Tris-HCl, pH 7.5 to remove NaCl.

EXAMPLE 15

Cation-Exchange Chromatography

Bio-Rex 70 resin (Bio-Rad) cellulose is equilibrated with 10 mM PBS, pH 7.2. PEDF, prepared as described in Example 2, is applied to the column, and the column is washed with 10 mM PBS, pH 7.2, until all unbound proteins are eluted from the column. After all the unbound proteins are eluted, the PEDF is eluted with a linear gradient from 0 to 1 M NaCl in 10 mM PBS, pH 7.2. The fractions containing PEDF are collected and pooled. These fractions are then diafiltered against 10 mM Tris-HCl, pH 7.5 to remove NaCl.

EXAMPLE 16

Cation-Exchange Chromatography

Bio-Rex 70 resin (Bio-Rad) cellulose is equilibrated with 10 mM PBS, pH 7.2. PEDF, prepared as described in Example 5, is applied to the column, and the column is washed with 10 mM PBS, pH 7.2, until all unbound proteins are eluted from the column. After all the unbound proteins are eluted, the PEDF is eluted with a linear gradient from 0 to 1 M NaCl in 10 mM PBS, pH 7.2. The fractions containing PEDF are collected and pooled. These fractions are then diafiltered against 10 mM Tris-HCl, pH 7.5 to remove NaCl.

EXAMPLE 17

Heparin Chromatography

Two ml of heparin agarose was packed into a 0.7×10 cm column, washed with 20 ml of 10 mM Tris-HCl, pH 7.5, 3 M NaCl, then equilibrated with 20 ml of 10 mM Tris-HCl, pH 7.5. Twelve ml of a PEDF solution, prepared as described in Example 2, from a 17-year-old human donor, was dialyzed against 4 l of 10 mM sodium phosphate buffer, pH 7.5, at 4° C. for 19 hours. The volume after dialysis was 19 ml. The dialysate was applied to the heparin agarose at a flow rate of 0.4 ml/minutes. After the PEDF solution had been applied to the heparin agarose, the heparin agarose was washed with 20 ml of 10 mM Tris-HCl, pH 7.5, to remove unbound proteins from the heparin agarose. PEDF was then eluted from the heparin agarose with 12 ml of 10 mM Tris-HCl, pH 7.5, 3 M NaCl.

The eluate containing PEDF was dialyzed against 10 mM Tris-HCl, pH 7.5, to remove the NaCl present in the eluate. The dialyzed eluate was then lyophilized, redissolved in 10 mM sodium phosphate buffer, pH 7.5, and a sample was subjected to 12.5% w/v SDS-polyacrylamide gel electrophoresis, as described in Example 3.

The PEDF eluate was estimated to be about 60% pure.

EXAMPLE 18

Heparin Chromatography

Two ml of heparin agarose was packed into a 0.7×10 cm column, washed with 20 ml of 10 mM Tris-HCl, pH 7.5, 3 M NaCl, then equilibrated with 20 ml of 10 mM Tris-HCl, pH 7.5. One ml of a PEDF solution, prepared as described in Example 5, was dialyzed against 4 l of 10 mM sodium phosphate buffer, pH 7.5, at 4° C. for 19 hours. The volume of the dialysate was 1.3 ml. The dialysate was applied to the heparin agarose at a flow rate of 0.4 ml/minutes. After the PEDF solution had been applied to the heparin agarose, the heparin agarose was washed with 20 ml of 10 mM Tris-HCl, pH 7.5, to remove unbound proteins from the heparin agarose. The heparin agarose was then successively eluted with 12 ml of 10 mM Tris-HCl, pH 7.5, 0.5 M NaCl; 12 ml of 10 mM Tris-HCl, pH 7.5, 1 M NaCl; 12 ml of 10 mM Tris-HCl, pH 7.5, 2 M NaCl; and 12 ml of 10 mM Tris-HCl, pH 7.5, 3 M NaCl.

Each of the eluates was dialyzed against 10 mM Tris-HCl, pH 7.5, to remove the NaCl present in the eluate. The dialyzed eluates were then lyophilized and redissolved in 10 mM sodium phosphate buffer, pH 7.5, and a sample of each dialyzed eluate was subjected to 12.5% w/v SDS-polyacrylamide gel electrophoresis, as described in Example 3.

The PEDF eluate was estimated to be about 70% pure.

EXAMPLE 19

Neuronal Inductivity and Differentiation Activity of Isolated PEDF

Electro-eluted PEDF was prepared as described in Example 3. To characterize the neuronal inductive activity of the isolated PEDF, the optimal concentration and pre-seeding stimulatory periods were determined. Either 1, 2, 4, 6, 8, or 10 µg/ml of electro-eluted PEDF in serum-free DME, supplemented with 1 mM sodium pyruvate, 0.625 mM HEPES, 6 mM L-glutamine, 1% w/v non-essential amino acids, 5 µg/ml insulin, 5 µg/ml transferrin, and 5 ng/ml selenous acid, was tested. As a control, RPE-CM, diluted with an equal volume of non-conditioned medium (50% RPE-CM), was also used.

The Y79 RB cells were grown in suspension culture. The cells were harvested by centrifugation for 5 minutes at 900 rpm at room temperature and resuspended in serum-free DME medium, which had previously been warmed to 37° C. The cells were collected by centrifugation and resuspended at a concentration of $10^6$ cells/ml in serum-free DME medium. One, 2, 4, 6, 8, or 10 µg/ml electro-eluted PEDF or 50% RPE-CM was introduced into separate Y79 RB cell cultures. The cells were incubated for 7 days at 37° C., and were then attached to poly-D-lysine-coated flasks. The cells were observed daily by phase-contrast microscopy.

The optimal pre-seeding period required for maximal inductive activity of PEDF was assessed by treating Y79 RB cell cultures with 2 µg/ml of electro-eluted PEDF for 2, 4, 8, or 16 days prior to seeding onto a poly-D-lysine substratum. In addition, 1 or 2 µg/ml of electro-eluted PEDF was added to attached cultures of cells not previously stimulated in suspension culture.

Greater than 80% of Y79 cell aggregates treated with 2 µg/ml electro-eluted PEDF extended arborizing processes within 8-10 days after attachment to a poly-D-lysine substratum; untreated cells showed only minimal signs of neuronal differentiation.

Y79 cells exhibited maximal differentiative response to electro-eluted PEDF at a protein concentration of 2 µg/ml; the response was reduced at concentrations exceeding 4 µg/ml. The results are shown in Table II.

TABLE II

| PEDF (µg/ml) | Pre-Attachment Stimulatory Period (days) | Percent Differentiated Cells |
| --- | --- | --- |
| 0 | 7 | 13 ± 8[1] |
| 1 | 7 | 82 ± 10 |
| 2 | 7 | 80 ± 10 |
| 4 | 7 | 33 ± 10 |
| 6 | 7 | 5 ± 5 |
| 8 | 7 | 0 |
| 10 | 7 | 0 |
| 1 | 0[2] | 20 ± 14 |
| 2 | 0[2] | 28 ± 11 |
| 1 µg/ml BSA[3] (control) | 7 | 8 ± 6 |

[1]Standard error
[2]PEDF added to non-stimulated attached cells, 24 hours post-seeding
[3]bovine serum albumin A pre-seeding stimulatory period (in suspension culture) of 8 days, in the presence of this factor, results in maximal differentiation of Y79 cells at day 10 post-attachment. Decreased frequencies of differentiation (less than 50%) are noted with both shorter and longer pre-seeding inductive periods. In addition, cells not previously stimulated with PEDF prior to attachment, exhibit a low frequency of neuronal differentiation (approximately 20%) if 1-2 µg/ml electro-eluted protein is added post-attachment. This response, however, is relatively slow, i.e., less than 15 days. Control BSA-treated cultures exhibit less than 10% differentiation, comparable to cells exposed only to non-conditioned media.

PEDF induced a high degree of neuronal differentiation in human retinoblastoma cells. Long ramifying neuritic processes were induced to extend from aggregates of stimulated cells; concomitant increases in the expression of the neuronal marker molecules, neuron-specific enolase, and the 200,000 molecular weight neurofilament protein were also observed. The expression of the neuronal phenotype in Y79 cells appears to involve three sequential events: 1) stimulation of cells in suspension culture by PEDF; 2) attachment of stimulated cells to a substratum; followed by 3) neurite outgrowth of attached, stimulated cells. Since only 20% differentiation was observed when non-stimulated, attached cultures were treated with PEDF, commitment to neuronal differentiation in Y79 cells appears to precede cell attachment and neurite outgrowth and may be initiated during the stimulatory period.

EXAMPLE 20

Comparison of the Effects of RPE-CM from Different Species

Cell cultures were established as described in Example 1, except the eyes from which the cells were derived were either fetal humans, adult humans, adult rats, fetal rats, or embryonic chickens.

RPE-CM was prepared from each of the cell cultures, as described in Example 2. Fetal human cell cultures which were newly established (short-term cultures) and cultures which had been established for 6 months (long-term cultures) were included.

The differentiation activity of the conditioned media was performed as described in Example 19.

The results of experiments monitoring the effects of RPE-CM from various species are summarized in Table III.

TABLE III

| Source of RPE-Conditioned Medium Aggregates | % Differentiated |
| --- | --- |
| Human (fetal, short-term cultures) | 88 ± 3* |
| Human (fetal, long-term cultures) | 50 ± 8 |
| Human (adult) | 55 ± 9 |
| Rat (adult) | 20 ± 11 |
| Rat (fetal) | 42 ± 7 |
| Chicken (embryonic) | 86 ± 7 |

*Standard error

The table summarizes the inductive activity of a variety of RPE-conditioned media on Y79 cells. Indicated are the percentages of 10 days attached aggregates (more than 5 cells/aggregate) exhibiting neurite outgrowth after 7 days' stimulation with 50% v/v RPE-CM from the various species. One hundred aggregates were counted from each sample in replicates of three.

The greatest differentiative response in Y79 cells is induced by human fetal RPE-CM (short-term cultures) and embryonic chicken RPE-CM, both of which induce neuronal differentiation in greater than 80% of cellular aggregates when used at a 50% v/v concentration. In contrast, decreased frequencies (less than 50%) of cellular differentiation are noted for conditioned media from long-term (12-18 months) cultures of human fetal RPE and adult human RPE. Only 40% neuron-like differentiation is induced by fetal rat RPE-CM and 20% by adult rat RPE-CM.

Conditioned media from human fetal and embryonic chicken RPE cells contain similar neurotrophic activity, while those from adult cultures (chicken and rat) and long-term cultures of human fetal RPE-CM are less effective in promoting the neuronal phenotype in Y79 cells. It is possible that mature RPE cells no longer secrete this neurotrophic factor, or they secrete reduced quantities which are less effective in the culture conditions utilized. The fact that some trophic activity is seen in RPE-conditioned media from other species suggests that PEDF, or a similar factor, is also secreted by RPE cells of other species and may be generally important to normal retinal development and function.

EXAMPLE 21

Two-Dimensional Gel Electrophoresis

Two-dimensional gel analysis was conducted by the method described by O=Farrell, *J. Biol. Chem.* 250 4007-4021 (1975) and Jones, *J. Exp. Med* 14b 1251-1279 (1977). Silver-staining was performed using a Bio-Rad silver-stain plus kit. Twenty µg of PEDF, purified by cation-exchange and size-exclusion HPLC, was loaded onto the IEF tube gel.

Two-dimensional electrophoretic analysis of HPLC-purified PEDF reveals the presence of four closely-grouped molecular species. The four species vary slightly in apparent molecular weight, but all are in the 50,000 molecular-weight region of the gel, consistent with the previously identified molecular weight of PEDF. The resolved species also vary slightly in isoelectric point, suggesting slight variations in post-translational modifications. Amino-acid sequence analysis (see Example 22), however, indicated the presence of only a single polypeptide.

EXAMPLE 22

Isolation of PEDF Specific Peptides and Amino-Acid Sequences

One-hundred-and-eighty µg of purified PEDF (purified as described in Examples 2, 6, and 12) was concentrated using a Centricon 10 microconcentrator, supplied by Amicon of Danvers, Mass., and then diluted in 25 mM Tris, pH 8.5, 1 mM EDTA. To the protein sample was added endoproteinase Lys-C. The PEDF/proteinase mixture was incubated for about 18 hours at 30° C. to digest the PEDF.

The resulting PEDF polypeptide fragments were separated using by HPLC on a Vydac C8 reverse-phase HPLC packed into a 4.6×250 mm column. The column was equilibrated with 0.1% v/v TFA in water. The polypeptides were eluted with 90% v/v CH$_3$CN, 0.1% v/v TFA in water.

Polypeptides eluted from the column which are well separated from other polypeptides were collected and subjected to protein sequencing analysis. The amino-acid sequence analysis was performed under contract at the Microsequencing Facility of Beckman Research Institute at the City of Hope.

The amino-acid sequences for the isolated polypeptides were determined to be:
PEDF-13 (SEQ ID NO:2, residues 226-244)
Thr Ser Leu Glu Asp Phe Tyr Leu Asp Glu Glu Arg Thr Val Arg Val Pro Met Met (SEC ID NO:21)
PEDF-14 (SEQ ID NO: 2, residues 161-186) Ser Tyr Gly Thr Arg Pro Arg Val Leu Thr Gly Asn Pro Arg Leu Asp Leu Gln Glu Ile Asn Asn Trp Val Gln Ala (SEQ ID NO:22)

Sequencing of PEDF-13 yielded 19 residues of unequivocal sequence. PEDF-14 yielded 26 residues, 25 of which were unequivocal. The identification of residue 23 in PEDF-14 as tryptophan was not absolutely certain.

EXAMPLE 23

Isolation of PEDF Specific Peptides and Amino Acid Sequence

PEDF, purified as described in Examples 2, 6, and 12, was reduced and alkylated. The sample was dried, redissolved in 50 µl of CRA buffer (8 M urea, 0.4 M ammonium bicarbonate, pH 8.0), and 5 µl of 45 mM DTT (Calbiochem) was added. After heating at 50° C. for 15 minutes, the solution was cooled, and 5 µl of 100 mM iodoacetic acid (Sigma Chemical Co.) was added. After 15 minutes, the solution was diluted to a concentration of 2 M urea and subjected to trypsin digestion, supplied by Boehringer-Mannheim, using an enzyme: substrate ratio of 1:25 (wt/wt), for 22 hours at 37° C.

Tryptic peptides were separated by narrow-bore reverse-phase HPLC on a Hewlett-Packard 1090 HPLC, equipped with a 1040 diode array detector, using a Vydac 2.1 mm×150 mm C18 column. Buffer A was 0.06% v/v trifluoroacetic acid/H$_2$O, and buffer B was 0.055% v/v trifluoroacetic acid/ acetonitrile, a gradient of 5% v/v B at 0 minutes, 33% v/v B at 63 minutes, 60% v/v B at 95 minutes, and 80% v/v B at 105 minutes, with a flow rate of 150 µl/minutes, was used. Chromatographic data at 210, 277 nm and UV spectra from 209 to 321 nm of each peak were obtained.

Samples for amino terminal sequence analysis were applied to a polybrene pre-cycled glass fibre filter and subjected to automated Edman degradation at the Harvard Microchemical Facility in Boston, Mass., on an ABI model 477A gas-phase protein sequencer using program NORMAL 1. The resulting phenylthiohydantoin amino acid fractions were manually identified using an on-line ABI Model 120A HPLC and Shimadzu CR4A integrator.

The sequences of the isolated peptides were determined to be:
(SEQ ID No:2 residues 54-67)
Leu Ala Ala Ala Val Ser Asn Phe Gly Tyr Asp Leu Tyr Arg (SEO ID NO:23)
(SEQ ID NO:2 residues 107-135) Ala Leu Tyr Tyr Asp Leu Ile Ser Ser Pro
Asp Ile His Gly Thr Tyr Lys Glu Leu Leu Asp Thr Val Thr Ala Pro Gln Lys Asn (SEQ ID NO:24)
(SEQ ID NO:2 residues 307-316)
Thr Val Gln Ala Val Leu Thr Val Pro Lys (SEQ ID NO:25)
(SEQ ID NO:2 residues 317-327) Leu Lys Leu Ser Tyr Glu Gly Glu Val Thr (SEO ID NO:26)
Lys
(SEQ ID NO:2 residues 360-389) Ala Gly Phe Glu Trp Asn Glu Asp Gly Ala Gly Thr Thr Pro Ser Pro Gly Leu Gln Pro Ala His Leu Thr Phe Pro Leu Asp Tyr His (SEO ID NO:27)

EXAMPLE 24

Comparison of the PEDF Peptides to Rat Serine Proteinase Sequences

PEDF-13 shows significant sequence homology with serpin proteinase molecules. Homologous molecules include rat serine protease inhibitors 1 and 2, a rat hepatocyte growth hormone-regulated protein, a rat thyroid hormone-regulated protein, and mouse contrapsin. Human, monkey, sheep, and mouse alpha-1 antitrypsin, and porcine alpha-1-antichymotrypsin, show significant but somewhat less homology. PEDF-14 shows homology with different protease inhibitors, but the degree of homology is less than that observed for PEDF-13. These include human plasma protease C1 inhibitor and human alpha-2-antiplasmin inhibitor. These results suggest that PEDF may function as a protease inhibitor, but that it is molecularly distinct from such inhibitors which have been described previously.

PEDF shows significant homology with serpins, the family of serine protease inhibitors that share a common reactive center near the C-terminal end, which serves as an exposed binding site that acts as bait for target serine proteinases. It is of interest that a number of known members of the serpin family have been shown to have neurotrophic effects on a variety of neuronal cell types. For example, glial-derived nexin (GDN) promotes neurite outgrowth in neuroblastoma cells, as do a number of other protease inhibitors, such as hirudin and leupeptin. Protease inhibitors also stimulate neuronal differentiation in cells of dorsal root ganglia, sympathetic neurons, and hippocampal pyramidal neurons. It is also of interest that the production of proteinases and protease inhibitors is stimulated by a number of known growth factors. While it remains to be determined if PEDF has protease inhibitor activity, it is likely, since inhibitory activity has been shown to be necessary for the neurite-promoting activity of glial derived nexin. It has been suggested that the formation of a stable protease-GDN complex, and a consequent conformational change in GDN and/or the associated protease, is necessary for the neurite-promoting activity of GDN. PEDF may well function similarly, as there are known proteinases present in the interphotoreceptor matrix and in the developing neural retina.

EXAMPLE 25

Cloning of the PEDF cDNA A6

The following oligonucleotides were constructed:
5'-AGYAAYTTYT AYGAYCTSTA-3' (SEQ ID NO:28)

determined in Example 22, and:
5'-CTYTCYTCRT CSAGRTARAA-3' (SEQ ID NO:29)

determined in Example 23.

The oligonucleotides were prepared on an ABI 392 DNA/RNA Synthesizer and used as primers in a polymerase chain reaction (PCR). A human fetal eye Charon BS cDNA library, donated by Dr. A. Swaroop, was amplified once by the method described by Sambrook et al., 1989 In: *Molecular Cloning: A Laboratory Manual* 2nd ed. Cold Spring Harbor Press, Cold Spring Harbor, N.Y. and screened by PCR as described by Friedman et al. (Screening of λgt 11 libraries In: *PCR Protocols: A Guide to Methods and Applications* Innis, Gelfand, Sninsky and White, eds., Academic Press, pp. 253-260, 1990) using a Techne thermal cycler and standard reagents (GeneAMP, Perkin-Elmer/Cetus), except that $MgSO_4$ was used at 3 mM.

The recovered fragment was isolated on a 3% w/v NuSieve 3:1 gel (FMC Biochemicals, Rockland Me.) using NA-45 DEAE-cellulose paper (Schleicher and Schull) and labelled with $^{32}P$-dCTP (Amersham Corp., Arlington Heights, Ill.) by random priming (Random Priming kit, Boehringer-Mannheim, Indianapolis, Ind.; Prime-It Random Primer Labeling Kit, Stratagene).

This probe was used to screen 200,000 pfu's of the same library. Positive clones were isolated as described by Sambrook et al., 1989 In: *Molecular Cloning: A Laboratory Manual* 2nd ed. Cold Spring Harbor Press, Cold Spring Harbor, N.Y., and the DNA was purified with Qiagen Maxi preparation protocols (Qiagen).

The inserts were cut out with NotI (BRL, Gaithersburg, Md.) circularized with T4 DNA ligase (New England Biolabs, Beverly, Mass.), transformed into competent *E. coli* Epicurian Sure cells (Stratagene), and plated out on 12.5 µg/ml ampicillin/40 µg/ml X-gal agar plates.

White colonies were selected and mini-prepped (Qiagen plasmid mini-prep protocol). Purified plasmids were digested with EcoRI/HindIII (BRL). These restriction sites were added during library construction through the ligation of linkers to the 5' and 3' ends of the insert, thus EcoRI-HindIII digestion excises the insert present in isolated plasmids.

These fragments were electrophoresed on a 0.7% w/v agarose gel to determine insert size. The plasmid possessing the largest insert, namely πFS17, was selected for mapping and subsequent sequencing using the Sequenase 2.0 sequencing kit (United States Biochemical Corp., Cleveland, Ohio) to confirm the identity of the clone. Sequence analysis was performed using the MacVector software package (International Biotechnologies, Inc.) and the GenBank® Sequence Data Bank (Intelligenetics, Mountain View, Calif.).

EXAMPLE 26 cDNA Sequence Analysis of Human PEDF

One of the identified clones which contained an insert corresponding to the PEDF gene was selected for mapping and subsequent sequencing using a USB Sequenase 2.0 protocol and reagents.

Sequence analysis of πFS17 revealed a base sequence comprising SEQ ID NO:1, with a long, open reading frame (ORF) encoding the 418 amino acids of SEQ ID NO:2, a typical ATG start codon, and a polyadenylation signal (not shown in SEQ ID NO:1). The coding sequence of the clone aligns exactly with all previously determined PEDF peptide sequences. The deduced amino acid sequence also contains a stretch of hydrophobic amino acids that could serve as a signal peptide. A comparison of the coding sequence and peptide sequence with the GenBank® Data Bank indicates that PEDF is a unique protein having significant homology to the serpin (serine antiprotease) gene family, which includes human [α]-1-antitrypsin. Although some of the members of this gene family exhibit neurotrophic activity (Monard et al., *Prog. Brain Res.* 58 359-364, 1983); Monard, *TINS* 11 541-544, 1988), PEDF lacks homology to the proposed consensus sequence for the serpin reactive domain.

EXAMPLE 27 cDNA Sequence Analysis of Mouse PEDF

An isolated cDNA incorporating the mouse cDNA was sequenced. The sequence covering the first 376 amino acids is presented in SEQ ID NO:7.

EXAMPLE 28 cDNA Sequence Analysis of Bovine PEDF

An isolated cDNA incorporating the bovine cDNA was sequenced. The sequence is presented in SEQ ID NO:8.

EXAMPLE 29

Construction of an Expression Vector for the Production of Recombinant PEDF-BH

An expression vector was constructed using the plasmid πFS17, which contains the full-length cDNA for human PEDF as described in Example 25. The PEDF coding sequence was placed under the control of a bacteriophage λ $P_L$ promoter present in the plasmid pEV-vrf2 (Crowl et al., *Gene* 38 31-38, 1985) to obtain the vector pEV-BH. This was accomplished by obtaining a BamHI-HindIII fragment of πFS17 comprising a portion of the PEDF coding region (namely, nucleotides 245 to 1490 of SEQ ID NO:1), digesting plasmid pEV-vrf2 with EcoRI-HindIII, rendering both fragments blunt by means of a fill-in reaction at the BamHI and EcoRI ends with DNA polymerase I (Klenow fragment), and ligating the resultant blunt-ended/compatible-ended fragments to each other. The resultant vector pEV-BH places a distance of 8 nucleotides between the Shine-Dalgarno (SD) sequence and the PEDF coding region. The construct specifies Met-Asn-Arg-Ile-Asp$^{44}$ - - - Pro$^{418}$ such that a protein of 379 amino acids, known as PEDF-BH, is encoded as indicated in SEQ ID NO:3. The amino acids at the amino terminus of the PEDF-BH protein do not occur in native PEDF and result from the fusion of nucleic acids during the construction of pEV-BH.

To verify production of the recombinant PEDF-BH protein by pEV-BH, the plasmid was propagated in *E. coli* strain RRI (Maniatis et al., *Molecular Cloning: A Laboratory Manual*, Cold Spring Harbor Laboratory, Cold Spring Harbor, N.Y., 1982), bearing the low copy-number compatible plasmid pRK248cIts that contains a gene for encoding a temperature-sensitive λcIAt2 repressor (Bernard et al., *Methods in Enzymology* 68 482-492, 1979). Protein induction was performed as described in Becerra et al., *Biochem.* 30 11707-11719 (1991), with the following modifications. Bacterial cells containing pEV-BH were grown in LB medium containing 50 μg/ml ampicillin at 32° C. to early logarithmic phase, such that $OD_{600 \, nm}$=0.2. The temperature of the culture was rapidly increased to 42° C. by incubating the flask in a 65° C. water bath, and the bacteria were subsequently grown at 42° C. for 2-3 hours in an air-flow incubator at 340 rpm. Aliquots were taken for absorbance readings at 600 nm.

Nascent proteins, synthesized following protein induction, were radiolabeled. After the temperature of the culture had reached 42° C., 150 μCi of L-[$^{35}$S]methionine (1040 Ci/mmol, Amersham Corp., Arlington Heights, Ill.) were added per ml of culture, and incubation was continued at 42° C. for 10 minutes and 30 minutes. Cells were harvested by centrifugation and washed with TEN buffer (10 mM Tris-HCl, pH 7.5, 1 mM EDTA, and 100 mM NaCl). $^{35}$S-labeled peptides from total bacterial extracts were resolved and analyzed on SDS-12% w/v PAGE followed by fluorography. A band corresponding to a 42,820 $M_r$ polypeptide was detected 10 and 30 minutes post-induction. The size obtained for the recombinant protein expressed by pEV-BH matched the expected size for the coding sequence subcloned in pEV-BH.

EXAMPLE 30

Construction of Expression Vectors Containing the Full-Length PEDF cDNA.

In a manner similar to that described in Example 27 for the construction of pEV-BH, the PEDF ORF of plasmid πFS17 was placed under the control of the bacteriophage λ $P_L$ promoter present in the plasmids pRC23 and pEV-vrf1 (Crowl et al., *Gene* 38 31-38, 1985). This was accomplished by obtaining the SfaNI-HindIII fragment of πFS17 comprising a portion of the PEDF cDNA (namely, nucleotides 107 to 1490 of SEQ ID NO:1), digesting the plasmids with EcoRI-HindIII, rendering the fragments blunt by means of a fill-in reaction at the SfaNI and EcoRI ends with DNA polymerase I (Klenow fragment), and ligating the resultant blunt-ended/compatible-ended fragments to each other. The resulting vectors PRC-SH and pEV-SH place a distance of 14 and 8 nucleotides, respectively, between the SD sequence and the PEDF coding region. The construct pRC-SH encompasses the full-length PEDF ORF, and specifies a PEDF protein of 418 amino acids, with its naturally occurring amino terminus, as set forth in SEQ ID NO:2. The construct pEV-SH encompasses the full-length PEDF ORF, and specifies a PEDF amino-terminal fusion protein of 425 amino acids, with Met-Asn-Glu-Leu-Gly-Pro-Arg (SEQ ID NO:4) preceding the PEDF sequence of SEQ ID NO:2. These additional amino acids at the amino terminus do not occur in native PEDF, and the codons in pEV-SH specifying these additional amino acids result from the fusion of nucleic acids during the construction of pEV-SH.

To verify production of the recombinant proteins specified by the two vectors, the vectors were introduced into *E. coli* strain RRI [pRK248cIts], and protein induction was performed and monitored by metabolic labeling with $^{35}$S-methionine during induction in a manner similar to that set forth in Example 27. The induced expression of the proteins specified by pRC-SH and pEV-SH had a negative effect on bacterial cell growth. In comparison with bacterial cultures containing the parental plasmids, cultures containing pRC-SH and pEV-SH grew and divided more slowly. This negative effect on bacterial growth correlated with the distance between the initiation codon and the SD, which may suggest that a shorter such distance results in more efficient translation of the recombinant protein. A 46,000 $M_r$ candidate polypeptide for PEDF was not detected in the media or cell lysates of bacterial cultures containing pRC-SH and pEV-SH. However, a 35,000 $M_r$ protein was observed in extracts of cultures containing PRC-SH and pEV-SH, but not in extracts of cultures containing parental plasmids. This may indicate that the amino-terminal end of PEDF is protease-sensitive and that recombinant full-length PEDF is metabolized in this particular host. Alternatively, failure to observe the anticipated-sized recombinant PEDF proteins may reflect an experimental artifact which could be overcome through the use of alternative expression vectors, hosts, inducible promoters, subcloning sites, methods of recombinant protein isolation or detection, or means of protein induction.

EXAMPLE 31

Method for Producing Large Quantities of Recombinantly Produced PEDF-BH.

A total of 1 g of *E. coli* cells containing PEDF-BH was resuspended in 50 ml 20 mM Tris-HCl, pH 7.5, 20% w/v sucrose, and 1 mM EDTA. The cells were maintained on ice for 10 minutes, sedimented by centrifugation at 4,000×g, and were resuspended in 50 ml of ice-cold water for 10 minutes. Lysed outer cell walls were separated from spheroplasts by centrifugation at 8,000×g.

The pelleted spheroplasts were resuspended in 10 ml of phosphate buffered saline (PBS) containing 5 mM EDTA, 1 μg/ml pepstatin and 20 μg/ml aprotinin. The suspension was probe-sonicated with a sonicator (Ultrasonics, Inc., model W-225) to lyse the cell membranes. Three bursts at 30 second pulses with a 30 second pause were performed while the sample was immersed in an ice-water bath. RNase TI (1,300 units, BRL) and DNase I (500 μg, BRL) were added to the sonicated cell suspension, and the suspension was incubated at room temperature for 10 minutes. This suspension was diluted by the addition of 40 ml of phosphate buffered saline (PBS) containing 5 mM EDTA, 1 μg/ml pepstatin and 20 μg/ml aprotinin, and the crude inclusion bodies were sedimented by centrifugation at 13,000×g for 30 minutes. The particulate material consisting of inclusion bodies was resuspended in 40 ml of PBS containing 25% w/v sucrose, 5 mM EDTA, and 1% v/v Triton X-100, incubated on ice for 10 minutes, and centrifuged at 24,000×g for 10 minutes. The washing step was repeated three times. Finally, the inclusion bodies were resuspended in 10 ml of denaturation buffer containing 50 mM Tris-HCl, pH 8.0, 5 M guanidine-HCl, and 5 mM EDTA. The suspension was probe-sonicated briefly for 5 seconds in an ice-water bath. The resulting suspension was incubated on ice for an additional hour. After centrifugation at 12,000×g for 30 minutes, the supernatant was added to 100 ml of renaturation buffer containing 50 mM Tris-HCl, pH 8.0, 20% v/v glycerol, 1 mM DTT, 1 μg/ml pepstatin, and 20 μg/ml aprotinin, and stirred gently at 4° C. overnight to renature the protein. The soluble and insoluble fractions were separated by centrifugation at 13,500×g for 30 minutes.

The soluble fraction was further purified by concentrating it to 1 ml using a Centricon 30 microconcentrator (Amicon Div., W. R. Grace & Co., Beverly, Mass.), and dialyzing it against Buffer A (50 mM sodium phosphate, 1 mM DTT, 20% v/v glycerol, 1 mM EDTA, 1 μg/ml pepstatin, and 1 mM benzamidine) at 4° C. for 3 hours. The dialyzed extract was centrifuged at 14,000 rpm in an Eppendorf Centrifuge (Model 5415C) for ten minutes. The supernatant fraction was layered on a S-Sepharose fast-flow (Pharmacia, New Market, N.J.) medium packed into a column with a 1 ml bed volume and pre-equilibrated with buffer A. The medium was washed with two column-volumes of buffer A. Finally, recombinant PEDF-BH was eluted with a step gradient of 50, 100, 150, 200, 300, 400, 500, and 1,000 mM NaCl in buffer A. Fractions of 1 ml were collected by gravity flow, and were dialyzed against buffer A. The 300 mM NaCl fraction, containing recombinant PEDF-BH, was stored at −20° C. The recovery in fraction 300 was 50 μg per gram of packed cells, which represents 25% of the total protein.

Most of the PEDF-BH was recovered from the insoluble fraction by dissolving the fraction in 10 ml of 6M guanidinium-HCl in buffer B (50 mM Tris-HCl, pH 8.0, 1 mM DTT, 2 mM EDTA). The solution was centrifuged at 10,000×g for 5 minutes. The supernatant was layered onto a SUPEROSE-12 (Pharmacia, New Market, N.J.) medium packed into a column attached in tandem to a second SUPEROSE-12 medium containing column (each column 2.6 cm×95 cm) pre-equilibrated with buffer containing 4 M guanidinium-HCl in buffer B. The flow rate was 3 ml/minute. Recombinant PEDF-BH containing fractions from the SUPEROSE-12 column were pooled and dialyzed against buffer C (4 M urea, 50 mM sodium phosphate, pH 6.5, 1 mM benzamidine, 1 μg/ml pepstatin, 4 mM EDTA). The dialyzed fraction was passed through a 0.22 μm filter (Miller-GV, Millipore Corp., Bedford, Mass.). The filtered solution was layered onto a MONO-S (Pharmacia, New Market, N.J.) medium packed into a column (1 cm×10 cm, d×h) and pre-equilibrated with buffer C. The medium was washed with buffer C, and recombinant PEDF-BH was eluted with a gradient of 0-500 mM NaCl in buffer C at 0.5 ml/minutes. Two-ml fractions were collected, and the peak fractions of recombinant PEDF-BH were pooled. The recovery in the pooled fractions was 0.5 mg of recombinant PEDF-BH per gram of packed cells.

EXAMPLE 32

Use of Purified Recombinant PEDF-BH as a Differentiation Agent

Y79 cells (ATCC, HTB18) were grown in Eagle's Minimal Essential Medium with Earl's salts (MEM) supplemented with 15% v/v fetal bovine serum and antibiotics (10,000 u/ml penicillin and 10 mg/ml streptomycin) at 37° C. in a humidified incubator under 5% v/v $CO_2$. Cells were propagated for two passages after receipt from the ATCC, and then frozen in the same medium containing 10% v/v DMSO. A few of the frozen aliquots were used for each differentiation experiment. All experiments were performed in duplicate.

After thawing, the cells were kept, without further passaging, in the serum-containing medium until the appropriate number of cells were available. Cells were collected by centrifugation and washed twofold in PBS, resuspended in PBS, and counted. At that point, $2.5 \times 10^5$ cells were plated into each well of a 6-well plate (Nunc, Inc., Roskilde, Denmark) with 2 ml of serum-free medium (MEM, supplemented with 1 mM sodium pyruvate, 10 mM HEPES, 1×non-essential amino acids, 1 mM L-glutamine, 0.1% v/v ITS mix (5 μg/ml insulin, 5 μg/ml transferrin, 5 μng/ml selenium, Collaborative Research, Bedford, Mass.), and antibiotics as described above.

Differentiation effectors and control buffers were added 12-16 hours after plating, and the cultures were incubated and left undisturbed for 7 days. On the eighth day, cells were transferred to poly-D-lysine-coated six-well plates (Collaborative Research, Bedford, Mass.), and the old medium was replaced with 2 ml of fresh serum-free medium, upon attachment of the cells to the substrate. The cultures were maintained under these conditions for up to 11 days. Post-attachment cultures were examined daily for morphological evidence of differentiation as well as quantification of neurite outgrowth using an Olympus CK2 phase-contrast microscope.

In comparison with untreated cells, only Y79 cultures that were exposed to recombinant PEDF-BH showed any significant evidence of neuronal differentiation. Some neurite outgrowth (below 10%) was detectable in control cultures treated with the same buffer used to solubilize PEDF-BH, and no evidence of differentiation was found in cultures processed in the same manner without the addition of PEDF-BH or buffer. Phase contrast microscopy of PEDF-BH treated cultures showed that between 50-65% of the cell aggregates had neurite extensions by day 3 post-attachment on poly-D-lysine. These 3-day neurite extensions appeared as short projections from pear-shaped cells at the edges of the cell aggregates. The number of differentiating aggregates, the number of differentiating cells per aggregate, and the length of the neurite-like processes increased with post-attachment time. By day 5 post-attachment, about 75-85% of the aggregates showed signs of differentiation with neurites extending from most of their peripheral cells. PEDF-BH-treated cultures reached the maximum extent of differentiation on day 7 post-attachment, when 85-95% of the cells aggregate. At that time, two types of neuronal processes were observed, i.e., single neurites 2-3 fold longer than those observed on day 3 extending from peripheral cells of isolated aggregates, and much longer and thinner processes forming a branching network between neighbor cell aggregates. Upon extended incubation, i.e., beyond 10 days post-attachment, there was a marked decrease in the proportion of the network connections, and no further growth of the single neurites, although the viability of the cell aggregates was not severely affected, and remained at about 75-80% in different experiments.

The PEDF and PEDF-BH cDNA clones not only provide means to produce large quantities of the PEDF and PEDF-BH proteins but also serve as sources for probes that can be used to study the expression and regulation of the PEDF gene. In addition, these sequences can be used in the antisense technique of translation arrest to inhibit the translation of endogenous PEDF.

The recombinantly produced PEDF and PEDF-BH proteins and equivalent proteins can be used as potent neurotrophic agents in vitro and in vivo. Additional biochemical activities of these proteins as neurotrophic agents can be determined through standard in vitro tests, which will enable the development of other therapeutic uses for these proteins in the treatment of inflammatory, vascular, degenerative and dystrophic diseases of the retina. Given that these proteins are such potent neurotrophic agents, it can be envisioned that these proteins could be modified for therapeutic utility in the treatment of tissues other than the retina, which also respond to neurotrophic factors. These proteins may even find more generic utility as "differentiation" factors for non-neural tissues and certain types of cancer.

EXAMPLE 33

Treatment of Retinal Tumors

PEDF is administered, alone or in conjunction with clinical (such as surgical) procedures. PEDF is administered by intravitreal or subretinal injection. The PEDF may be administered alone or in conjunction with compounds such as poly (lactic acid) which facilitate a slow, "time release" of the PEDF. Typically, 0.01 to 10 µg of PEDF at a concentration of 1 to 100 µg/ml in a physiologic saline solution or other buffered solution is administered per dose, and 0 to 10 doses are administered per day. When time-release compounds are included in the composition, they are used at a concentration of 1 to 100 µg/ml. Treatment is continued until tumor progression is halted or reversed.

Treatment with PEDF is effective for retinal tumors such as retinoblastoma, other neuronal tumors such as neuroblastoma, or tumors of non-neuronal origin. The treatment results in a cessation or reduction in the rate of cell division and a concomitant reduction in the rate of tumor growth, which in turn results in tumor regression.

EXAMPLE 34

Neurotrophic Treatment of Ocular Disease

PEDF is administered, alone or in conjunction with clinical (such as surgical) procedures. PEDF is administered by intravitreal or subretinal injection. The PEDF may be administered alone or in conjunction with compounds such as poly (lactic acid) which facilitate a slow, "time release" of the PEDF. Typically, 0.01 to 10 µg of PEDF at a concentration of 1 to 100 µg/ml in a physiologic saline solution or other buffered solution is administered per dose, and 0 to 10 doses are administered per day. When time-release compounds are included in the composition, they are used at a concentration of 1 to 100 µg/ml. Treatment is continued until the pathology is halted or reversed.

Treatment with PEDF is directed at diseases of the neural retina, retinal pigmented epithelium, and other ocular tissue. Treatment results in enhanced survival and well-being of the photoreceptors and other ocular cells, prolonging their functional life span and delaying the onset of impaired vision and ultimate blindness.

EXAMPLE 35

Neurotrophic Treatment of Injured Nerves

PEDF is administered, alone or in conjunction with clinical (such as surgical) procedures. PEDF is administered by intravitreal or subretinal injection. The PEDF may be administered alone or in conjunction with compounds such as poly (lactic acid) which facilitate a slow, "time release" of the PEDF. Typically, 0.01 to 10 µg of PEDF at a concentration of 1 to 100 µg/ml in a physiologic saline solution or other buffered solution is administered per dose, and 0 to 10 doses are administered per day. When time-release compounds are included in the composition, they are used at a concentration of 1 to 100 µg/ml. Treatment is continued until nerve regeneration is completed.

Treatment with PEDF is directed at injuries to nerves. Treatment results in promotion of neurite outgrowth and nerve regeneration.

EXAMPLE 36

Transfection of Bacterial Cells

Competent *E. coli* Sure cells are mixed with the ligation mixture and incubated on ice for 60 minutes. The mixture is then incubated at 42° C. for 2 minutes, then 800 µl of 2% w/v BACTO Tryptone, 2% w/v BACTO Yeast Extract (both supplied by DIFCO LABORATORIES), 10 mM NaCl, 10 mM $MgSO_4$, 20 mM glucose are added and the mixture incubated at 37° C. for 60 minutes. Fifty to 500 µl of the DNA mixtures are then spread on selection plates containing 12.5 µg/ml ampicillin.

The recombinant colonies are screened by miniprepping and digestion of the isolated DNA. Positive colonies containing the appropriate inserts are then prepared by growing the appropriate colony in 200 ml of Luria Broth plus 12.5 µg/ml ampicillin with shaking at 37° C. overnight. After the overnight incubation, the cultures are transferred to centrifuge bottles and centrifuged at 2500 rpm for 10 minutes. The supernatant is removed and the cells are resuspended in 30 ml of STET buffer (0.23 M sucrose, 5% v/v Triton-X-100, 20 mM EDTA, 50 nM Tris-HCl, pH 8) at room temperature. Five µl of 10 mg/ml lysozyme is added and the mixture is swirled and incubated for 5 minutes at room temperature. Each flask is then gently swirled directly over a flame until the cells begin to coagulate and turn white. The mixture is then transferred to a boiling-water bath for about 45 seconds. The solution is then cooled in an ice-water bath for 2 minutes, and the mixture is transferred to centrifuge tubes and centrifuged for 15 minutes at 16,000 rpm.

The supernatant is then transferred to a clean container. Two volumes of 100% ethanol are added, mixed, and the DNA precipitated at −70° C. for 20 minutes. The precipitate is collected by centrifugation at 2,500 g for 15 minutes. The ethanol supernatant is removed, and the pellet is washed with 10 ml of cold (−20° C.) 90% v/v ethanol. Two-and-one-half ml of extraction buffer (0.2 M Tris, pH 7.5, 0.08 M EDTA, and 0.2 M KCl) is added to the pellet, and it is resuspended, at 4° C. 100 µl of 10 mg/ml RNAse, dissolved in 0.1×TE (1 mM Tris-HCl, 0.1 mM EDTA, pH 7.6) and pretreated by boiling for 10 minutes.

EXAMPLE 37

Insect Cell Cultures

Sf9 cells are seeded into spinner flasks, containing Grace's Antheraea medium supplied by GIBCO of Grand Island, N.Y., to an initial density of $1 \times 10^6$ cells/ml and incubated at 27° C. with constant stirring at 50 rpm. The cells are subcultured when they reach a density of 2.5×10⁶ cells/ml, approximately 2 to 3 times a week, and are diluted 1 in 5.

EXAMPLE 38

Cloning Genes into pAC373

Two µl of pAC373 are combined with 25 µl of 10×BamHI restriction enzyme buffer, 20 units of BamHI and sterile distilled water to bring the volume to 250 µl, and incubated at 37° for at least 3 hours. After the plasmid is digested. It is dephosphorylated by adding one unit of calf intestinal alkaline phosphatase (CAP)/µg of DNA and incubated for 30 minutes at 37° C. The CAP is then inactivated by adding EDTA to 25 mM and SDS to 0.5% w/v and incubated at 65° C. for 15 minutes. The solution is then extracted with an equal volume of phenol/chloroform/ isoamyl alcohol (25:24:1).

The aqueous phase is collected, and 125 µl of 7.5 M ammonium acetate and 800 µl of 95% v/v ethanol are added and mixed. The DNA is precipitated at −70° C. for 10 minutes. The precipitate is then collected by centrifugation by centrifugation at 12,000 rpm for 10 minutes. The pellet is rinsed with (−20° C.) 90% v/v ethanol. The ethanol is then removed and the DNA is resuspended in 50 µl of 10 mM Tris-HCl, 1 mM EDTA, pH 7.6 (1×TE).

EXAMPLE 39

Ligation of PEDF to pAC373

A purified DNA fragment containing the PEDF gene is ligated to the transfer vector. Two-hundred ng of digested pAC373 are mixed with an equal molar concentration of PEDF containing fragment. Ligation buffer (50 mM Tris-HCl, pH 7.4, 10 mM MgCl₂, 10 mM dithiothreitol, 0.5 mM spermidine, 2 mM ATP, 2.5 mM hexamine cobalt chloride and 20 µg/ml BSA) and 10 units of T4 DNA ligase is added. Water is added to a total volume of 10 µl. The mixture is incubated at 14° C. for 3 hours.

EXAMPLE 40

Transferring Genes into the AcMNPV Genome

Sf9 cells are seeded into 25 cm flasks at a density of 2.0×10⁶ cells/flask in Grace's Antheraea medium. The cells are allowed to attach for at least one hour. One µg of MNPV DNA is added to 2 µg of plasmid DNA, which contains the PEDF gene. The medium is removed from the flask and replaced with 0.75 ml of Grace's medium plus 10% v/v fetal bovine serum and antibiotics (50 µg/ml gentamicin sulfate, 2.5 µg/ml amphotericin). 7.5 ml of transfection buffer (25 mM HEPES, pH 7.1, 140 mM NaCl, 125 mM CaCl₂) is added to the DNA solution and mixed. The DNA solution is added to the Grace's medium, already in the cell culture flasks.

Calcium phosphate precipitates form due to the calcium chloride in the transfection buffer and the phosphate in the medium. The flasks are incubated at 27° C. for 4 hours, after which time the medium is removed from the flasks, and the cells are rinsed with fresh TNM-FH (Grace's medium plus 3.3 g/l YEASTOLATE and 3.3 g/l Lactalbumin hydrolysate, both from DIFCO LABORATORIES) plus 10% v/v fetal bovine serum and antibiotics, as described previously, and 5 ml of TNM-FH plus 10% v/v fetal bovine and antibiotics, as described previously, is added to the cells. The cells are incubated for 4-6 days. When the infection is at an advanced stage, the virus is plated on fresh monolayers, and the recombinant viruses are plaque-purified.

EXAMPLE 41

Identification of Recombinant Proteins

Plaque-purified virus is screened by radiolabelling. The recombinant proteins are identified on SDS-PAGE gels. Sf9 cells are seeded at 6×10⁵ cells/well in a 24-well culture plate. The cells are allowed to attach for an hour. The medium is then removed and overlaid with medium containing the viral stock and incubated for 1 hour at 27° C., after which time the viral inoculum is removed and replaced with 500 µl of complete medium. The cells are incubated for 48 hours at 27° C. At the end of this incubation, the medium is removed. 200 µl of methionine-free Grace's medium is added to the cells, and the cells are incubated for 60 minutes, after which time the medium is replaced with 200 µl of fresh methionine-free Grace's medium to which 10 µCi of ³⁵S-methionine is added. Cells are incubated at 27° C. for 6 hours and then harvested by centrifugation. The supernatant is collected, and the cells are resuspended in 62.5 mM Tris, pH 6.8, 2% w/v SDS, 10% v/v glycerol, 0.001% w/v bromophenol blue, and 0.1 M 2-mercaptoethanol. An equal volume of 126 mM Tris, pH 6.8, 4% w/v SDS, 20% v/v glycerol, 0.002% w/v bromophenol blue, and 0.2 M 2-mercaptoethanol is added to the supernatant. Samples are then boiled for 3 minutes and then they are subjected to electrophoresis and autoradiography of the gel to identify proteins secreted into the medium and proteins that are not secreted. Controls of uninfected cells and cells infected with wild-type virus are included.

EXAMPLE 42

Chromosomal Localization of the PEDF Gene: Southern Hybridization

Human-hamster somatic cell hybrid DNAs were used to identify the chromosomal location of the PEDF gene. Twenty-five hybrids were characterized by karyotype analysis by the method described by Carlock et al. (*Somatic Cell Mol. Genet.* 12 163-174, 1986), and the chromosome content of current passages of each cell line was determined by Giemsa banding analysis of 20 metaphases. DNA samples were subjected to restriction fragment length analysis using a number of restriction enzymes to establish a polymorphism within the PEDF gene. RsaI was found to be suitable for such use. DNA samples were digested with RsaI, and 8 µg of each digested DNA sample was fractionated by electrophoresis in a 1% w/v agarose gel and transferred onto neutral nylon membranes (BIODYNE A sold by Pall Corp.).

Two 20-mer PCR primers were synthesized from the middle of the translated region of the PEDF cDNA sequence. The primer pair:

5'-CTGGGAGCGG ACGAGCGAAC-3' (SEQ ID NO:30)

located at SEQ ID NO:1 396-415 (primer 353) and

5'-TGGGGACAGT GAGGACCGCC-3' (SEQ ID NO:35)

located on the antisense strand of SEQ ID NO:1 at 1043-1062 (primer 354), amplifies a 667 bp product from the PEDF cDNA. PCR amplification was carried out for 30 cycles (each cycle: 94° C., 1 minute; 55° C., 1 minute; and 72° C., 1 minute) by methods well known to those skilled in the art. Fifty nanograms of the amplified product was labeled by random priming using a random PRIME-IT kit purchased from Stratagene. Unincorporated nucleotides were removed using Stratagene's Cloning Systems NUCTRAP PUSH columns. The nylon filters were prehybridized for 30 minute at 65° C. in the same solution supplemented with 1×106 cpm/ml radiolabeled PEDF probe, by methods well known to those skilled in the art. Posthybridization washes were performed for 30 minutes at 25° C. using 300 mM NaCl, 35 mM sodium citrate, pH 7.0, 0.1% w/v SDS (2×SSC/0.1% SDS) and 30 minute at 65° C. in 2×SSC/0.1% SDS. Filters were exposed to Hyperfilm-MP (Amersham, Ill.) with an intensifying screen.

Somatic cell hybrid DNAs were scored on Southern blots for the presence or absence of human-specific hybridization with the PEDF 667 bp PCR fragment. The PEDF cDNA probe identifies 6.5, 6.0, 5.0, and 4.8 kb human restriction fragments, as can be seen in the human genomic DNA control lanes in each blot. Of the 25 somatic cell hybrids examined, only 2 contained a PEDF-specific band of an approximate 5.0 kb molecular size. These hybrids are the only ones which contain human chromosome 17. A positive correlation therefore is observed between the presence of this band and human chromosome 17.

EXAMPLE 43

Chromosomal Localization of the PEDF Gene: PCR Assay

DNAs from human-rodent somatic cell hybrid panels (1 and 2) were purchased from the NIGMS Human Genetic Mutant Cell Repository at the Coriell Institute for Medical Research (Camden, N.J.). PCR and chromosomal localization studies (Sambrook et al., 1989 In: *Molecular Cloning: A Laboratory Manual* 2nd ed. Cold Spring Harbor Press, Cold Spring Harbor, N.Y.) were performed using primers 3 and 4 and hybrid DNAs from NIGMS panel 1. Primers 3 and 4 were designed from the 3' translated region of the PEDF cDNA using OLIGO primer analysis software (National Biosciences, Plymouth, Minn.). Primer 1 sequence:

5'-CACCTTAACC AGCCTTTATT C-3' (SEQ ID NO:31)

is located in SEQ ID NO:1 at 1281-1304 and primer 2 sequence:

5'-AACCTTACAG GGGCAGCCTT CG-3' (SEQ ID NO:32)

and is located on the antisense strand in SEQ ID NO:1 at 1438-1459, amplified a 179bp product from the PEDF cDNA and human genomic DNA. The PCR reaction contained 10 mM Tris-HCl, pH 8.3, 50 mM KCl, 80 μM of each dNTP, 1 mM MgCl$_2$, 200 ng of each primer, 100 ng of genomic DNA, and 1.25 units of AMPLITAQ (Perkin Elmer Cetus). Amplification was carried out for 40 cycles (each cycle consisting of 94° C., 1 minute; 57° C., 1 minute; and 72° C. for 2 minute).

For panel 2, two additional 24-mer PCR primers from the 3'-untranslated region of the PEDF cDNA were designed. Partial purification and desalting of this primer pair were accomplished by passing the oligonucleotide through SEPHADEX G-25 (Pharmacia, Upsala Sweden) packed into a column. Primer 498:

5'-TATCCCAGTT TAATATTCCA ATAC-3' (SEQ ID NO:33)

is located at SEQ ID NO:1 at 1374-1397 and primer 499:

5'-TTGTATGCAT TGAAACCTTA CAGG-3' (SEQ ID NO:34)

is located on the antisense strand of SEQ ID NO:1 at 1448-1472 defines a 99-bp domain in the 3' noncoding region of the human PEDF cDNA sequence. PCR was performed in a 100-μl reaction containing 10 mM Tris-HCl, pH 8.3, 50 mM KCl, 100 μM of each dNTP, 1.5 mM MgCl$_2$, 200 ng of genomic DNA from each hybrid, 200 ng of PEDF primers 5 and 6, and 1.25 units of AMPLITAQ (Perkin Elmer Cetus).

DNA was subjected to preamplification heating at 94° C. for 10 minute, after which amplification was carried out for 20 cycles. Each cycle consisted of 1 minute denaturation at 94° C., 1 minute annealing at 47° C., and 2 minute extension at 72° C. A final extension was carried out at 72° C. for 7 minute. One microliter of the amplified product was reamplified using the above procedure.

Using primers 3 and 4, a 179 bp product was amplified from human genomic DNA which was absent from hamster and mouse genomic DNA. In a human-rodent somatic cell hybrid panel (NIGMS MAP 1), the 179 bp product was observed in somatic hybrids 1-15, which contain a number of human chromosomes, including chromosome 17, but not in hybrids 16-18, which do not contain chromosome 17. A second panel, NIGMS MAP 2, also was investigated using PEDF primers 498 and 499, which yield a 99 bp product. Each hybrid of this panel contains only one human chromosome. Of the 24 hybrids tested, only GM/NA 10498 was positive and was the only one to contain human chromosome 17. Amplification was seen with human genomic DNA but not with mouse and hamster DNAs.

EXAMPLE 44

Chromosomal Localization of the PEDF Gene: Fluorescence in situ Hybridization (FISH)

A 7-kb fragment of the PEDF gene from a cosmid clone was prepared and purified using Quiagen plasmid protocol (Quiagen Inc., Chatsworth, Calif.) and digested with NotI (Gibco BRL, Gaithersburg, Md.), and the insert size was determined on a 0.5% w/v agarose gel. FISH was performed at Bios Laboratories after the PEDF probe was labeled by nick translation with dUTP digoxigenin as described by Lichter et al. (*Science* 247 64-69, 1990). A chromosome 17 centromeric-specific probe, D17Z1 (Oncor, Gaithersburg, Md.), which hybridizes to a 171 bp α-satellite tandem repeat, was used as a marker in a cohybridization study. The D17Z1 probe was nick translated and labeled with biotin-dATP, by methods well known in the art. The PEDF genomic DNA probe was detected using antidigoxigenin-fluorescein-conjugated F(ab) fragments; D17Z1 was detected with avidin-conjugated fluorescein-isothiocyanate (FITC). Chromosomes were counterstained with propidium iodide. Eight separate hybridizations were performed for each probe.

Fluorescence in situ hybridization analyses of eight metaphase chromosome spreads using a digoxigenin-labeled PEDF probe revealed that 50% of the cells demonstrated specific fluorescent signals on chromosome 17. The identity of the chromosome and its specificity were confirmed since the PEDF probe clearly cohybridized with D17Z1, a probe specific to α-satellite tandem repeats in the centromere of chromosome 17. Of importance as well is that, in each case, the genomic probe gave a specific hybridization signal at the terminal end of the short arm of chromosome 17 (region 13.1).

EXAMPLE 45

Subchromosomal Localization of the PEDF Gene: PCR Assay

DNAs from a deletion mapping panel of eight somatic cell hybrids containing different regions of human chromosome 17 (see Guzzetta et al., *Genomics* 13 551-559, 1992) were used to further sublocalize the PEDF gene. PCR conditions for panel 1 were used in this assay, including primers 3 and 4. Up to 600 ng of DNA for the chromosome 17 HO-11 hybrid was used in the PCR assay.

The use of human-rodent cell hybrids containing defined regions of chromosome 17 (see Guzzetta et al., *Genomics* 8 279-285, 1991; Guzzetta et al., *Genomics* 13 551-559, 1992) allows accurate subchromosomal localization of the PEDF gene. PCR primers 3 and 4, which yield a 179 bp product, again were used in this study. The PCR amplification product was seen with four of these hybrids: MH22-6 contains the entire chromosome; DHA-4 has a deletion in the p11.2 region; 88-H5 and 357-2D retain much of the p arm, including the 13.1 region. Two hybrids are seen to be negative: L(17n)C, which contains only 17q; and MH41, which has only the distal q arm. The hybrid 12.3B, however, which retains 17p and the proximal q region, is positive. Finally and of greatest significance, the hybrid HO-11, which is missing only the 17p13.1 to 17pter region, is negative. Together, these data localize the PEDF gene to 17p13.1-pter.

Additional experiments indicate that PEDF is located on chromosome 11 in mice. The mouse chromosome 11 is syntenic with human chromosome 17.

EXAMPLE 46

Expression Analysis: Northern Hybridization

RNA was extracted from human Y79 retinoblastoma cells. The cells were grown in suspension culture under the following three conditions: (A) medium (MEM, Mediatech) containing 15% v/v fetal bovine serum (Y79-control); (B) serum-free, defined medium (MEM, Y79-SF); (C) seruma-free, defined medium containing 5% v/v bovine soluble interphotoreceptor matrix components (Y79-IPM) as previously described by Tombran-Tink et al., *J. Comp. Neurol.* 317 175-186, 1992). Under a fourth condition (D), the cells were stimulated with 5% v/v bovine IPM for 1 week in suspension culture and then attached and allowed to differentiate for 10 days (differentiated Y79) as previously described (Tombran-Tink et al., *J. Comp. Neurol.* 317 175-186, 1992). Approximately 95% of these cells differentiate into a neuronal phenotype under this condition. Cells maintained under conditions A-C are morphologically undifferentiated clusters that remain in suspension. Cells under all four conditions were harvested at a total of 17 days in culture and poly(A)+ RNA extracted by the method of Sambrook et al. (1989 In: *Molecular Cloning: A Laboratory Manual* 2nd ed. Cold Spring Harbor Press, Cold Spring Harbor, N.Y.).

Human fetal RPE cells were kindly provided by Dr. Dean Bok (Jules Stein Institute, Univ of Cal., L.A.) These cells were obtained from 20- to 21-week-old donors and were cultured in SF-defined medium for 6 months prior to isolation of poly(A)+ RNA (Sambrook et al., 1989 In: *Molecular Cloning: A Laboratory Manual* 2nd ed. Cold Spring Harbor Press, Cold Spring Harbor, N.Y.). Two micrograms of poly(A)+ RNA from each sample was electrophoresed on a 1% v/v formaldehyde denaturing gel, transferred onto neutral nylon membrane, UV cross-linked, and hybridized with the PCR-amplified 667 bp PEDF cDNA probe, by methods well known to those skilled in the art. Hybridization procedures were similar to those used for Southern hybridization of somatic cell hybrid panels.

PEDF was originally detected as a secreted protein in the medium of human fetal retinal pigment epithelial (RPE) cells (Tombran-Tink et al., *Inves. Ophthalmol. Vis. Sci.* 53 411-414, 1989). These cells demonstrate a single 1.5-kb mRNA on Northern blots. Surprisingly, undifferentiated Y79 retinoblastoma cells demonstrate a 1.5-kb message even though little if any PEDF protein can be detected in the medium. Cells grown in suspension culture for 17 days with 15% v/v fetal bovine serum, SF-defined medium, and 5% v/v soluble components of the bovine interphotoreceptor matrix (IPM) all express the PEDF message at substantial but varying levels and all remain morphologically undifferentiated. In contrast, induction of a marked neuronal phenotype and total inhibition of PEDF message are seen in Y79 cells that were treated with soluble components of the bovine IPM for 1 week and then maintained in attachment culture for 10 additional days.

In addition Northern blots were performed using mRNA from a variety of human adult and fetal tissues, as described above. The results indicate that PEDF mRNA is present in retina, heart, brain, placenta, lung, liver, skeletal muscle, kidney, pancreas, thymus, prostate, testis, ovary, small intestine and colon. No significant mRNA was detected in adult kidney or spleen, however, PEDF is expressed in abundance in fetal kidney. The most abundant expression of PEDF is in liver, skeletal muscle, testis and ovary.

In brain tissue PEDF is expressed in the amygdala, caudate nucleus, corpus callosum, hippocampus, hypothalmus, substantia nigra, subthalmic nucleus, thalamus and pineal. By Western blots, PEDF is seen in RPE-CM from a number of species including humans, cow, monkey and chicken. Large quantities of PEDF can also be detected int he vitreaous humor of these vertebrates.

EXAMPLE 47

Isolation of Genomic Clones: Screening Genomic Libraries

Bluescript plasmid containing a 1.5 kb PEDF cDNA insert was digested with EcoRI and HindIII (BRL). Twenty-five ng of PEDF cDNA insert, purified by gel electrophoresis was labelled with $\alpha$-$^{32}$P dCTP (Amersham) by random priming (RANDOM PRIME IT kit from Stratagene). Unincorporated nucleotides were removed by Stratagene's NUC TRAP push columns. The labelled probe was used to screen two genomic DNA libraries: a cosmid library constructed from MboI partial digests of human placental DNA (Clonetech) and a human placental genomic library constructed in $\lambda$ DASH II (Stratagene). Positively hybridizing clones were isolated by standard methods (Troen *Methods in Enzymology* 151 426, 1987; Sambrook et al., 1989 In: *Molecular Cloning: A Laboratory Manual* 2nd ed. Cold Spring Harbor Press, Cold Spring Harbor, N.Y.) and the DNA purified with Qiagen maxi preparation protocols (Qiagen).

Southern blot analysis of the purified clones revealed the presence of two strongly hybridizing fragments: a 7.1 kb BamHI fragment from the cosmid clone and a 7.2 kb NotI fragment from the $\lambda$ DASH II clone. These were selected for subcloning in Bluescript and DNA sequencing.

EXAMPLE 48

Isolation of Genomic Clones: Cloning by PCR

Four sets of primers, designed from the internal coding region of the PEDF cDNA sequence were synthesized using an ABI 392 DNA/RNA synthesizer for use as primers in polymerase chain reaction (PCR) experiments. The primer sequences are as follows: primer 603:

5'-ACAAGCTGGC AGCGGCTGTC-3' (SEQ ID NO:36)

is located in SEQ ID NO:1 at 271-290; primer 604:

5'-CAGAGGTGCC ACAAAGCTGG-3' (SEQ ID NO:37)

is located on the antisense strand in SEQ ID NO:1 at 570-590; primer 605:

5'-CCAGCTTTGT GGCACCTCTG-3' (SEQ ID NO:38)

is located in SEQ ID NO:1 at 570-590; primer 606:

5'-CATCATGGGG ACCCTCACGG-3' (SEQ ID NO:39)

is located on the antisense strand in SEQ ID NO:1 at 829-848; primer 2213:

5'-AGGATGCAGG CCCTGGTGCT-3' (SEQ ID NO:40)

is located in SEQ ID NO:1 at 114-133; primer 2744:

5'-CCTCCTCCAC CAGCGCCCCT-3' (SEQ ID NO:41)

is located on the antisense strand in SEQ ID NO:1 at 224-244; primer 2238:

5'-ATGTCGGACC CTAAGGCTGT T-3' (SEQ ID NO:42)

is located in SEQ ID NO:1 at 846-866; primer 354:

5'-TGGGGACAGT GAGGACCGCC-3' (SEQ ID NO:43)

is located on the antisense strand in SEQ ID NO:1 at 1043-1062. Standard reagents (obtained from GeneAMP, Perkin-Elmer/Cetus of Norwalk, Conn.) and 500 ng of human genomic DNA obtained from peripheral blood lymphocytes were used. PCR reactions were carried out at a number of different annealing temperatures until only single amplified products were obtained. The primer pairs 603:604 amplified a single 2 kb PCR product (jt108); 605:606 amplified a single 3.3 kb PCR product (jt109); 2213:2744 amplified a single 2.3 kb PCR product (jt115) and 2238:354 amplified a single 1.5 kb PCR product (jt116).

Seven clones isolated either from genomic libraries or by PCR-mediated cloning were sequenced and used to characterize the exon structure of the PEDF gene and to define the intron/exon junction sequences. The conventional method of cloning was replaced by PCR-mediated cloning because of instability and rearrangement of the gene in both cosmid and λ genomic libraries.

Two positively hybridizing clones, jt101 (7.1 kb) and jt106 (7.2 kb) were isolated from a cosmid and λ DASHII genomic libraries respectively. Four clones of jt108 (2 kb), jt109 (3.3 kb), jt115 (2.3 kb) and jt116 (1.5 kb) represented PCR products of human genomic DNA. lr117 (6 kb) clone was obtained from an exon 1-labeled positively hybridizing BamHI fragment from human genomic and P147 DNA. Two P1 clones, P1-11 and P1-47 containing the entire PEDF gene were also isolated and intron/exon boundaries sequenced.

EXAMPLE 49

Isolation of Genomic Clones: Identification of P1 Clones

Two sets of primers JT10-UP01:JT10-DP01 corresponding to bases 6536-6559 of jt106 genomic sequence and 1590:1591 corresponding to bases 1-89 of SEQ ID NO:1 were used in PCR reactions to isolate P1 clones (Genome Systems). The primer sequences are as follows: primer Jt10-UP01:

5'-GGTGTGCAAA TGTGTGCGCC TTAG-3' (SEQ ID NO:44)

is located in SEQ ID NO: 4 at 6536; primer JT10-DP01:

5'-GGGAGCTGCT TTACCTGTGG ATAC-3' (SEQ ID NO:45)

is located in SEQ ID NO: 4 at 7175; primer 1590:

5'-GGACGCTGGA TTAGAAGGCA GCAAA-3' (SEQ ID NO:46)

is located in SEQ ID NO:1 at 1-25; and primer 1591:

5'-CCACACCCAG CCTAGTCCC-3' is located in SEQ ID NO:1 at 71-89. Several positive clones were isolated by PCR and two, designated P1-11 and P1-47, were subjected to Southern blotting analysis and PCR assays to confirm the presence of the entire PEDF gene and splice junctions. Primer pairs encompassing contiguous stretches of the PEDF cDNA sequence were used to amplify products from P1-11. The primers were as follows: primers 601 and 1591 (spanning bases 1-89 of SEQ ID NO:1; 601 is the sense strand and includes bases 1-25; 1591 is the antisense strand and includes bases 69-89), primer 2213 (SEQ ID NO:1 at 114-133) and 2744 (antisense strand in SEQ ID NO:1 at 224-244); 603 (SEQ ID NO:1 at 271-290) and 604 (antisense strand in SEQ ID NO:1 at 570-590); 605 (SEQ ID NO:1 at 570-590) and 606 (antisense strand in SEQ ID NO:1 at 829-848); 2238 (SEQ ID NO:1 at 846-866) and 354 (antisense strand in SEQ ID NO:1 at 1043-1062) and 356:499 (spanning bases 1034-1472 of SEQ ID NO:1; 356 is the sense strand and includes bases 1043-1043; 499 is the antisense strand and includes bases 1448-1472). The products obtained were 89 bp, 2.3 kb, 2 kb, 3.3 kb, 1.5 kb and 900 bp, respectively. The products were sequenced with an automated fluorescent sequencer to confirm splice junctions of the PEDF gene from sequences obtained from non-PI clones.

EXAMPLE 50

Characterization of Genomic Clones DNA Sequencing:Dideoxynucleotide Termination Method jt101 and jt106 were purified by gel electrophoresis and subcloned into the BamHI and NotI sites respectively, of pBluescript II SK+ vectors (Stratagene). These were used to transform XL-I Blue competent cells (Stratagene). Transformants were isolated and subcloned. The clones were blunt ended using T4 DNA polymerase, gel purified and subcloned into the EcoRV site of pBluescript II SK⁻ (Stratagene) and used to transform XL-I blue cells. Nested deletions were generated from both the T7 and T3 ends of the subclones using ExoIII and SI nuclease (Lark Sequencing Co.). Plasmid DNA was prepared using a modified alkaline lysis procedure and deletions clones size selected for DNA sequencing by electrophoresis on agarose gels. DNA sequencing (Lark Sequencing Co.) was performed using standard dideoxynucleotide termination method and sequencing reactions analyzed on 6% w/v polyacrylamide wedge gels containing 8 M urea.

jt108, jt109, jt115 and jt116 (PCR products) were cloned into the modified EcoRV site of the PT7 Blue vector (Novagen). These were subsequently used to transform Nova Blue cells (Novagen) such that both orientations of the insert into the vector were obtained. Nested deletions were then generated from the reverse end minilysates using ExoIII and SI nuclease and sequenced as above.

The sequence analysis of all the above clones the structure and size of exons and introns of the human PEDF gene were determined. Exon/intron junctions were established by comparing genomic and cDNA sequence of PEDF and by identifying consensus splicing sites (Senapathy et al., *Methods in Enzymology* 183 252, 1990). The analysis indicates that the human PEDF gene is approximately 16 kb in length and is composed of 8 exons ranging in size from 92 nt to 377 nt and 7 introns ranging from 0.4 kb to 6 kb (Table 1). The 5' splice donor and 3' splice acceptor sites in all junctions conform to the GT/AG consensus. Exons are distributed unevenly throughout the gene and the largest intron of 6 kb long is located between exon 1 and exon 2. No significant patterns were seen in the spatial organization of exons, in the distribution of introns or in the occurrence of certain types of splice junctions to infer a unique evolutionary relationship among any subset of exons.

EXAMPLE 51

Characterization of Genomic Clones DNA Sequencing: Fluorescent Automated DNA Sequencing Fluorescent sequencing was performed using an ABI model 370A instrument connected to an Apple Macintosh ci and ABI's 373 A sequencing software. The sequencing was performed using ABI's Taq DyeDeoxy Terminator cycle sequencing kit following the manufacturer's protocol. In general, 0.5 pmoles of template obtained from PCR products of the P1-10 clone and 3 pmoles of primer were used per sequencing reaction. All other details are provided in the ABI's manual included in the sequencing kit.

jt101: Sequence analysis of this 7.1 kb BamHI fragment contained the most 3' end of the PEDF gene. Exon 7 (SEQ ID NO:1 at 903-1113) and exon 8 (SEQ ID NO:1 at 1114-1503) of 211 bp and 377 bp, respectively, were contained in this clone. Intron 6 and intron 7 were also sequenced from jt101. Intron 7 was intact and found to be 444 bp in length while intron 6 was found to be somewhat rearranged.

jt106: Sequence analysis of this 7.2 kb NotI fragment indicated only sequences present in the most 5' end of the PEDF gene. This clone contained the promoter of the PEDF gene as well as exon 1 representing 109 bp (SEQ ID NO:1 at 1-109) and an incomplete intron 1 of 535 bp. We were unable to obtain specific PCR amplification products for this intron from either total human genomic DNA or the PI clones suggesting that the size of the first intron was rather enormous.

jt108: The PCR clone jt108 contained a 2 kb PCR product amplified using primer 603:604 and contained most of exon 3 and exon 4. Intron 3 and intron 4 of 980 bp and 689 bp, respectively, were sequenced from this clone.

jt109: This 3.3 kb clone representing PCR product obtained with primers 605:606 contains most of exon 5 and exon 6 (bases 555-758 of SEQ ID NO:1). The 3 kb intron 5 is also present in this clone.

jt115: The 2.3 kb clone JT115 obtained from the PCR product amplified using the primer pair 2213:2744 contained exon 2 and intron 2 which is 2.9 kb in length.

jt116: Sequence analysis of this PCR clone obtained with primers 2238 and 354 revealed an intact 1.5 kb intronic sequence representing intron 6 previously determined from sequence analysis of jt101.

P1-11: The intron-exon boundaries of the PEDF gene in the P1-11 clone using primers designed from exon sequences flanking each intron have also been sequenced. Approximately 200 bp on either side of the junctions were sequenced and these align perfectly with the sequence obtained from the above clones. All splice junctions sequences were confirmed as well as the sizes of introns and exons.

Part of the genomic DNA sequence is presented in SEQ ID NOs: 4 to 6.

EXAMPLE 52

Characterization of Genomic Clones DNA Sequencing: RACE

For RACE (Rapid amplification of cDNA ends) (Frohman In: *PCR protoclols: A Guide to Methods and Applications* pp 28-38, Innis, Gelfand, Sninsky and White eds., Academic Press, 1990) experiments 1.0 μg of total human retina RNA was dried with 20 nanograms of primer 1590 (SEQ ID NO:1 at 1-25). Reverse transcriptase, reaction buffer and dNTP solution (BRL) were added to a final volume of 20 μl. The reaction was carried out at 42° C. for 30 minute followed by a 5 minute incubation at 55° C. Templates were tailed with poly (A) using terminal deoxytransferase (BRL). Sequences corresponding to the 5' end of mRNA were then amplified by PCR using specific primer 1591. The product obtained from the PCR reaction was sequenced directly using an ABI automated fluorescent sequencer.

EXAMPLE 53

Gene Expression Analysis

Multiple human tissue mRNA Northern blots (Clonetech) with 2 μg poly(A) RNA per lane were hybridized with a radioactively labeled 667 bp PCR amplified PEDF product (Tombran-Tink et al., *Genomics* 19 266-272, 1994). The blots were prehybridized for 30 minute in Stratagene's QUIKHYB solution at 68° C. The labeled probe was added to this solution and hybridization continued at the same temperature for 1 hour. Hybridized blots were washed twice for 15 minute with 2×SSC/0.1% w/v SDS at room temperature and once for 30 minute with 0.1×SSC/0.1% w/v SDS at 68° C. The blots were exposed for 6 hours at −70° C. using XAR-5 film (Kodak) and intensifying screens.

EXAMPLE 54

Evolutionary Conservation Analysis

Eight μg of genomic DNA from lymphocytes of a variety of species including mammalian and primate species (BIOS laboratories, New Haven Conn.) was digested with EcoR1 and separated in 1% w/v agarose gels. The gels were transblotted and membranes containing the digested DNA hybridized using the same procedure as for the Northerns.

These studies indicated that the sequence of the PEDF gene is highly conserved in avian, mammals and primates, as indicated by Northern blots which are performed under stringent conditions. Under weaker hybridization conditions, the PEDF gene from species, lower on the evolutionary scale also are identified, this includes Drosophila.

EXAMPLE 55

Expression and Secretion of the PEDF in Retinal Interphotoreceptor Matrix

Monkey eyes were obtained through the courtesy of the Office of Biologics, FDA. The procedures for establishing RPE cells in culture and describing their differentiated characteristics have been published previously (Pfeffer, 1990. In Progress in Retinal Research. N. Osborne and G. J. Chader editors. Pergamon Press, Oxford UK. 251-291). Conditioned medium and cultured monkey RPE cells were used from the 1st, 2nd, 5th, 10th and 15th passages of the cells. The cells were routinely maintained in Minimal Essential Medium (MEM, Eagle's salts, Mediatech, Hearndon, Va.) containing 0.5% v/v fetal calf serum (FCS, GIBCO, Grand Island, N.Y.). Cells from confluent monolayer cultures were scraped from flasks, solubilized in phosphate-buffered saline (PBS, pH, 7.4) containing 0.5% v/v Triton-X (Sigma Chemical Co., St. Louis, Mo.) and stored at −70° C. for Western blot analysis. For Northern blot analysis, the following sources of RNA were used: 1) cultured fetal and adult human RPE cells (Flannery et al., *Exp. Eye Res.* 51 717-728, 1990), 2) human RPE cell explants from 21 week gestational donors (obtained from Dr. W. O'Day, Jules Stein Eye institute, UCLA,) 3) human and monkey retina (Clonetech), 4) 1st and 10th passaged monkey RPE cell cultures (eyes obtained courtesy of In Vitro Vaccine Testing Section, FDA, Bethesda, Md.).

Conditioned medium (CM) from cultured fetal and adult human RPE cells was obtained from monolayer cell cultures grown as previously described (Carlson et al., *Biochemistry* 31 9056-9062, 1992). CM from young adult monkey and primary cultures of 11 day old chick embryo were kind gifts of Dr. Bruce Pfeffer (NEI) and Margaret Koh (Univ. of Maryland Medical School), respectively. The medium was conditioned for 7 days by confluent monolayers of RPE cells, filter-sterilized and stored at −70° C. until used. Medium conditioned by confluent monolayer of monkey RPE cells after the 1st, 2nd, 5th, 10th and 15th passage was used for Western blot analysis to study the secretion of PEDF with successive cell passages.

Soluble IPM preparations were obtained from adult human (obtained from the Clinical Branch, NEI), fetal bovine (10 weeks gestation) and adult bovine eyes (obtained from Trueth and Sons, Baltimore, Md.) as previously described (Tombran-Tink et al., *J. Comp. Neurol.* 317 175-186, 1992). Briefly, the anterior segment, lens and vitreous were removed; the resultant eye cups and retina were gently rinsed with 0.5 ml of PBS solution. This preparation, which contained soluble IPM components was centrifuged and the supernatant stored at −70° C. RPE cells were removed from the eye cup by vigorous repeated pipetting of a small amount of PBS against the cells in situ to detach them from the underlying Bruch's membrane. The retina and the RPE cells were subsequently solubilized in SDS sample buffer to be used for Western blot analysis.

Protein concentrations were determined using the BCA assay (Pierce Chemical Co., Rockford, Ill.) according to the manufacturer's specifications. Samples of conditioned medium, IPM or cell extracts were lyophilized and 15 µg of each reconstituted in SDS sample buffer and boiled for 5 minutes. The proteins were fractionated on 10% w/v polyacrylamide gels at 25 mAmps/gel constant current for 3 hours (Laemmli, *Nature* 227 680-685, 1970). Five µg samples of human $\alpha$-1-antitrypsin and $\beta$-actin (Sigma Chem. Co.) were included on the gels. The resultant gels were either stained with Coomassie Brilliant Blue (Sigma Chem. Co.) for visualization of the electrophoretic protein profile or transblotted onto nitrocellulose membranes for Western blot analvsis.

Two dimensional gel analysis of 1) purified PEDF protein from CM of cultured fetal RPE cells as previously described (Tombran-Tink et al., *Exp. Eye Res.* 53 411-414, 1991), 2) CM from cultured human RPE cells (Tombran-Tink et al., *Exp. Eye Res.* 53 411-414, 1991) and 3) adult bovine IPM prepared as previously described (Tombran-Tink et al., *J. Comp. Neurol.* 317 175-186, 1992) was performed according to the method of O'Farrell (*J. Biol. Chem.* 250 4007-4021, 1975). Isoelectric focusing was carried out in glass tubes of inner diameter 2.0 mm, using 2% v/v BDH pH 4-8 ampholines for 9,600 volt hours. The final tube gel pH gradient extended from about pH 4.0 to about pH 8.2 as measured by a surface pH electrode. After equilibration for 10 minutes in buffer 0 (10% v/v glycerol, 50 mM dithiothreitol, 2.3% w/v SDS and 62.5 mM Tris, pH 6.8), the tube gel was sealed to the top of a 10% w/v acrylamide slab gel (0.75 mm thick) and electrophoresis was carried out for 4 hours at 12.5 mAmps/gel. The gels were then either stained with Coomassie blue or transblotted onto nitrocellulose membrane for Western blot analysis.

Nitrocellulose membranes containing the transblotted proteins were pretreated with 0.5% w/v non-fat dried milk in 50 mM Tris buffer, pH 7.4, followed by incubation for 1 hour with an anti-PEDF polyclonal antibody (a gift of Dr. Vincent Cristofalo, Medical College of Pennsylvania) diluted at 1:3, 000 in Tris buffer containing 0.5% v/v milk. After this treatment, the membranes were washed extensively with Tris buffer and subjected to further incubation for 30 minutes in an appropriate dilution of alkaline phosphatase-conjugated goat anti-rabbit IgG. The alkaline phosphatase color development reagents p-nitro blue tetrazolium chloride (NBT) and 5-bromo-4-chloro-3'indoyl phosphate p-toluidine salt (BCIP) (BioRad Laboratories, Richmond, Calif.) were used for the detection of the PEDF protein.

First strand cDNA synthesis of human and monkey RPE cell mRNA was performed using the SuperScript Preamplification System catalyzed by SuperScript RNase H-Reverse Transcriptase (RT) (Gibco, BRL, Gaithersburg, Md.). A 3 µl sample of the resulting first strand cDNA was then used for each PCR reaction. A pair of primers from the translated sequences of the PEDF cDNA (Steele et al., *Proc. Natl. Acad. Sci.* (*USA*) 90 1526-1530, 1993), representing a 1472 bp PCR amplification product, was used in the reactions. The primers were 601 and 499, which have been described previously. The PCR reaction contained 10 mM Tris-HCl, pH 8.3, 50 mM KCl, 80 µM of each dNTP, 1 mM $MgCl_2$, 100 ng of each primer and 1.25 units of Amplitag (Perkin Elmer Cetus). A preamplification denaturation for 10 minutes at 94° C. was performed and amplification was then carried out for 30 cycles. Each cycle was: 94° C., 1 minute; 50° C., 1 minute; 72° C., 1 minute. Six µl of the PCR products were analyzed on a 1% w/v agarose gel in 1×TAE buffer and products visualized with ethidium bromide.

Total RNA was isolated by the RNAzol B method (Cinna/Biotecx, Friendswood, Tex.). Ten µg of total RNA was diluted in RNA-loading dye containing ethidium bromide (5'Prime-3'Prime, Inc., Boulder, Colo.) and electrophoresed for 3 hour at 75 V in 1% v/v formaldehyde gels. The RNA was subsequently transferred onto Nytran membranes (Schleicher & Schuell, Keene, N.H.) using 20×SSC and Stratagene's Posiblotter (Stratagene, La Jolla, Calif.). The membranes were UV crosslinked and baked at 80° C. for 2 hours prior to hybridization. Fifty ng of a 667 bp PCR amplified product of the PEDF cDNA was used as the probe. This was labelled with $\alpha$-$^{32}$P-dCTP using a Random Prime It Kit II (Stratagene). Unincorporated nucleotides were removed using Stratagene's Nuctrap Push columns. The membranes were prehybridized for 30 minutes at 68° C. in QuikHyb solution (Stratagene) followed by hybridization for 1 hour at 68° C. in the same solution supplemented with 1×10$^6$ cpm/ml radiolabelled PEDF probe. Post-hybridization washes were as follows: 2×15 minute at 25° C. with 2×SSC/0.1% w/v SDS buffer followed by 1×30 minute at 68° C. with 0.1×SSC/0.1% w/v SDS. The hybridized membranes were exposed overnight at −70° using XAR-5 X-Ray films (Eastman Kodak Co. Rochester N.Y.) and intensifying screens.

A human fetal eye of estimated 17 weeks gestation and 1.5 hours postmortem was fixed in 4% v/v formaldehyde following the removal of cornea, iris and lens. Following fixation, the posterior segment of the eye was cut into 1×2 mm pieces, dehydrated in ethanol and embedded in diethylene glycol distearate (Polysciences, Warrington, Pa.). Sections one micrometer in thickness were cut and handled as previously published (Porrello et al., *J. Histochem. Cytochem.* 39 171-176, 1991).

A 233 bp fragment containing residues 246-278 of the coding region was exceed by BamHI and KpnI digestion of human PEDF cDNA (Steele et al., *Proc. Natl. Acad. Sci.* (*USA*) 90 1526-1530, 1993). This fragment was then ligated into pBluescript II KS-phagemid (Stratagene). The phagemid with its 233 bp PEDF insert was then linearized by digestion within its multiple cloning site with StyI or with BamHI, neither of which have restriction sites in the PEDF fragment. T3 and T7 RNA polymerase were incubated with these DNA templates to generate a sense probe 264 bases and an antisense probe 300 bases in length. Forty of the bases in the sense probe and 67 in the antisense probe were transcribed from vector DNA.

$^{35}$S-labeled probes were synthesized with a Riboprobe kit (Promega, Madison, Wis.) according to the manufacturer's instructions. Optimal radiolabel incorporation for a 1 AM volume was typically $1 \times 10^6$ DPM for the sense and antisense probes. Hybridization and posthybridiation of the probes with tissue sections were performed as previously described (Porrello et al., J. Histochem. Cytochem. 39 171-176, 1991) with the exception that the salt washes were performed at 65° C.

Monkey RPE cells, cultured in MEM containing 1% v/v FBS, were seeded onto glass coverslips in 24 well plates. The cells were fixed in 4% v/v paraformaldehyde for 15 minutes and non-specific protein binding sites blocked with 1 mg/ml bovine serum albumin. The PEDF polyclonal antibody was used at a 1:3,000 dilution and cells were reacted with the antibody for 1 hour followed by incubation for 30 minutes in an appropriate dilution of FITC-conjugated goat anti-rabbit IgG. Double-labelling experiments were performed similarly using an actin monoclonal antibody and rhodamine-conjugated goat anti-mouse IgG (Pierce, Rockford, Ill.). Immunoreactivity was visualized by epifluorescence microscopy using an Olympus BHS microscope equipped with a 40×UV lens.

Coomassie blue staining of proteins in fetal human RPE-CM shows a prominent 50 kDa PEDF band that was completely absent from non-conditioned medium. By Western blot analysis, a comparable band at 50 kDa was readily detected by anti-PEDF in conditioned medium from RPE cells and in soluble washes of IPM from a number of species. The 50 kDa protein was found in RPE-CM from both fetal and adult human RPE cells. CM from young adult monkey (third passage in culture) and from primary chick embryo RPE cells also showed 50 kDa bands with the human PEDF polyclonal antibody. A positive PEDF band was also detected in soluble washes of adult human IPM and in IPM from fetal and adult cow. PEDF was often clearly defined as a doublet in lanes with lower concentration of PEDF. The presence of PEDF in the IPM indicates that it was secreted in vivo in both fetal and young adult where it could influence neuronal differentiation and/or survival of retinal neurons.

Interestingly, a 50 kDa protein, was not detected in total cellular extracts of tenth passage RPE cells. To better examine the effect of cellular ageing, CM from RPE cell up to 15 passages in culture was examined. PEDF was found to be secreted in abundance by RPE cells in their 1st and 2nd passages and at the 3rd passage but only weakly by these cells in the 5th passage. The protein was not detected in the conditioned medium of RPE cells at the 10th or 15th passages. Thus, PEDF secretion by RPE cells decreases dramatically in an age-related manner.

Surprisingly, the anti-PEDF antibody detects a doublet migrating at 36 kDa rather than at 50 kDa in both the cultured RPE cells and tissue extracts. The low level of the 36 kDa species observed in extracts of the neural retina await confirmation by immunocytochemistry in situ since it would be expected that small amounts of RPE contamination would be present in the dissected retinal tissue. This raises the possibility that some PEDF is retained intracellularly as a lower molecular weight species at least in RPE cells. It is also interesting to note here that, similar to the 50 kDa secreted protein, the 36 kDa species is only present in early passage cells and absent by the loth passage of the RPE cells. Thus, both molecular species disappear in parallel with cell passages and aging.

By 2-dimensional gel analysis, at least four isoforms of the HPLC-purified native human PEDF protein are detected by Coomassie blue staining. The spots vary only slightly in apparent molecular weights and the four most prominent species have apparent pI's of 6.0, 6.2, 6.4 and 6.6. The PEDF polyclonal antibody recognizes all four isoforms of this protein and possibly two others in both human RPE-CM and bovine IPM as shown by Western blot analysis of the transblotted 2-D gels.

Using primers 601 and 499 which encompass a 1.47 kb sequence of the PEDF message, a single product of approximately 1.5 kb is amplified in both fetal human and adult monkey RPE cells. By Northern blot analysis, a 1.5 kb band is also detected with the 667 bp PCR-amplified PEDF probe in cultures of fetal and adult human RPE cells as well as in RPE cell explants. Relatively more PEDF mRNA is seen in the fetal RPE cell explants as compared to cultured cells. No difference is seen in the size of the messages under any of the conditions (fetal vs. adult, human vs. monkey). Thus, by Western and Northern blot analyses and by PCR, the molecular size and apparent structure of the 50 kDa protein and its message appears to be similar in human, monkey and bovine RPE cells, retina and IPM.

Five μg of total RNA from monkey retina and from 1st and 10th passage monkey RPE cells were electrophoresed and a weak hybridization signal was seen from total retina RNA. A more, prominent 1.5 kb transcript band was present in the early passage (1st passage) monkey RPE cells while no transcript is detected in the late (10th) passaged RPE cells. Thus, similar to the secretion pattern of PEDF protein after successive RPE cell passages, late passage monkey RPE cells do not transcribe the PEDF mRNA.

The effect of PEDF on Y79 retinoblastoma cell line differentiation was first demonstrated with conditioned media from human fetal RPE cells. Thus, we performed in situ hybridization of a fetal human retina of a developmental age similar to that of the cells used for fetal human RPE culture (17 weeks gestation). Retinas hybridized with antisense probes under high stringency (65° C.) showed specific binding of the probe to the RPE cell layer. The retinal neuroblastic layer which contains incompletely differentiated neurons and glia and the ganglion cell layer, which was well differentiated at this developmental stage, were not labeled above background.

In well attached cells (3rd passage, 5-10 days postattachment), immunofluorescence was seen in association with cytoskeletal strands within the cells and within the nucleus. At 2 days of attachment, the protein was concentrated around the nucleus and was of a granular nature. Staining was also associated with a fibrous cytoskeletal-like network. When monkey RPE cells are examined soon after seeding (1-2 hours), discrete localization of the PEDF protein is seen at the tips of many processes of the RPE cell. Similar to the dramatic decrease seen in PEDF secretion and transcription with successive cell passages, no immunoreactivity with the PEDF polyclonal antibody is seen in cultured monkey RPE cells after the tenth passage.

To further examine the association of PEDF immunoreactivity with cytoskeletal elements within the cytoplasm, we analyzed the structures by double-labelling using anti-PEDF as described above and an actin antibody detected by rodamine-conjugated goat anti-mouse IgG. Both antibodies localized to structures around the nucleus and to cytoskeletal strands in the cytoplasm. Concentration of both antibodies is also seen at the tip of a pseudopod. Because of PEDF's apparent association with cytoskeletal structures, possibly actin microfilaments, we addressed the possibility of antibody cross reactivity with actin. Anti-PEDF did not bind to purified actin on a Western blot. Only a positive PEDF band at 50 kDa is observed in RPE conditioned medium. The antibody also does not recognize human $\alpha$-1-antitrypsin, a homologous member of the serpin supergene family. It thus seems that the PEDF antibody specifically recognizes and binds to PEDF (50 and/or 36 kDa forms) associated with the intracellular actin cytoskeletal network of the RPE cells but does not bind directly to purified actin on a Western blot.

EXAMPLE 56

PEDF as a Survival Factor for Cerebellar Granule Cells in Culture

Cerebellar granule cells (CGC) were prepared from 5 or 8-day-old Sprague Dawley rat pups (Taconic Farms) as previously described (Novelli et al., *Brain Res.* 451 205-212, 1988; Levi et al., In: *A Dissection and Tissue Culture Manual of the Nervous System* (Shahar, de Vellis, Vernadakis and Haber, eds), pp. 211-214. Alan R. Liss, Inc. New York. 1989). In brief, tissue free of meninges was minced in a buffer containing 124 mM NaCl, 1 mM $NaH_2PO_4$, 1.2 mM $MgSO_4$, 3 mg/ml bovine serum albumin (BSA), 27 µM phenol red, and 25 mM HEPES, pH 7.4, and centrifuged at 550×g for 3 minutes. The tissue pellet from 10-20 animals was resuspended and trypsinized for 15 minutes at 37° C. in 30 ml of the same buffer containing 250 µg/ml trypsin; a further 15 ml of buffer, containing 26 µg/ml DNase I (from Sigma Chemical Co.), 166 µg/ml soybean trypsin inhibitor (from Sigma Chemical Co.) and 0.5 mM additional $MgSO_4$, were added and the tissue was centrifuged again as described above. The pellet was resuspended in 1 ml of buffer supplemented with 80 µg/ml DNase, 0.52 mg/ml of trypsin inhibitor, and 1.6 mM additional $MgSO_4$, and triturated 60 times with a Pasteur pipette. The suspension was diluted with 2 ml of buffer containing 0.1 mM $CaCl_2$ and 1.3 mM additional $MgSO_4$, and undissociated material was allowed to settle for 5 minutes. The supernatant was transferred to another tube, cells were recovered by brief centrifugation and resuspended in serum-containing medium (Eagle's basal medium, from GIBCO, with 25 mM KCl, 2 mM glutamine, from GIBCO, 100 µg/ml gentamicin, and 10% v/v heat-inactivated fetal calf serum, from GIBCO) or chemically defined medium (DMEM:F12 (1:1, from GIBCO) with 5 µg/ml insulin (from Boehringer Mannheim), 30 nM selenium (from Boehringer Mannheim), 100 µg/ml transferrin (from GIBCO), 100 nM putrescine (from Sigma Chemical Co.), 20 nM progesterone (from Sigma Chemical Co.), 50 U/ml penicillin, 50 µg/ml streptomycin, and 2 mM glutamine; Bottenstein, In: *Cell Culture in the Neurosciences*, Bottenstein and Sato, eds., pp. 3-43. Plenum Publishing Corp, New York, 1985). Cells were plated in poly-L-lysine-coated 96-well plates (for MTS assay, MTS assay kit were obtained from Promega Corp., and neurofilament ELISA assay) or 8-well chamber slides (for immunocytochemistry and 5-bromo-2'-deoxyuridine, BrdU, labelling) at $2.5×10^5$ cells/cm² and grown at 37° C. in a humidified atmosphere comprising 5% v/v $CO_2$ in air. After 1 day in culture, cytosine arabinoside (Ara-C) was added only to cells in serum-containing medium to a final concentration of 10 µM.

Cerebellar granule cells in 96-well plates were incubated in a $CO_2$ incubator for 4 hours with MTS (3-(4,5-dimethylthiazol-2-yl)-5-(3-carboxymethoxyphenyl)-2-(4-sulfophenyl)-2H-tetrazolium, inner salt) and PMS (phenazine methosulfate) at final concentration of 333 µg/ml MTS and 25 µM PMS, respectively. In the presence of PMS, MTS is converted to a water-soluble formazan by a dehydrogenase enzyme found in metabolically active cells (Cory et al., *Cancer Commun.* 3 207-212, 1991). The quantity of formazan product was determined by spectrophotometry (Dynatech microplate reader) at 490 nm.

After 7 days in vitro (DIV), the cells were washed three times in calcium- and magnesium-free phosphate-buffered saline (PBS) and fixed with 2% v/v paraformaldehyde for 10 minutes, followed by 10 minutes at −20° C. in 95% v/v ethanol/5% v/v acetic acid. Incubation with primary antibodies against NSE (neuron-specific enolasecalbindin, from Sigma Chemical Co.), GABA (from Sigma Chemical Co.), calbindin (from Sigma Chemical Co.), or glial fibrillary acidic protein (GFAP) was carried out for 60 minutes at room temperature. Antibodies were applied at dilutions of 1:500-1:5,000 in the presence of 2% v/v normal goat serum and 0.2% v/v BSA. The antibodies were visualized using the ABC system (from Vector Lab) and diaminobenzidine. At least 20 fields were counted from 2-3 wells for each experiment. The average number of cells per field was then calculated to determine the ratio for the number of cells stained by the other antibodies relative to NSE-positive cells in control cultures.

BrdU labeling (BrdU labeling kit was supplied by—Amersham) was performed by the method described (Gratzner, *Science* 218 474-475, 1982; Gao et al., *Neuron* 6, 705-715, 1991) with the following modifications. The cells were plated in 8-well chamber slides and PEDF was immediately added. For this experiment, DMEM rather than DMEM:F12 was used in chemically defined medium (CDM) and no Ara-C was added to serum-containing medium (SCM). After 24 hours, BrdU (diluted 1:100; Amersham cell proliferation kit) was added to the culture medium for 24 hours, after which the cells were fixed in 2% v/v paraformaldehyde for 10 minutes, treated with 95% v/v ethanol, 15% v/v acetic acid for 10 minutes, and incubated with an anti-BrdU monoclonal antibody, which was diluted 1:20, for 2 hours. The cultures were then incubated with a horseradish peroxidase-conjugated goat anti-mouse secondary antibody (Vector Lab) for 60 minutes. After incubation with diaminobenzidine, the cells were mounted in Gel Mount. The mitotic index was determined by counting the percentage of labeled cells with microscopy. For each value, a random sample of 3,000 cells was counted.

Neurofilament ELISA was performed according to the method of Doherty et al. (*J. Neurochem* 42 1116-1122, 1984) with slight modifications. Cultures grown in 96-well microtiter plates were fixed with 4% v/v paraformaldehyde in PBS at 4° C. for 2 hours. The fixed cells were permeabilized by treatment for 15 minutes with 0.1% v/v Triton X-100 in PBS, followed by incubation for 60 minutes with PBS containing 10% v/v goat serum to block nonspecific binding. The cultures were then incubated with a monoclonal anti-neurofilament antibody (RMO-42) overnight at 4° C. at a dilution of 1:100 (Lee et al., *Proc. Natl. Acad. Sci. USA* 85 7384-7388, 1988). After washing twice with PBS containing 10% v/v goat serum, cells were incubated with secondary antibody (horseradish peroxidase-conjugated goat anti-mouse at a dilution of 1:1,000) for 1 hour. Following sequential washing with PBS and water, the cultures were incubated with 0.2% v/v o-phenylenediamine (OPD, from Sigma Chemical Co.) and 0.02% v/v $H_2O_2$ in 50 mM citrate buffer, pH 5.0, for 30 minutes. The reaction was stopped by adding an equal volume of 4.5 M $H_2SO_4$. Product formation was quantitated by reading the optical density (O.D.) of an aliquot of the reaction product at 490 nm using a Dynatech microplate reader.

The PEDF used in the experiments was a recombinant construct ($Asp^{44}$-$Pro^{418}$) as previously described (Becerra et al., *J. Biol. Chem.* 268 23148-23156, 1993) and as described above. The recombinant expression construct from the human PEDF cDNA was expressed in *Escherichia coli* and purified from the bacterial inclusion bodies. rPEDF was highly purified by gel filtration and cation exchange chromatography, and demonstrated neurotrophic activity on human retinoblastoma Y-79 cells, as reported for the native PEDF (Becerra et al., *J. Biol. Chem.* 268 23148-23156, 1993) and as described above. rPEDF was added in urea at a final concentration of 500 ng/ml urea and 10 mM rPEDF. All controls contained the concentration of urea corresponding to that present in the rPEDF added and no dose of urea affected any of the assays.

All experiments were replicated twice. The statistical analyses that were carried out by standard statistical methods.

Unless indicated otherwise, all experiments were carried out using CGC prepared from postnatal day 8 (P8) rats. In SCM, optical density (O.D.) was proportional to the cell number plated over a range from 1 to $9 \times 10^5$ cells/cm$^2$. In contrast, for cells grown CDM, the linear range covered 1 to $5 \times 10^5$ cells/cm$^2$. For all subsequent experiments, cells were plated at $2.5 \times 10^5$ cells/cm$^2$, i.e., within the linear range for either type of culture medium.

Exposure of cells to 500 ng/ml (equivalent to 11.68 nM) rPEDF in SCM resulted in a statistically significant difference in the O.D. between rPEDF-treated and untreated cultures by two days in vitro (DIV 2): the difference lasted up to DIV 10. By DIV 4, there was a 50% increase in cell number in the presence of rPEDF, with a 30-40% increase maintained through DIV 10. A dose-response curve demonstrated that the effect of rPEDF was statistically significant at 500 ng/ml or above, although increasing the concentration above 500 ng/ml did not produce further increases. PEDF had a much larger effect on cell number when added to CGC in chemically defined medium. The time course of the rPEDF effect in CDM. The time course analysis demonstrates that rPEDF-treated cultures contain significantly more cells than control cultures by DIV 4, with even larger differences by DIV 7 and 10. Most of the 2-3 fold difference was the result of large decreases in cell numbers in the control cultures. The dose-response curve in CDM shows that there is a statistically significant effect at 20 ng/ml (equivalent to 0.47 nM) rPEDF, 25-fold lower than the effective dose in serum-containing medium. Increasing the concentration of rPEDF above 50 ng/ml did not promote further survival of CGC in CDM.

Immunocytochemistry was used to identify the cell types present in CGC cultures before and after treatment with rPEDF. Postnatal day 8 CGC cultures grown for 7 days with or without rPEDF (500 ng/ml) were stained with four different antibodies: 1) a polyclonal rabbit antibody to neuron-specific enolase (NSE), which recognizes all differentiated cerebellar neurons, including P8 CGC which are differentiated both morphologically and pharmacologically by DIV 7; 2) a polyclonal antibody to GABA, which stains all cerebellar neurons except cerebellar granule cells; 3) an antibody to calbindin, which is specific for Purkinje cells; 4) an antibody to glial fibrillary acidic protein (GFAP), an intermediate filament protein present only in astrocytes. The results are summarized in Table IV.

TABLE IV

| Antigen | Treatment | SCM | CDM |
| --- | --- | --- | --- |
| NSE | Control | 100.0 ± 6.2 | 100.0 ± 4.5 |
|  | PEDF | 127.0 ± 5.9* | 157.2 ± 7.4* |
| GABA | Control | 2.8 ± 0.2 | 1.4 ± 0.2 |
|  | PEDF | 3.2 ± 0.2 | 1.8 ± 0.2 |
| Calbindin | Control | 0.06 ± 0.01 | 0.07 ± 0.02 |
|  | PEDF | 0.07 ± 0.02 | 0.12 ± 0.02 |
| GFAP | Control | 0.86 ± 0.07 | 0.99 ± 0.07 |
|  | PEDF | 0.06 ± 0.03* | 0.60 ± 0.06* |

* $p < 0.005$ relative to the respective control

*$p<0.005$ relative to the respective control

There were significantly more NSE-positive cells in both SCM (30% increase) and in CDM (60% increase) in the presence of rPEDF. No statistically significant increase was observed in the number of GABA-positive neurons or Purkinje cells (calbindin-positive). Furthermore, the results support the purity of the CGC cultures, since only 1-3% of the cells are GABA-positive non-CGC neurons, less than 0.1 are Purkinje cells and less than 1% are astrocytes. The increased number of NSE-positive cells in the presence of rPEDF, therefore, reflects enhanced survival of CGC neurons.

In order to determine whether the increase in O.D. (MTS assay) in response to PEDF reflected simply cell, survival or an increase in proliferation, a BrdU labeling study was performed using cultures from postnatal day 5 (P5) animals, a time when cerebellar granule cells are still dividing in vivo. First, the effect of rPEDF on P5 CGC cultures at DIV 1 and 2 was determined using the MTS assay. PEDF had no effect at DIV 1 but caused a small but significant increase in O.D. at DIV 2 in both serum-containing medium and chemically defined medium. Therefore, BrdU was added on DIV 1 and cells were fixed on DIV 2. Under control conditions, the BrdU labeling index was 5% in SCM and 3% in CDM: PEDF did not increase the BrdU labeling index in either culture medium. The lack of effect of PEDF on BrdU labeling showed that enhanced survival rather than increased cell division underlies the, larger cell number seen with PEDF.

In order to investigate the effects of rPEDF on neurite outgrowth from P8 CGC, a neurofilament ELISA assay was used. Immunocytochemistry had shown that the monoclonal antibody RMO-42, which recognizes the phosphorylated domain of NF-H (200 kDa) and NF-M (160 kDa), stained only the neurites of cerebellar granule cells in culture in comparison to anti-NSE which stained both neurites and cell bodies. Therefore, this antibody was used as a direct measure of neurofilament protein present in the neurites and an indirect measure of number of neurites. Using the neurofilament ELISA, the O.D. was found to be proportional to the number of cells originally plated when the assay was carried out on DIV 7, a time when all cells have developed a full complement of processes. rPEDF increased neurofilament content, both in SCM (45%) and CDM (43%) but the increase was directly proportional to the increase in cell number. When the data are expressed as the increase in neurofilament relative to the increase in cell number, these ratios are about 1.0 for both SCM and CDM. These results demonstrated that PEDF does not promote neurite outgrowth from CGC in culture. Microscopic observation revealed no morphological change caused by rPEDF.

In the present study, we show that PEDF increased the number of viable cells in cerebellar granule cell cultures, whether the cells were prepared from postnatal day 5 or postnatal day 8 rats, and whether the cultures were maintained in serum-containing medium or chemically defined medium. In SCM, PEDF showed no effect at DIV 1, but by DIV 4, about 50% more cells were present in PEDF-containing medium, a difference which was maintained through DIV 10. In CDM, a similar 50% difference was seen by DIV 4, with the difference becoming larger at DIV 7 and DIV 10 (final 2-3 fold more cells at these times in the presence of PEDF). The effect of PEDF showed a dose-response relationship in both SCM and CDM. However, whereas a significant effect was seen with 500 ng/ml (equivalent to 11.68 nM) of rPEDF in SCM, only 20 ng/ml (0.47 nM) of PEDF were required to achieve a significant increase in CDM. Thus, effects of PEDF were larger and occurred at 25-fold lower doses in CDM than in SCM. Furthermore, these effects of rPEDF were long-lasting in that only a single dose of the factor was added to culture medium at the start of the culture period. The relatively high potency of PEDF in CDM compared to SCM may be due, at least in part, to the presence of inhibitors or degradative enzymes in the fetal calf serum that reduced the bioactivity of PEDF. Alternatively, another trophic factor, additive in action to PEDF, may be present in serum, which masks the full biological activity of PEDF.

To determine whether this PEDF-induced difference in cell number reflected an increase in cell survival or an increase in proliferation, BrdU incorporation was measured in the presence of PEDF using cells from postnatal day 5 animals, an age when cerebellar granule cells are still dividing in vivo. PEDF did not alter BrdU incorporation into cells cultured in either SCM or CDM. The lack of effect of PEDF on BrdU incorporation indicates that enhanced survival rather than increased cell division underlies the larger cell number seen with PEDF. Since the MTS assay only determines total cell number, immunocytochemistry was used to identify the general types and relative proportions of cells present in cultures treated with PEDF. There were significantly more NSE-positive cells in PEDF-treated cultures. However, no statistically significant effect of PEDF was found on GABA-positive cells, which includes all cerebellar neurons except the granule cells, or on the number of calbindin-positive Purkinje cells. Since GABA-positive cells represent only 1-3% of the total NSE-positive neurons in the cultures and even fewer calbindin-positive cells are present (about 0.1%), it thus appears that PEDF affects only the CGC neurons. Moreover, the effect seems to be on long-term neuronal survival since PEDF does not promote increased mitotic activity. Our present results are of particular interest with regard to recent results on the expression of the PEDF gene in WI-38 fibroblast cells in culture. In these cells, PEDF (called EPC-1) mRNA accumulates in young WI-38 cells at $G_0$ but little or no transcription is found in senescent cells. No PEDF mRNA has been detected in P8 CGC neurons, in agreement with their lack of mitosis by P8. Just what roles PEDF may play in cell cycle or survival events remain to be determined. In this regard, it will be interesting in the future to determine if PEDF exerts an anti-apoptotic effect in promoting the survival of CGC.

Both purified native PEDF and recombinant PEDF exhibit a striking neurotrophic effect on cultured retinoblastoma cells as outlined above. rPEDF had no comparable effect on the morphology of the CGC, however. To investigate a possible effect of PEDF on neurite outgrowth, we used a specific neurofilament assay designed to quantify neurite outgrowth. Although the neurofilament content was higher at DIV 7 in PEDF-treated cultures (40% in both SCM and CDM), this simply reflected the fact that there were more cells present in the PEDF-treated cultures (30% in SCM and 60% in CDM by immunocytochemistry). The biochemical data are thus in concert with the morphological data and indicate that PEDF has no effect on neurite outgrowth in CGC.

Since PEDF shares considerable sequence homology with members of the serine protease inhibitor (serpin) supergene family, PEDF may act by inhibiting protease activity. The glia-derived nexins, other members of the serpin family, have been proposed to exert neurotrophic actions by regulating the balance between protease and protease inhibitor activities. However, PEDF lacks significant homology to the proposed consensus sequence for the serpin reactive center region, which itself is heterogeneous in length and amino acid composition. Furthermore, protease inhibition assays showed that PEDF did not affect trypsin, chymotrypsin, elastase, cathepsin G, endoproteinase Lys-C, endoproteinase Glu-C, or subtilisin activity, suggesting that inhibition of known serine proteinase may not be the biochemical pathway for the PEDF neurotrophic activity.

Aside from a direct action on cerebellar granule cells, it is also possible that PEDF acts to regulate expression of some other neurotrophic factor. BDNF and NT-3 are both present in the immature cerebellum, and Trk B, the BDNF receptor, is also expressed in the cerebellum early in development. BDNF was shown to act as a survival factor for embryonic granule cells. It increased cerebellar granule cell number 50 to 100% at 20 ng/ml, with the effect occurring after DIV 4, results very comparable to ours with PEDF. Furthermore, BDNF has no effect on mitosis of cerebellar granule cells. Since a number of hormones and neurotransmitters are known to affect the production of neurotrophins by neurons, the effect of PEDF could be mediated through regulation of one of these factors. Tri-iodothyronine, for example, enhanced the production of NT-3 in CGC cultures while neurotransmitters or analogs such as kainic acid and GABA increased the synthesis of NGF and BDNF in hippocampal neurons. Thus, PEDF may act directly through its own receptor and signal transduction pathway, or more indirectly through regulation of the production of other neurotrophic factors in the CGC cultures.

All of the references cited herein are hereby incorporated in their entireties by reference.

The above descriptions of exemplary embodiments of retinal pigmented epithelium derived neurotrophic factor are for illustrative purposes. Because of variations which will be apparent to those skilled in the art, the present invention is not intended to be limited to the particular embodiments described above. The present invention may also be practiced in the absence of any element not specifically disclosed. The scope of the invention is defined by the following claims.

What is claimed is:

1. A method of treating retinal tumors in a subject comprising administering to the subject an effective amount of Pigment Epithelium Derived Factor (PEDF) comprising the amino acid sequence of SEQ ID NO: 2 or SEQ ID NO: 3, wherein the PEDF induces a reduction in the rate of tumor growth or a reduction in the rate of tumor cell division.

2. The method according to claim 1, wherein the PEDF is formulated with a time-release compound.

3. The method according to claim 2, wherein the time-release compound is polylactic acid.

4. The method according to claim 1, wherein the PEDF is administered by intravitreal injection or subretinal injection.

5. The method according to claim 1, wherein the PEDF is administered at a concentration of 1 to 100 µg/ml 1 to 10 times per day.

6. A method of treating retinal tumors in a subject comprising administering to the subject an effective amount of Pigment Epithelium Derived Factor (PEDF) comprising the amino acid sequence of SEQ ID NO: 2, wherein the PEDF induces a reduction in the rate of tumor growth or a reduction in the rate of tumor cell division.

7. The method according to claim 1, wherein the PEDF is in a pharmaceutically acceptable vehicle.

8. The method according to claim 7, wherein the pharmaceutically acceptable vehicle is a saline solution.

9. The method according to claim 1, wherein from about 0.01 µg to about 10 µg of PEDF is administered to the patient at a concentration of about 1 to 100 µg/ml in a saline solution.

10. The method according to claim 1, further comprising administering the PEDF in conjunction with an additional active agent.

11. The method according to claim 6, wherein the PEDF is administered with a time-released compound.

12. The method according to claim 11, wherein the time-released compound is polylactic acid.

13. A method of treating retinal tumors in a subject comprising administering to the subject an effective amount of Pigment Epithelium Derived Factor (PEDF) comprising the amino acid sequence of SEQ ID NO: 3, wherein the PEDF induces a reduction in the rate of tumor growth or a reduction in the rate of tumor cell division.

* * * * *

UNITED STATES PATENT AND TRADEMARK OFFICE
CERTIFICATE OF CORRECTION

| | |
|---|---|
| PATENT NO. | : 7,511,009 B2 |
| APPLICATION NO. | : 10/216373 |
| DATED | : March 31, 2009 |
| INVENTOR(S) | : Joyce Tombran-Tink et al. |

It is certified that error appears in the above-identified patent and that said Letters Patent is hereby corrected as shown below:

Title Page,
Item (75) Inventors:
Lines 4-5, delete fourth inventor "Ignacio R. Rodriguez, Rockville, MD (US);".

Item (73) Assignee:
Delete "Washington, DC (US)" and insert -- Bethesda, MD (US) --.

Item (56) References Cited:
OTHER PUBLICATIONS
Page 1, column 2, "Zou, Z., et al.," reference, delete "Turmor-Suppressing" and insert -- "Tumor-Suppressing --.
Page 2, column 1, "Hewitt et al.," reference, delete ""Purifications," and insert -- "Purification, --.

Column 1,
Delete first paragraph, lines 6-9, and insert -- This application is a divisional of Application Serial Number 08/520,373, filed on August 29, 1995, now U.S. Patent No. 6,451,763, which is a continuation application of Application Serial Number 08/377,710, filed on January 25, 1995, abandoned, which is a continuation of Application Serial Number 08/279,979, filed on July 25, 1994, abandoned, which is a continuation-in-part of Application Serial Number 07/894,215, filed on June 4, 1992, abandoned, and a continuation-in-part of U.S. Patent Application Serial Number 07/952,796, filed on September 24, 1992, abandoned, U.S. Application Serial Number 07/894,215, filed June 4, 1992 and U.S. Patent Application Serial Number 07/952,796 filed on September 24, 1992, are incorporated herein by reference. --.

Column 3,
Line 63, after "PEDF" insert -- . --.

Column 6,
Line 36, delete "16 g/100 µl" and insert -- 16 µg/100 µl --.

Column 8,
Line 39, delete "chromatograph" and insert -- chromatography --.
Line 65, delete "chromatograph" and insert -- chromatography --.

UNITED STATES PATENT AND TRADEMARK OFFICE
CERTIFICATE OF CORRECTION

PATENT NO. : 7,511,009 B2
APPLICATION NO. : 10/216373
DATED : March 31, 2009
INVENTOR(S) : Joyce Tombran-Tink et al.

It is certified that error appears in the above-identified patent and that said Letters Patent is hereby corrected as shown below:

Column 10,
Delete lines 51-55 as follows "Heparin chromatography may also be used....Tris-HCl, pH7.5.".

Column 11,
Line 35, delete "bromphenol" and insert -- bromophenol --.

Column 14,
Line 62, delete "Tag" and insert -- Taq --.

Column 16,
Line 54, delete "50 µl" and insert -- 50 µg --.

Column 19,
Line 45, after "a" insert -- member of the --.
Line 45, after "inhibitor" insert -- family of proteins --.

Column 21,
Line 10, delete "bromphenol" and insert -- bromophenol --.

Column 22,
TABLE I-continued, column 2 "Relative concentration of PEDF", line 8 (row 80), delete "–" and insert -- +++ --.
TABLE I-continued, column 2 "Relative concentration of PEDF", line 9 (row 90), delete "–" and insert -- +++ --.

Column 25,
Line 40, delete "10 mM PBS," and insert -- 10 mM phosphate, --.
Line 42, delete "10 mM PBS," and insert -- 10 mM phosphate, --.

Column 29,
Line 9, delete "O=Farrell," and insert -- O'Farrell, --.

Column 30,
Line 30, delete "(SEO ID NO:23)" and insert -- (SEQ ID NO:23) --.
Line 31, delete "Asp Leu lie" and insert -- Asp Leu Ile --.
Line 38, delete "(SEO ID NO:26)" and insert -- (SEQ ID NO:26) --.

UNITED STATES PATENT AND TRADEMARK OFFICE
CERTIFICATE OF CORRECTION

PATENT NO. : 7,511,009 B2
APPLICATION NO. : 10/216373
DATED : March 31, 2009
INVENTOR(S) : Joyce Tombran-Tink et al.

Page 3 of 3

It is certified that error appears in the above-identified patent and that said Letters Patent is hereby corrected as shown below:

Column 31,
Line 23, delete "Cloning of the PEDF cDNA A6" and insert -- Cloning of the PEDF cDNA --.

Column 36,
Line 12, delete "5 µng/ml" and insert -- 5 ng/ml --.

Column 39,
Line 10, after "37°" insert -- C. --.

Column 43,
Lines 20-21, delete "syntenic" and insert -- synthetic --.

Column 44,
Line 22, delete "int he" and insert -- in the --.

Column 45,
Line 63, after "5'-CCACACCCAG CCTAGTCCC-3'" insert -- (SEQ ID NO: 47) --.

Column 51,
Line 11, delete "1 AM" and insert -- 1 µM --.

Column 56,
Line 1, delete the duplication of "*p<0.005 relative to the respective control".
Line 8, delete "0.1 are" and insert -- 0.1% are --.

Signed and Sealed this

First Day of September, 2009

David J. Kappos
*Director of the United States Patent and Trademark Office*

SEQUENCE LISTING

<160> NUMBER OF SEQ ID NOS: 48

<210> SEQ ID NO 1
<211> LENGTH: 1490
<212> TYPE: DNA
<213> ORGANISM: Homo sapiens
<220> FEATURE:
<221> NAME/KEY: CDS
<222> LOCATION: (117)..(1373)
<300> PUBLICATION INFORMATION:
<308> DATABASE ACCESSION NUMBER: M76979.1
<309> DATABASE ENTRY DATE: 1995-01-07
<313> RELEVANT RESIDUES: (1)..(1490)

<400> SEQUENCE: 1
ggacgctgga ttagaaggca gcaaaaaaag atctgtgctg gctggagccc cctcagtgtg        60

```
caggcttaga gggactaggc tgggtgtgga gctgcagcgt atccacaggc cccagg atg      119
                                                             Met
                                                             1 cag gcc ctg gtg cta ctc ctc tgc att gga gcc ctc ctc ggg cac agc       167
Gln Ala Leu Val Leu Leu Leu Cys Ile Gly Ala Leu Leu Gly His Ser
        5                   10                  15 agc tgc cag aac cct gcc agc ccc ccg gag gag ggc tcc cca gac ccc       215
Ser Cys Gln Asn Pro Ala Ser Pro Pro Glu Glu Gly Ser Pro Asp Pro
            20                  25                  30 gac agc aca ggg gcg ctg gtg gag gag gag gat cct ttc ttc aaa gtc       263
Asp Ser Thr Gly Ala Leu Val Glu Glu Glu Asp Pro Phe Phe Lys Val
        35                  40                  45 ccc gtg aac aag ctg gca gcg gct gtc tcc aac ttc ggc tat gac ctg       311
Pro Val Asn Lys Leu Ala Ala Ala Val Ser Asn Phe Gly Tyr Asp Leu
50                  55                  60                  65 tac cgg gtg cga tcc agc atg agc ccc acg acc aac gtg ctc ctg tct       359
Tyr Arg Val Arg Ser Ser Met Ser Pro Thr Thr Asn Val Leu Leu Ser
                70                  75                  80 cct ctc agt gtg gcc acg gcc ctc tcg gcc ctc tcg ctg gga gcg gac       407
Pro Leu Ser Val Ala Thr Ala Leu Ser Ala Leu Ser Leu Gly Ala Asp
            85                  90                  95 gag cga aca gaa tcc atc att cac cgg gct ctc tac tat gac ttg atc       455
Glu Arg Thr Glu Ser Ile Ile His Arg Ala Leu Tyr Tyr Asp Leu Ile
        100                 105                 110 agc agc cca gac atc cat ggt acc tat aag gag ctc ctt gac acg gtc       503
Ser Ser Pro Asp Ile His Gly Thr Tyr Lys Glu Leu Leu Asp Thr Val
    115                 120                 125 act gcc ccc cag aag aac ctc aag agt gcc tcc cgg atc gtc ttt gag       551
Thr Ala Pro Gln Lys Asn Leu Lys Ser Ala Ser Arg Ile Val Phe Glu
130                 135                 140                 145 aag aag ctr cgc ata aaa tcc agc ttt gtg gca cct ctg gaa aag tca       599
Lys Lys Xaa Arg Ile Lys Ser Ser Phe Val Ala Pro Leu Glu Lys Ser
                150                 155                 160 tat ggg acc agg ccc aga gtc ctg acg ggc aac cct cgc ttg gac ctg       647
Tyr Gly Thr Arg Pro Arg Val Leu Thr Gly Asn Pro Arg Leu Asp Leu
            165                 170                 175 caa gag atc aac aac tgg gtg cag gcg cag atg aaa ggg aag ctc gcc       695
Gln Glu Ile Asn Asn Trp Val Gln Ala Gln Met Lys Gly Lys Leu Ala
        180                 185                 190 agg tcc aca aag gaa att ccc gat gag atc agc att ctc ctt ctc ggt       743
Arg Ser Thr Lys Glu Ile Pro Asp Glu Ile Ser Ile Leu Leu Leu Gly
    195                 200                 205 gtg gcg cac ttc aag ggg cag tgg gta aca aag ttt gac tcc aga aag       791
Val Ala His Phe Lys Gly Gln Trp Val Thr Lys Phe Asp Ser Arg Lys
210                 215                 220                 225 act tcc ctc gag gat ttc tac ttg gat gaa gag agg acc gtg agg gtc       839
Thr Ser Leu Glu Asp Phe Tyr Leu Asp Glu Glu Arg Thr Val Arg Val
                230                 235                 240 ccc atg atg tcg gac cct aag gct gtt tta cgc tat ggc ttg gat tca       887
Pro Met Met Ser Asp Pro Lys Ala Val Leu Arg Tyr Gly Leu Asp Ser
            245                 250                 255 gat ctc agc tgc aag att gcc cag ctg ccc ttg acc gga agc atg agt       935
Asp Leu Ser Cys Lys Ile Ala Gln Leu Pro Leu Thr Gly Ser Met Ser
        260                 265                 270 atc atc ttc ttc ctg ccc ctg aaa gtg acc cag aat ttg acc ttg ata       983
Ile Ile Phe Phe Leu Pro Leu Lys Val Thr Gln Asn Leu Thr Leu Ile
    275                 280                 285 gag gag agc ctc acc tcc gag ttc att cat gac ata gac cga gaa ctg      1031
Glu Glu Ser Leu Thr Ser Glu Phe Ile His Asp Ile Asp Arg Glu Leu
```

-continued

```
           290                 295                 300                 305
aag acc gtg cag gcg gtc ctc act gtc ccc aag ctg aag ctg agt tac    1079
Lys Thr Val Gln Ala Val Leu Thr Val Pro Lys Leu Lys Leu Ser Tyr
                    310                 315                 320 gaa ggc gaa gtc acc aag tcc ctg cag gag atg aag ctg caa tcc ttg    1127
Glu Gly Glu Val Thr Lys Ser Leu Gln Glu Met Lys Leu Gln Ser Leu
                325                 330                 335 ttt gat tca cca gac ttt agc aag atc aca ggc aaa ccc atc aag ctg    1175
Phe Asp Ser Pro Asp Phe Ser Lys Ile Thr Gly Lys Pro Ile Lys Leu
            340                 345                 350 act cag gtg gaa cac cgg gct ggc ttt gag tgg aac gag gat ggg gcg    1223
Thr Gln Val Glu His Arg Ala Gly Phe Glu Trp Asn Glu Asp Gly Ala
        355                 360                 365 gga acc acc ccc agc cca ggg ctg cag cct gcc cac ctc acc ttc ccg    1271
Gly Thr Thr Pro Ser Pro Gly Leu Gln Pro Ala His Leu Thr Phe Pro
370                 375                 380                 385 ctg gac tat cac ctt aac cag cct ttc atc ttc gta ctg agg gac aca    1319
Leu Asp Tyr His Leu Asn Gln Pro Phe Ile Phe Val Leu Arg Asp Thr
                    390                 395                 400 gac aca ggg gcc ctt ctc ttc att ggc aag att ctg gac ccc agg ggc    1367
Asp Thr Gly Ala Leu Leu Phe Ile Gly Lys Ile Leu Asp Pro Arg Gly
                405                 410                 415 ccc taa tatcccagtt taatattcca atacctaga agaaacccg agggacagca       1423
Pro gattccacag gacacgaagg ctgcccctgt aaggtttcaa tgcatacaat aaaagagctt   1483
tatccct                                                             1490
```

<210> SEQ ID NO 2
<211> LENGTH: 418
<212> TYPE: PRT
<213> ORGANISM: Homo sapiens
<220> FEATURE:
<221> NAME/KEY: misc_feature
<222> LOCATION: (148)..(148)
<223> OTHER INFORMATION: The 'Xaa' at location 148 stands for Leu.

<400> SEQUENCE: 2

```
Met Gln Ala Leu Val Leu Leu Cys Ile Gly Ala Leu Leu Gly His
1               5                   10                  15

Ser Ser Cys Gln Asn Pro Ala Ser Pro Glu Glu Gly Ser Pro Asp
                20                  25                  30

Pro Asp Ser Thr Gly Ala Leu Val Glu Glu Asp Pro Phe Phe Lys
            35                  40                  45

Val Pro Val Asn Lys Leu Ala Ala Val Ser Asn Phe Gly Tyr Asp
        50                  55                  60

Leu Tyr Arg Val Arg Ser Ser Met Ser Pro Thr Thr Asn Val Leu Leu
65                  70                  75                  80

Ser Pro Leu Ser Val Ala Thr Ala Leu Ser Ala Leu Ser Leu Gly Ala
                    85                  90                  95

Asp Glu Arg Thr Glu Ser Ile Ile His Arg Ala Leu Tyr Tyr Asp Leu
                100                 105                 110

Ile Ser Ser Pro Asp Ile His Gly Thr Tyr Lys Glu Leu Leu Asp Thr
            115                 120                 125

Val Thr Ala Pro Gln Lys Asn Leu Lys Ser Ala Ser Arg Ile Val Phe
        130                 135                 140

Glu Lys Lys Xaa Arg Ile Lys Ser Ser Phe Val Ala Pro Leu Glu Lys
145                 150                 155                 160
```

```
Ser Tyr Gly Thr Arg Pro Arg Val Leu Thr Gly Asn Pro Arg Leu Asp
            165                 170                 175

Leu Gln Glu Ile Asn Asn Trp Val Gln Ala Gln Met Lys Gly Lys Leu
        180                 185                 190

Ala Arg Ser Thr Lys Glu Ile Pro Asp Glu Ile Ser Ile Leu Leu Leu
    195                 200                 205

Gly Val Ala His Phe Lys Gly Gln Trp Val Thr Lys Phe Asp Ser Arg
210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
                245                 250                 255

Ser Asp Leu Ser Cys Lys Ile Ala Gln Leu Pro Leu Thr Gly Ser Met
            260                 265                 270

Ser Ile Ile Phe Phe Leu Pro Leu Lys Val Thr Gln Asn Leu Thr Leu
        275                 280                 285

Ile Glu Glu Ser Leu Thr Ser Glu Phe Ile His Asp Ile Asp Arg Glu
    290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
        355                 360                 365

Ala Gly Thr Thr Pro Ser Pro Gly Leu Gln Pro Ala His Leu Thr Phe
    370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro

<210> SEQ ID NO 3
<211> LENGTH: 379
<212> TYPE: PRT
<213> ORGANISM: Homo sapiens

<400> SEQUENCE: 3

Met Asn Arg Ile Asp Phe Phe Phe Lys Val Pro Val Asn Lys Leu Ala
1               5                   10                  15

Ala Ala Val Ser Asn Phe Gly Lys Asp Leu Tyr Arg Val Arg Ser Ser
            20                  25                  30

Met Ser Pro Thr Thr Asn Val Leu Leu Ser Pro Leu Ser Val Ala Thr
        35                  40                  45

Ala Leu Ser Ala Leu Ser Ser Gly Ala Glu Gln Arg Thr Glu Ser Ile
    50                  55                  60

Ile His Arg Ala Leu Tyr Tyr Asp Leu Ile Ser Ser Pro Asp Ile His
65                  70                  75                  80

Gly Thr Tyr Lys Glu Leu Leu Asp Thr Val Thr Ala Pro Gln Lys Asn
                85                  90                  95

Leu Lys Ser Ala Ser Arg Ile Val Phe Glu Lys Lys Leu Arg Ile Lys
            100                 105                 110
```

```
Ser Ser Phe Val Ala Pro Leu Glu Lys Ser Val Gly Thr Arg Pro Arg
        115                 120                 125

Val Leu Thr Gly Asn Pro Arg Leu Asp Leu Gln Glu Ile Asn Asn Trp
130                 135                 140

Val Gln Ala Gln Met Lys Gly Lys Leu Ala Arg Ser Thr Lys Gln Ile
145                 150                 155                 160

Pro Asp Glu Ile Ser Ile Leu Leu Leu Gly Val Ala His Phe Lys Gly
                165                 170                 175

Gln Trp Val Thr Lys Phe Asp Ser Arg Lys Thr Ser Leu Glu Asp Phe
            180                 185                 190

Tyr Leu Asp Glu Glu Arg Thr Val Arg Val Pro Met Met Ser Asp Pro
        195                 200                 205

Lys Ala Val Leu Arg Tyr Gly Leu Asp Ser Asp Leu Ser Cys Lys Ile
210                 215                 220

Ala Gln Leu Pro Leu Thr Gly Ser Met Ser Ile Ile Phe Phe Leu Pro
225                 230                 235                 240

Leu Lys Val Thr Gln Asn Leu Thr Leu Ile Glu Glu Ser Leu Thr Ser
                245                 250                 255

Glu Phe Ile His Asp Ile Asp Arg Glu Leu Lys Thr Val Gln Ala Val
            260                 265                 270

Leu Thr Val Pro Lys Leu Lys Leu Ser Tyr Glu Gly Glu Val Thr Lys
        275                 280                 285

Ser Leu Gln Glu Met Lys Leu Gln Ser Leu Phe Asp Ser Pro Asp Phe
    290                 295                 300

Ser Lys Ile Thr Gly Lys Pro Ile Lys Leu Thr Gln Val Glu His Arg
305                 310                 315                 320

Ala Gly Phe Glu Trp Asn Glu Asp Gly Ala Gly Thr Thr Pro Ser Pro
                325                 330                 335

Gly Leu Gln Pro Ala His Leu Thr Phe Pro Leu Asp Tyr His Leu Asn
            340                 345                 350

Gln Pro Phe Ile Phe Val Leu Arg Asp Thr Asp Thr Gly Ala Leu Leu
        355                 360                 365

Phe Ile Gly Lys Ile Leu Asp Pro Arg Gly Pro
    370                 375

<210> SEQ ID NO 4
<211> LENGTH: 14581
<212> TYPE: DNA
<213> ORGANISM: Homo sapiens

<400> SEQUENCE: 4
gatctagagc ggccgcaggg tggactgtgc tgaggaaccc tgggcccagc agggtggcag      60
cccgcgcagt gccacgtttg gcctctggcc gctcgccagg catcctccac cccgtggtcc     120
cctctgacct cgccagccct cccccgggac acctccacgc cagcctggct ctgctcctgg     180
cttcttcttc tctctatgcc tcaggcagcc ggcaacaggg cggctcagaa cagcgccagc     240
ctcctggttt gggagaagaa ctggcaatta gggagtttgt ggagcttcta attacacacc     300
agcccctctg ccaggagctg gtgcccgcca gccgggggca ggctgccggg agtacccagc     360
tccagctgga cagtcagt gcctgaggat ttggggaag caggtgggga aaccttggca       420
cagggctgac accttcctct gtgccagagc ccaggagctg gggcagcgtg ggtgaccatg     480
tgggtgggca cgcttccctg ctgggggtgc agggggtcca cgtggcagcg gccacctgga     540
gccctaatgt gcagcggtta agagcaagcc cctggaagtc agagaggcct ggcatggagt     600
```

-continued

```
cttgcttctt gcaaacgagc cgtgtggaga gagagatagt aaatcaacaa agggaaatac      660
atggtctgtc cgaggatgag ctgccggaga gcaatggtga aagtgaagtg ggggagggg       720 cggggctggg aggaaaagcc ttgtgagaag gtgacacgag agcacggcct tgaagggaa       780 gaaggagggc actatggagg tcccggcgaa gcgtggcctg gccgaggaac ggcatgtgca      840
gaggtcctgc cgaggagctc aagacaagta ggggacggtg gggctggagt ggagagagtg      900
agtgggagga ggagtaggag tcagagagga gctcaggaca gatcctttag gctctaggga      960
cacgataaac acagtgtttt ttgtcttgtc aagtgtgtcc tttttatttt tttgaaagag     1020
tctcgctctg tagcccaggc tggagtgcag cggtgcgacc tcggctcagt gcaacctctg     1080
cctcccgggt ccaagcaatt ctcctgcctc agcctcccga gtagctggga ttacaggcac     1140
ccgccaccac gcactgctaa ttttttgtatt ttagtagaga ccgggttttg ccatgttggt    1200
caggctggtc tcgaactcct gacctcaggt gatccgcccg cctcggcctc ccagagtggt     1260
gtgagccact atgccctgca gcacttgtca agtctttctc agcgttcccc tcctctccac     1320
tgcagctccc agtgccccag tctgggcctc gtcttcactt cctgggatcc ctgacattgc     1380
ctgctaggct ctccctgtct ctggtctggc tgccttcact gtaacctcca cccagcaggt     1440
acctcttcag cacctcccat gaacccagca gaataccaag ccctggggat gcagcaacga     1500
acaggtagac gctgcactcc agcctgggcg acagagcaag actccgcctg aagaaaaaaa     1560
aaaggaccag gccgggcgcg gtggctcacg cctgtaatcc cagcactttg ggaggccgag     1620
gtgggtggat catgaggtca ggagttcaag accagcctgg caaaaatggt gaaacccgt      1680 ctctactgaa aaatacaaaa attagctggg tgcagtggcg ggcgcctgta gtctcagcta     1740
ctcaggaggc tgaggcagga taattgcttg accccaggag gcagaggttg cagtgaaccg     1800
agatcacgcc actgcactcc agcctgggcg acagagcaag actctgcctc aaaaaaaaga    1860
ataaaaataa aaaaaggac cagatacaga aaacagaagg agacgtacta tgaaggaaat      1920
tggagagctt ttgggatact gagtaactca gggtggcctt tcccagggga catttagctg     1980
agagatagac ggtatgaaga cctgaccgtt cagaaacagg ggaagaggca gcagcccggg    2040
caaaggcctt tggggcagga aagggcttgg atcactggag aagcagaaag atggccagtg     2100
tgaccagagt gtgacaaagt cagagaaaac caggaagatg gagctggaga cacaggcggg     2160
gccagatcac gagggtcctc gcagaccaga gcaagggttt ggattttatt ccaagtatga     2220
agggaagctg ctgaagtgtg ttttcccttta caatttgtag ttgaaatata atatgcaaag    2280
tacacaagtc ttaactatat gtaagcttaa tgaatgtttc catgaaccaa ataccgctgt     2340
gcaaccatca ccagctcaag agacgaaccc ttctccctcc tcctgactgc cagtaacata     2400
gtggttcagc tcaagaaaca gaactcttct gacttcccct aacatagcgg ttttctttt     2460 ttgttttgtt tttgttgtt ttttaagaga caatgtcttt attatttta ttttttttta     2520 tttttgagac ggagtcttgc tgtcgcccag gctggagtgc agtggtgcga tctcggctca    2580
ctgcaggctc tgccccccgg ggttcatgcc attctcctgc ctcagcctcc ctagcagctg     2640
ggactacagg tgcccgccac ctcgcccggc tattttttg tatttttagt ggagacgggg     2700
tttcaccgtg ttagccagga tggtctcgat ctcctgacct cgtgatccgc ccacctcggc    2760
ctcccaaagt gctgggatta caggcatgag ccaccgcgcc cagccaagag acacggtctt    2820
gctctgtcgc ccaggctgga tggagtgccg tggtgcgatc acagctcgcg gcagccttga   2880
catcctgggc tcaagcaacc ttcctgcctt ggctcccaa atgttgggat tataggcatg     2940
agccactgtg cttggcatct attcatcttt aatgtcaagc aggcaattga atatttgatc    3000
```

```
agggatagaa ttgtctattt gggggtatgc agatgtgctt catgtcatgg aactgggccg    3060
ggcgcggtgg ctcatgccta taatcccagc actttgggag gccgaggcag gcggatcata    3120
aggtcaggag atcgagacca tccgggccaa caggtgaaac cccgtctctt actaaaaata    3180
caaaaattag gcaggtgtgg tggtgcgtgc ctgtagtccc agctactcag ggaggctgag    3240
acaggagaat tgattgaacc tgggaggcag aggttgtagt gagccaagat cgcgccactg    3300
cactccagcc tgggcgacat gagcgagact ccgtctcaaa aataaacaaa aaaagtcat    3360 ggaattgatg gaaattgcct aaggggagat gtagaagaaa aggggtctca ggatcaagcc    3420
agcagagaag gcagaaaagg taaggtgtgt gaggtggcag aaaaagggaa gagtgtggac    3480
agtgagggtt tcaaggagga ggaactgtct actgcctcct gccaaggacg gaggtgtcca    3540
ctgccagttg acataaggtc acccatgaac ttggtgacag gaatttcagt ggagaagtgg    3600
ccacagacac aagtctagaa ttgaaatggg agccgaggca gcgtagacaa aagaggaaac    3660
tgctccttgc agagcggctc tgagcgagca ccgagaaatg ggcagtggct ttaggggatg    3720
tagcgtcaag gaagtgtctt ttaaagaagt cgggggccgg gcacggtggc tcacgcctgt    3780
agtcccagca ctttgggagg ccgaggcagg cagatcactt gaggtcagga gttcgagacc    3840
agcctggcta acacgatgaa accccgtctc tactaaaaat acaaaaaatt agctgggcac    3900
ggtggctcgt gcctgtaatc ccagcacttt gggaggcaga ggtgggcaga tcacttgagg    3960
tcaggagttt gagaccagcc tagcaacat ggtgaaaccc catctctact aaaactacaa    4020
aaattagccg ggagtggtgg cacgtgcctg taatcccagc cagtcaggag gctgaggcag    4080
gagaatcact ggaatcctgg aggtggaggt ggcagtgagc cgagatggta cctctgtact    4140
ccagcctggg ggacagagtg agactccgtc tcaaaaaaaa aagaaggtgg ggaaggatct    4200
ttgagggccg gacacgctga ccctgcagga gaggacacat tcttctaaca ggggtcggac    4260
aaaagagaac tcttctgtat aatttatgat tttaagattt ttatttatta ttatttttta    4320
tagaggcaag cattttttcac cacgtcaccc aggctggtct ccaactcctg ggctcaagtg    4380
tgctgggatt atagccatga gtcaccacac ctggcccaga aacttactaa aggacttatt    4440
taaatgattt gcttatttgt gaataggtat tttgttcacg tggttcacaa ctcaaaagca    4500
acaaaaagca cccagtgaaa agccttcctc tcattctgat ttccagtcac tggattctac    4560
tcttgggatg cagtgttttt catctctttt ttgtatcctt ttggaaatag tattctgctt    4620
taaaaagcaa ttacaggcca ggtatggtgg ctcactcctg taatcccagc actttgggag    4680
gccgaggcag gtgatcacct aaggtcagga gttcaagacc agcctggcca atatggtgaa    4740
accctgtctg taccaaaaga caaaacaaa aacaaaaaca aaaattagcc gggcgtggtg    4800
gcgtgctcct gtaatcccag ctactcagga ggctgaggca ggagaatcgc ttgaacctgg    4860
gaggcagagg ttgcagtgag ccgagattgt gccactgtac tccagcctgg gccacagagc    4920
aaggttccat ctcaaacaaa acaaaacaaa acaaacaaaa aaacaaaaca aaagctaata    4980
caaacacata tacaatagac aaaactgtaa atattttatt attttttattt tttttagtag    5040 agacagggtt tcaccatgtt ggccaggatg gtctcaaact cctgacctca ggtgatccac    5100
ccacctcagc ctcccgatag ttaggattac aggcatgagc caccacccc ggcctaaaat    5160 tgtaaacgtt ttagaagaaa gtatagatga atcccttcgt gatctcgggg aagaagagat    5220
tttttaaaaa agataccaaa agaagcacaa attataaaag aaaagattga aaatgttggt    5280
gttaaaatta aaaacttgtt ttaaaacaag cttgtgtaac ccatgaccca caggctgcat    5340
```

-continued

```
gtggcccaga aaagctttga ctgcagccca acacaaattc gtaaactttc ctaaaacatt   5400
atgagatttt ttttgagatt ttgttttgtt ttgtttttg ttttttttagc tcattcggta   5460
tcattaatgt tagcatattt tacgtggggc ccaagacaat tcttcttcca atgtgtctca   5520
ggggagccaa aagattggac acccctgcca taaacatgaa aagacaatgg ccgggcacgg   5580
tggctcacgc ctgtaatccc agcactttgg gaggctgagg ggggcgggat cacctgaggt   5640
caggagtttg agacaagcgt gaccaatgtg gtgaaaccct gtctctacta aaaatacaaa   5700
aattagccgg gcatgctcgt gcacacctat agtcccaact actcagcagg gtgaggcagg   5760
agaacctctt gaacccggga gcggaggtt gcagtgagcc gacattgcac ccctgcactc   5820
gagcctgggt gacagagtga gtctccactg aaaaaaaaa aaaagaaca gtgtgataca   5880
ttgacctaag gtttaagaac atgcaaactg atactatata tcacttaggg acaaaaactt   5940
acatggtaaa agtaaaaaga aatgtacgaa aataataaaa atcaaattca agatggtggt   6000
tatggtgacg ggaagaact gaggcggaaa tataaggttg tcactatatt gagaaatttt   6060
tctatctttt ttttctttt tcttttttga cacgggtct cgctctgtcg cccaggatgg   6120
agtgcagtgg tgtgatctca gctcactgca acctccgcct cccaggttta agtgattctc   6180
ctgcctcaga ctcccaagta gctgggacta caggtgcgcg ccaacacacc tgggtaattt   6240
tgtttgtatt tttagtagag atggggtttc accgtgttga ctaggctggt ctcgaactcc   6300
tgacctcagg tgatccccg gcctcggtct cccaaagtgc tgggataaca agcgtgagcc   6360
actgcgccca gctttgtttg cattttagg tgagatgggg tttcaccacg ttggccaggc   6420
tggtcttgaa ctcctgacct caggtgatgc acctgcctca gtctcccaaa gtgctggatt   6480
acaggcgtta gccctgcgc ccggcccctg aaggaaaatc taaaggaaga ggaaggtgtg   6540
caaatgtgtg cgccttaggc gtaatggatg gtggtgcagc agtgggttaa agttaacacg   6600
agacagtgat gcaatcacag aatccaaatt gagtgcaggt cgctttaaga aaggagtagc   6660
tgtaatctga agcctgctta tggacgctgg attagaaggc agcaaaaaaa gctctgtgct   6720
ggctggagcc ccctcagtgt gcaggcttag agggactagg ctgggtgtgg agctgcagcg   6780
tatccacagg taaagcagct ccctggctgc tctgatgcca gggacggcgg gagaggctcc   6840
cctgggctgg ggggacaggg gagaggcagg ggcactccag ggagcagaaa agaggggtgc   6900
aagggagagg aaatgcgaga cagcagcccc tgcaatttgg ggcaaaaggg tgagtggatg   6960
agagagggca gagggagctg gggggacaag gccgaaggcc aggacccagt gatccccaaa   7020
tcccactgca ccgacggaag aggctggaaa ggcttttgaa tgaagtgagt gggaaacagc   7080
ggagggcggg tcatggggag gaaaggggag ctaagctgct gggtcgggtc tgagcagcac   7140
cccaagactg gagcccgagg caaggaggct cacgggagct gcttccacca agggcagtca   7200
ggaaggcggc cgccctgcag cccagccctg gcccctgctc cctcggctcc ctgctacttt   7260
ttcaaaatca gctggtgctg actgttaagg caatttccca gcaccaccaa accgctggcc   7320
tcggcgccct ggctgagggc tgggatggag gacagctggg tccttctagc cagccccac   7380
ccactctctt tggctacatg agtcaaggct gggcgaccaa tgaggttgtg gcctccggca   7440
aacaatgacc actatttagg ccggcaggtg tataggcgt gggggcccag ctgccagtgc   7500
tggagacaag ggctgtccga gatgaaccct ttctgctgcc tgccaagcca ctgggagggg   7560
taggtctcag caggattccc agaaaccccg ccctgtcca gcctaggccc cccacccggt   7620
gttagctaac ccaacgttag cccccaggtt ccgtgggtt ggggggcagg gagtcctatt   7680
cttggggctg ctgcttctgg ggtgtgggga agtgcaactc cacggcaccc tgggctgact   7740
```

```
cattcagctt ctaaagcttc aggaaacatt gtttggggct gggtcaccat gggtgggcca    7800
gagaggaccc ctcaatcccc tccggagagc caggggaggg ggaggtgccc ttccccatgc    7860
tatctccgag gccactgcca tgtggcctga aggctgtgcg gttctgggaa gaggggggagg   7920 tggcggtgga ggctgtttgt ctcctaactg gcttaatct gaaacacatg tattggcttg     7980
agttgatccg cctcacgtgg aggcaagatc acaaaagctt ctgtgtttct tgatgtgggc    8040
aattgtcaga aaataaggcc tgaccttggc ccagcaggga gggtatctac ctctccctga    8100
gccctccccc gcctgctagg acgagagcgg ggccttggata ctgcccttg gacaggatgg   8160 catcattgtc tgtggctgca gccagccagc ggtcgcctgc tcagcccatg agcaaccact    8220
gtggacaggg tattgcgtgt gtgctgaggg gcgtccatgc agaccccac gcttgccctc     8280 tcactgccct tgtagggttt tcaatcatct ctcctcttcc cttatccaga tggcttgaag    8340
tggaggattc agacttgccg ttaatactct gggtccctgt gtctagctcg ggccacctt     8400 tggacccatg tcccttccct gccaggctcc ctcacctcac ctcagcctac ccacattgtg    8460
acaatcatct accacctgat ctgggggtttg ggcttagatt ctgtaggcac caagactaaa   8520
gtcgctcctt caagtccatt tgaattgtga ctttagtttc cttaaatact atgccaggat    8580
aatggccagg gatggtggct cacgcctgta ctccctggcac tttgggatgc tggtggatca   8640
cctgagatca ggattccagg ccagcctggc caacacggtg aaaccccatc tctactaaaa    8700
cataaaaatt aaccaggtgt ggtggcgggc acctgtaatc ccagctactc aggagactga    8760
ggcaggagaa ttgcttgaac ccgggaggtg gaagttgcac tgagctgaga tcgcgccact    8820
gcactttagc ctgggcgaca agagtgaaac tctgtctcaa aaacaaaaaa aactatgccg    8880
ggatgagcct gtcctctccc ttaatttctt acttgggcca gaggaactag aactaacaac    8940
ttctcttcta gccttgcctc ctgtgtacct cactgaattt ttggtctcta ataaaccagt    9000
ctgcagaggc tcaggggagg caggctcctg gcagctgggt ggggctggcc ccagccgggt    9060
ggagaccagc tgtaggcctg gatggtggtg aggcctctgt cttgcactgc agaaagcttt    9120
tcctgttgtc tacacgaaag ttttctcct gcatgtcagg gcagccacgt gcaagagcag    9180
ctggctggga acgcagaggt ctgcggctcg aggcggggtt tagaaaggaa aaccaggctg    9240
cttcctgctg cccgtcctgc cttaagctga gtaaactcaa aggcaatctt ctttcatgcc    9300
tcacgatatt gtccagtgga ttatctgatt taatttgaag gacgagagcc aacaatcaca    9360
caacgtcctc ccaaattttc tgatccactt tgttctggga agtcaaaaag tgcgtgtgct    9420
gtgtgggtgg atgtttgtga tataaatgga taatgaagga tgatgtgttg gggggccagg    9480
gcagggagaa caacgctgtt cagattctac atttttttttt cctttttttt ttttttttga    9540
gatggagtct tgctctgttg cccagcctgg agtgcagtgg cgcgatctca gctcactgca    9600
acctccactt cctggattca agtgattctc ctgccttagc ctcccaagta gctgggatta    9660
caggcatgcg ccaccacacc cggctaattt ttgtatttttt agtagagatg gggtttctcc    9720
atgttggcca ggatggtctc aaactcctga cctcaggtga tctacccgcc tcggcctctc    9780
aaagtgctgg gattacaggt ttgagccact gcgcctggcc tttttttttt ttttttgagat    9840 ggagttttca ctcttgttgc ccaggctgga gtgcagtggc gcgatcttgg ctcactgcaa    9900
cctccacctc ccaagttcaa gtgattctcc agccttagcc tccaagtag ctgggactac     9960 aggtgtgtgc caccatgcct ggctatttta ttttatttta ttttatttat ttatttttga   10020
gactaagtct tgctctgttg cccaggctgg agtgcagtgg cataatcggc tcactgcaac   10080
```

```
ctctgcctcc caggttcaag tgattctcct gcctcagcct cctgagtaac tgggattaca    10140
ggggcctgcc accacgcctg gctacttttt gtattttag tatagatggg gtttcaccat    10200
gttggccagg ctggtctcga actcctgacc tcaggctatc cgcctgcctc agcctcccaa    10260
aagtgctggg attacaggca tgagccactg tgctcggtag ttgtttattt taatagtagg    10320
ttattttatt tccattttac aagagaaaaa atggtgattt aaagagctac taagacacag    10380
cactgagacc atgtgtgatg gcatgcgcct gcagtcccag ctactcacga ggctgaggca    10440
ggaggatcac atgaggtcag gagttccagg ctgtggagtg ctatggttgt gtagtgaata    10500
gccactacac tccagcctgg gcagcacagc aagatcttgt ctcccaaaaa aaaaaaaaa    10560 aaaaaatttc aaatgtgaac ccaggatctc tgaccgggct aggccctgca ctgctaacca    10620
tgggaggaag agctcttgaa agggaactgt gggagaaggg aatgagctgc cttgtgaggc    10680
cacagaagtc caaagacagc ttgagaattt ggaggacagc acgtgccgga ctggggtgcc    10740
tctatgcttg gtatccggtg attccatgga ggagacctgg gttctgcccc attctcctgg    10800
gaggggttgc ccaaagtctt atcaccggag tgggtcagct gcctccagga caaagcttta    10860
gcatacactt gtgctgggcc atactccacg tggagaagcc ctgctggggc tggggccccca    10920 ctgctctgga tctttaaaag ctattggttc aggggccagg tgtaatggct cacacctata    10980
accctagcac tttgggaggc tgaagcaggt ggatagcctg aggtcaggag tttgagacaa    11040
gcctgatgac gtggtgaaac cccatcgcta ttaaaaatac aaaaaattag ccgggcatgg    11100
tggcaggtgc ctgtaattcc agctacttgg gaggctgagg cgggagaatc gcttgaaccc    11160
aggaggcgga ggttgcagtg agccaagatc gctccactgt actccagcct gggcgacaga    11220
gccagactct gtttcaaaaa ataaaatata aataaataaa taaataaata aataaataaa    11280
taaaagcttt aggcttaaag gagggtcccc tgacgcagac agtggaacaa agcacaagc    11340 ttatggtatg actgtgggcc ctgaggcagg ggaggggcg ggagaacctt gctgggaggg    11400
atgggccatc aagctgaggg tccacttctg ggggcctgga ggggtgaggg gtggtcgctg    11460 caggggtgg gggaaagtga ctaacccctg ggtcctggct gggcctggct ggggtggcca    11520
ggaaggggta gcggggcagt gcagtgtcgg gggagagcgg cttgctgcct cgttcttttc    11580
ttgcaggccc caggatgcag gccctggtgc tactcctctg cattggagcc ctcctcgggc    11640
acagcagctg ccagaaccct gccagccccc cggaggtcag taggcaggcg ggagggcgt    11700 ggtcagcatt ccccgcccct ccttggcagg cagcacggga aacaggacag gaacccgga    11760 cccaggttcc aggccaggct tgggccttta tttctctagg gctggagttt ctccagcagc    11820
aaaacagaga gaaatgtct tgccttgcct ttcaggggat ggagtaggga catgaataag    11880
atcccaaaag agtaaaatc tgaagcactt ttaacaagtc cagggcaatt ctcctgcctc    11940
agcttcccaa gcagctggga ttacaggcat gcaccaccaa gcccggctca ttttgtattt    12000
ttagtagaga cggggtttct ccatgttggt caggctggtc tcgaactccc gacctcaagt    12060
gattctcctg cctcggcctc ccaaagtgcc gggatgacag gtgtgagcca ccgcacctgg    12120
ccaggatctt ttctcattac cttgtcttcc tagtggggc tccactgagc aggtcatgtt    12180
cccggacatt tgttcggata ctgaccaggc tgtggcaggg agtgagggta tggagtgacc    12240
tctctcctgc ccagaaaggg cgcagctggg ttcccaaggc agatacaggc acatggaggg    12300
aagcctgggc catatgagtg ttatggggtg agtgttggcg gaggcccacc cttgagggac    12360
aagagcagct gggcatcttg gcgagagccc tggactttcg tgaggtcaga gtatgaattc    12420
tgcgtctccc tcttcctagc tttgtgaccc tagacaaccc ttacctcagt ctttgcttcc    12480
```

```
ttgcctatga aatgggataa aaacacccat tctacagggc catgtggcca ctcatttatt    12540
tctcatctac caaacaccta ctcgacaggg gctggcaatg ggcggaaata aaaactcagt    12600
tctgccgggt gcggtggctc acacctgtaa tcccagcagt gtgggaggcg gagcaggacg    12660
atcccttgaa tccaggagtt tgagaccagc ataggcaaca tagtgagacc cctgtctcta    12720
cacaaaagca aaaattacca ggcgtggtgg caagtgcttg tggtactacc tacttgggaa    12780
gctgaggtgg gaggatcact tgagcccagg agattaagac tgcagtgagg gccgggcgc     12840 ggtggctcac gcctgtaatc ccagcacttt gggaggtgga ggtgggtgga tcacgaggtc    12900
aggagatcga gaccatcctg gctaacacgg tgaaacccccg tctctactaa aaatacaaaa    12960
aattagctgg gtgtggtggg gggcgcctgt agtcccagct actcgggagg ctgaggcagg    13020
agaatggcgt gaacccggga ggtggaggtt gcagtgagct gagctcgcac cactgcactc    13080
cagcctgggc gacagagtga gactccgtct caaaaaaaaa aaaaaaagaa agaaagaaag    13140
aaaaactgag ttctttttttt taactttctt tttttagaga cagagtctca ctccatcacc    13200
catgctggag tacagtggtg cgatcttggc tcactgcaat cttggcctcc tgagttcaac    13260
caattctcat gcctcagcct cccaaatagc tgggaccaca ggcacgtgcc accacgccca    13320
gctaattttt tgggtatttt tagtagagat ggggcctcac catgttgctc aggttggtct    13380
gaaactcctg agctcaagtg atccatcttc ctcggcctgc caaagtgctg ggattatagg    13440
cataagccac tgcacctagc tcccaatttt tatatttata tttattttta tttacttatt    13500
tattttttga cagggtctc cactctgtca cccaggctgg agtacagtgg cactatctca    13560
gctcactgca acctctgcct cctgggttca agcgaatctc gtgcctcagc ctcctgagta    13620
gctgggatta caggcatgca ccaccatgcc ccgttaattt ttttgtattt ttagtagaga    13680
cgggtttcac cgtgttgccc aggatggtct cgaactcctg acctcaagtg attcacccac    13740
ctcagcctcc caaagtgctg ggattatagg tgtgagccac tcggctgatg gttttttaaaa   13800 agtgggtcat ggggctgggc gcggtggctc atgcctgtaa tcccagcact ttggtagacc    13860
gaggcgggtg gatcacaagg tcaggagatc gagaccatcc tgcctaacac ggtgaaaccc    13920
cgtctctact aaaaatacaa aaaattaccc aggcatggtg gtgggcgcct gtagtcccag    13980
ctactcggga ggctgaggca ggagaatggc gtgaacctgg gaggcggagc ttgcagtgag    14040
ccgagatcac gccaccgtac tccagcctga gcgacagagc gagactccgt ctcaaaaaaa    14100
aaaaaaaaaa gtgggtcata ggtttcggct tataggtcac aagtgtttaa acctggccat    14160
gaggccaggc gcagtggcgc atgcctgtaa tcccagccat ttgggaggct aaggcaggaa    14220
aatcgcttga accggggagg tggaggttgc agtgagctga gatcgcgcca ctgaactcta    14280
gcctgggtga cacagtaaga ctctgtctca aataaaaaaa aaaacagctg atctctcttc    14340
tgcgctgtct ctccacagag agctcatgcg tgatcaggga gtaaaactca ttcccgtttt    14400
aggccaaaca cagaaaaatt aggaaggaca gccccaaggg gccagaacca ccaccctaca    14460
caaagccgtg aggagacagt ccctgtgcat ctctgcgagt ccctgaactc aaacccaaga    14520
cttcctgtct cctgccaggg ctccccagac cccgacagca caggggcgct ggtggaggag    14580
g                                                                   14581
```

<210> SEQ ID NO 5
<211> LENGTH: 5262
<212> TYPE: DNA
<213> ORGANISM: Homo sapiens
<220> FEATURE:

```
<221> NAME/KEY: misc_feature
<222> LOCATION: (574)..(574)
<223> OTHER INFORMATION: n is a, c, g, or t
<220> FEATURE:
<221> NAME/KEY: misc_feature
<222> LOCATION: (582)..(584)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (991)..(991)
<223> OTHER INFORMATION: n is a, c, g, or t
<220> FEATURE:
<221> NAME/KEY: misc_feature
<222> LOCATION: (1335)..(1335)
<223> OTHER INFORMATION: n is a, c, g, or t
<220> FEATURE:
<221> NAME/KEY: misc_feature
<222> LOCATION: (1339)..(1339)
<223> OTHER INFORMATION: n is a, c, g, or t
<220> FEATURE:
<221> NAME/KEY: misc_feature
<222> LOCATION: (1378)..(1381)
<223> OTHER INFORMATION: n is a, c, g, or t
<220> FEATURE:
<221> NAME/KEY: misc_feature
<222> LOCATION: (1425)..(1425)
<223> OTHER INFORMATION: n is a, c, g, or t
<220> FEATURE:
<221> NAME/KEY: misc_feature
<222> LOCATION: (1507)..(1507)
<223> OTHER INFORMATION: n is a, c, g, or t
<220> FEATURE:
<221> NAME/KEY: misc_feature
<222> LOCATION: (1523)..(1523)
<223> OTHER INFORMATION: n is a, c, g, or t
<220> FEATURE:
<221> NAME/KEY: misc_feature
<222> LOCATION: (1773)..(1773)
<223> OTHER INFORMATION: n is a, c, g, or t
<220> FEATURE:
<221> NAME/KEY: misc_feature
<222> LOCATION: (1947)..(1947)
<223> OTHER INFORMATION: n is a, c, g, or t
<220> FEATURE:
<221> NAME/KEY: misc_feature
<222> LOCATION: (1958)..(1958)
<223> OTHER INFORMATION: n is a, c, g, or t

<400> SEQUENCE: 5
acaagctggc agcggctgtc tccaacttga atacaagctg gcagcggctg tctccaactt      60
cggctatgac ctgtaccggg tgcgatccag catgagcccc acgaccaacg tgctcctgtc     120
tcctctcagt gtggccacgg ccctctcggc cctctcgctg ggtgagtgct cagatgcagg     180
aagccccagg cagacctgga gaggcccccct gtggcctctg cgtaaacgtg gctgagttta    240
ttgacatttc agttcagcga ggggtgaagt agcaccaggg gcctggcctg ggggtcccag     300
ctgtgtaagc aggagctcag gggctgcaca cacacgattc cccagctccc cgaaaggggc     360
tgggcaccac tgacatggcg cttggcctca gggttcgctt attgacacag tgacttcaag     420
gcacattctt gcattcctta accaagctgg tgctagccta ggttcctggg atgtaactgc     480
aaacaagcag gtgtgggctt gccctcaccg aggacacagc tgggttcaca ggggaactaa     540
taccagctca ctacagaata gtcttttttt tttntttttt tnnncttttct gagacggagt    600 ctcgctttgt cnccaaggct ggagtgcagt ggtgtgatct cagctcactg caacctctgc     660
ctccctggtt caaggaattc tcctgcctca gcctccagag tagctgggat tacaggcacc     720
tgccatcatg cccagctaat ttttgtattt ttagtagaga cggggtttca ccatgttgcc     780
```

-continued

```
taggctggtc tcaaactccc gggctcaagc gatccacccg ccttggcctc ccaaagtgct    840
gggattacag gcgtgagcca ccgcgcctgg ccagaataat cttaagggct atgatgggag    900
aagtacaggg actggtacct ctcactccct cactcccacc ttccaggcct gatgccttta    960
acctacttca ggaaaatctc taaggatgaa nattccttgg ccacctagat tgtcttgaag   1020
atcagcctac ttgggctctc agcagacaaa aagatgagt atagtgtctg tgttctggga   1080
gggggcttga tttggggccc tggtgtgcag ttatcaacgt ccacatcctt gtctctggca   1140
ggagcggagc agcgaacaga atccatcatt caccgggctc tctactatga cttgatcagc   1200
agcccagaca tccatggtac ctataaggag ctccttgaca cggtcactgc ccccagaag   1260
aacctcaaga gtgcctcccg gatcgtcttt gagaagagtg agtcgccttt gcagcccaag   1320
ttgcctgagg catgngggnt ccatgctgca ggctggggg gtcttttttt ttttttnnn    1380
nagacggagt ctcgctctgt tgcccaggct ggagtgcagt ggcgngatct cggctcactg   1440
caacctccac ctcccgggtt cacaccatcc tcctgcctca gcctcccgag tagctgggac   1500
tgcaggngcc cagctaatct ttnttgtatt tttagcagag acggggtttc accgtgtttg   1560
ccaggatagt ctcgatctcc tgacctggtg ttctgcccgc ctcgacctcc caaagtgctg   1620
ggattacagg tgtgagccac cgcgctcggc ccgtttctaa acaatagatc atgtgtgccc   1680
aggcctggcc tggcactggt gtggaggaag ggcccgtgag cccaaagagg ctcagaaaga   1740
ggaagtgggc tgcaggagac ggtgggaggg gcngggaggg cagtggcgcg atgtggggaa   1800
atctgctgcc ccctggcca gtgcctgggg atgccagcag aagtcctggc aagtcacagg   1860
aagatgctgg ctgggaagtc agggcctgct gagcgctaaa ccagaacccg agcctggcag   1920
gctctcaaag acgggatgct tgtcgtngag tctcatangc taacctctgc tccgcctctt   1980
ctcagctacg cataaaatcc agctttgtgg cacctctgga aaagtcatat gggaccaggc   2040
ccagagtcct gacgggcaac cctcgcttgg acctgcaaga gatcaacaac tgggtgcagg   2100
cgcagatgaa agggaagctc gccaggtcca caaaggaaat tcccgatgag atcagcattc   2160
tccttctcgg tgtggcgcac ttcaagggtg agcgcgtctc caattctttt tcatttattt   2220
tactgtattt taactaatta attaattcga tggagtctta ctctgtagcc ctaactggag   2280
tgcagtggtg cgatctcagc tcaatgcaac ctccgcctcc caggttcaag caattcttgt   2340
gcctcagcct cccgagtagc tgggattaca gggatgtacc accactcccg gctaattttt   2400
tgtatttaat agacatgggg tttcaccatg ttggccaggc tggtctcgaa ctcctgagct   2460
caggtggtct gcccgcctca gcctcccaaa gtgctaggat tacaagcttg agccaccacg   2520
cccagcccctt tttattttta aattaagaga caaggtgttg ccatgatgcc caggctggtc   2580
tcgaactcct gggctcaagt aatcctccca ccttggcctc ccaaagtgct gggattacag   2640
gcatgagcca ccgcgcccgg ccctttacca tttatttatt tatttttga cagagtctct   2700
tgctctgtca cccaggctgg agtgcagtgg cgcgatctcg gctcactgca agctctgcct   2760
tccaggttca ccattctc ctgcctcgac tcccgagta gctgggacta caggcgcccg   2820
ccactgcgcc ctactaattt tttgtatttt tagtagagac ggggtttcac cgtggtctcg   2880
atctcctgac ctcgtgatcc acccgcctca gcctcccaaa gtgctgggat tacaggcgtg   2940
agccactgcg cccggcccctt ttacatttat ttttaaatta agagacaggg tgtcactatg   3000
atgccgaggc tggtctcgaa ctcctgagct gaagtgatcc tcccacctcg gcctcccaaa   3060
atgctgggat taccatgtcc aactttccac ttcttgtttg accaaggatg gatggcagac   3120
```

```
atcagaaggg gcttggaaag ggaggtgtca aagaccttgc ccagcatgga gtctgggtca   3180
cagctggggg aggatctggg aactgtgctt gcctgaagct tacctgcttg tcatcaaatc   3240
caaggcaagg cgtgaatgtc tatagagtga gagacttgtg gagacagaag agcagagagg   3300
gaggaagaat gaacactggg tctgtttggg gctttcccag cttttgagtc agacaagatt   3360
tatttattta tttaagatgg agtctcattc tgttgcccag gctggagtgc agtggtgcca   3420
tcttggctca ctacagcctc cccacctccc aggttcaagt gcttctcctg cctcagcctc   3480
ccgagtagtt gggattacag gcgcccgcca ccacccag ctaattttg tatttcagt     3540 agagatgggg tttcgccatg ctggccaggc tgttctcgaa aactcctgac ctcagatgat   3600
ccacccgcct cggcctccca cagtgctggg attacaggcg tgagccactg cgctggccaa   3660
atcagacaag gtttaaatcc cagctctgcc tgtactagct gaggaactct gcacacattt   3720
cataaccttt ctgggcctac gttctcacct ttaacgtgag gataatatat ctacttcata   3780
gacacctttt tatgttgtct ccaagttttc taacagctct agttctgtac caagacatg    3840 gcaggtggcc aacgacatcc ttctaggctg tggtgatgtg tttggagctt gttccacggg   3900
tcttgtgtgg ggccagccct gttcagataa ggccttgtgg ggtggcctgg ggtaggggga   3960
ggggttgggc aaactctccc ttaaaacgct ttgtaaccat ctgaggcacc agcaagagcg   4020 gccccccgagc ctggacaaaa tccaaacggc ttcctacttc aagcactgat gtctagtgag  4080
tgaaggaaca gctctgggtc caggatatta taggtcacat taaactaaag gggcttggcc   4140
atcagctggc ttccagagcg tcagccagtt acttcacctc tttggctttg gcctgttttc   4200
agctacaaga ggacttaatc cagaggacct cagaggtcct tcccagctca gaccttcttt   4260
gactgtctcc cagagacact gctgtaggag tgcacaccag tttacttttc tttcttttgt   4320
ttttgagatg gagtttcgct cttttgcct aggctggagt gctgtggtgt gatctcagct    4380
cactgcaacc tctggctccc aggttcaagt gattctcctg tctctgcctc ccgagtagct   4440
gggattacag acacccacca ctgcacccgg ctagtttttg tattttcagt agagatgggg   4500
tttcgccatg ctggccaggc tgttctcgaa aactcctgac ctcagatgat ccatccgcct   4560
tggcctccca aagtgctgag attacagatg tgaggcacca cacccggcca ttttgtatt    4620 tttagtagag acggggtttt gccatgttgg ccacgctggt ctcaaactcc tgacctcaag   4680
tgatctgccc accttggcct cctgaagggc tgggactaca ggcgtgagtc accgtgcccg   4740
gccatttttg tattttagg acagcgtttt tcatgttgg ccaggctggt ctcaaactcc     4800
tgacctcaag tgatccaccc accccggcct cccaatatgc tgggattcca ggtgtgagtt   4860
accatgcccg gctaccactt tactttttcct gcaggctatc acagaacgtg tacaatctag   4920
actctaatca accaaatcaa cgtcttgcca tcggagtttg ctggtgaagg gcacttgggg   4980
tcctggaaat aactgtaggc tccaagccac acacactgag ataggcctat tccctgaggc   5040
ctcagagccc ctgacagcta agctcccttg agtcgggcaa ttttcaacaa cgtgctctgg   5100
ggacacagca tggcgccact gtctttctgg tctcctgggg ctcagactat gtcatacact   5160
tctttccagg gcagtgggta acaaagtttg actccagaaa gacttccctc gaggatttct   5220
acttggatga agagaggacc gtgagggtcc ccatgatgaa tc                      5262
```

<210> SEQ ID NO 6
<211> LENGTH: 4421
<212> TYPE: DNA
<213> ORGANISM: Homo sapiens

<400> SEQUENCE: 6

```
ggatcccttg gttggggtgt tggggaaggc agggttttaa cggaaatctc tctccatctc      60
tacagagctg caatccttgt ttgattcacc agactttagc aagatcacag gcaaacccat     120
caagctgact caggtggaac accgggctgg ctttgagtgg aacgaggatg gggcgggaac     180
caccccagc ccagggctgc agcctgccca cctcaccttc ccgctggact atcaccttaa      240
ccagcctttc atcttcgtac tgagggacac agacacaggg gcccttctct tcattggcaa     300
gattctggac cccaggggcc cctaatatcc cagtttaata ttccaatacc ctagaagaaa     360
acccgaggga cagcagattc cacaggacac gaaggctgcc cctgtaaggt ttcaatgcat     420
acaataaaag agctttatcc ctaacttctg ttacttcgtt cctcctccta ttttgagcta     480
tgcgaaatat catatgaaga gaaacagctc ttgaggaatt tggtggtcct ctacttctag     540
cctggtttta tctaaacact gcaggaagtc accgttcata agaactctta gttacctgtg     600
ttggataagg cacggacagc ttctctgctc tgggggtatt tctgtactag atcagtgat     660
cctcccggga ggccatttcc tgcccccata atcagggaag cctgctcgta aacaacacat     720
ggacagatag gagaggccat ttgtaactta aggaaacgga cccgatacgt aaagattctg     780
aacatattct ttgtaaggag gtatgcctat tttacaaagt acagccgggt gtggtggctc     840
atggctataa tcccagcact tgggaggcc gaggcgggcg atcacctga gatcaggagt       900
ttgagaccag cctgaccaac acggagaaac cccgtctgta ctaaaaatac aaaattagca    960
gggtgtggtg gtacatgcct gtaatcccag ctactgggga ggctgaggca ggagaatcac    1020
ttgaacccgg gaggcggagg ttgcagtgag ccgagatcac gccattgcac tccaatctag    1080
gcaataagag caaaactccg tctcaaacaa caaaaaacca agtataact gggcttttg      1140
aagaacatga aacatgccca gtgtctgaag tagaataact accgaactgt ccgtaggact    1200
aaactttttc ttgaaaaagc tctaccaaaa aaagtcaccg gccactccct tgtcacagtt    1260
attagacagg aggagaaatg ataattctac tgcccttcat tctacaaatg tttgagtgct    1320
aactgtattc cagattctca aaaagctatt gccaggtatc tctggggcta ctgatttcct    1380
gatcataatg caatggcaac caacaggcac ttgggcatgg tgagggtggg caagctttca    1440
aaagcagcgt ggatctggca ttctttttcca cgaatgcacc tcaactactt ggcaccagtg    1500
gtaacacagc aaccagggtt ccgacctaga gaatcccgta accttctgac tggaacgggg    1560
tctgggctgt cgctacacat cctggtggaa ggcagctatc atccctacct tctgccttct    1620
gtctcttaaa tctgaaccac aaacagcaac gtccataccc tcagcattgt tagaatcccc    1680
tgcagcctcc agttctcata ctgtctgtat tctactcgcc agtttggaga gtctggtgg    1740
agaaaaggag tctctttcca ggcttgacaa caaatagaac tcagggccgg gcgcggtggc    1800
tcacgcctgt catcccagca ctgtgggagg ccgaagcggg cggatcacct gaggtcggga    1860
gctcaagacc agcctggcca acatggagaa atcccatctt tactaaaaat acaaaattag    1920
ccgggcgtac tggcgaatgc ctgtaatgcc agcttctcgg gaggctgagg caggagaatc    1980
gcttgaacct gggaggcaga ggttgcggtg agccaagact gtgccactgt actccagcct    2040
tggtgacaga gggagactct gtcttaagaa aaaagaaaa aaaaaaaaa agggccgggc      2100
tcacgcctgt aatcccagca ctttgggagg ccaaatcacc tgaggccggg agtttgatac    2160
caacctgacc aacatagtga aatcccgtct ctactaaaaa tacaaaatta gccaggcgtg    2220
gtggcgggcg cctgtaatcc cagctactcg ggaggctgaa gcaggagaat cacttgaacc    2280
cggaaggcgg aggttgccgt aagccaagat cgcgccattg cgctccagcc tgggcaacaa    2340
```

| | | | | |
|---|---|---|---|---|
| gagtgaaact | ccatctcaaa | aacaaaacaa | aacaaaacaa | aaccaacaac tcagaaggag | 2400 |
| gcatatgtgt | tataaagtct | ttactacaac | tttgatttta | ttagtggttg gttactgact | 2460 |
| ctgccaagag | tacagaatga | agggcagaga | gtaaggactg | gaaaactggc aggaaacaca | 2520 |
| ctgacagccg | tcatccctgg | aggaaactgc | tcaataaaac | ggctccatat ttacttctct | 2580 |
| ggtcacagtt | catactccac | gattttaaca | aaggagtcga | ggaagctaga tactgtaagt | 2640 |
| ggaacggtgt | gtctctggag | gtaagcaggc | ttgctgattt | cttgttttat aattcttttt | 2700 |
| taattacaat | gtaactacta | agagcttcag | ttcccactgg | agtggtgcac acatctcatt | 2760 |
| actactaaaa | ccacaggaat | gttccaggga | aacagactat | catcactgag cgaggtggaa | 2820 |
| tccagccaaa | accccaggct | aacatccaga | tgcctgcata | tcagctaaaa tccttttaaa | 2880 |
| ggacttggaa | tctccagata | ctagttttaa | gtcttttctg | ggaactggga gtttgtactg | 2940 |
| gaggccactt | aactatttca | aaaaatattc | accaaaatag | gtgtctctct gactgcaacg | 3000 |
| gtttgagtcc | tcctcagccc | tcatatccta | ggcttcggac | tgttgggaaa gtcttatctt | 3060 |
| cctgacgaaa | gctcagcagc | aacagaacct | gttatttttt | tgttgagaca gggtcttact | 3120 |
| ctgtcaccca | ggctggagtg | cagtagtgcg | atcttggctc | actgcagcct cagcctacca | 3180 |
| ggctcaggtg | accctatctc | agcttctcga | gtaggtggga | ctacaggcat gtgccaccat | 3240 |
| gctcggtgaa | ctaaacaaac | ttttttgtag | tgatacggtc | tcactatatt gcccaggctg | 3300 |
| gttttgaact | cctgggctca | agtgatcctc | ccacctcagc | gtctcaaagt actgggatta | 3360 |
| caggtgtgag | cctctacact | gggcctgcag | aacctacaca | gaatccgcac ctggtctgca | 3420 |
| gaacccacac | ccgacccaca | gaacccacac | ccgacccaca | gaacccacat ctggcagcag | 3480 |
| aacctcttag | tatttttttt | ttttctttga | gatggagtct | ggctctgtca cccaggctgg | 3540 |
| agtgcagtgg | cgcgatctcg | gctcactgca | agctcttcct | cccgggttca ccccattctc | 3600 |
| ctgcctcaac | ctcccgagta | gctgtgaata | caggcgtccg | ccaccacgcc cgactaattt | 3660 |
| ttttgtattt | ttagtagaga | cggggtttca | ccgtgttagc | caggatggtc tggatctcct | 3720 |
| gacctcgtga | tctgcctgcc | tcggcctccc | aaagtgctgg | gattacaggc ttgagccacc | 3780 |
| gcacccggcc | tcttattttt | tttttgaga | tggagtctca | cactgtcacc tgggctggag | 3840 |
| tgcagtggag | cgatctcggc | tcactgcaac | ctccgcctcc | tgggttcaag agattctcct | 3900 |
| gcctcagcct | cccaagtagc | tgggattaca | ggtgcccacc | accacgcctg gctagttttt | 3960 |
| tgtatttta | gtaaagatgg | ggtttcacca | tgttggccag | gctggtcttg aactcctgac | 4020 |
| atcaggtgat | ccgcccacct | tagcctccca | aagtgctggg | attacaggcg tgagccacca | 4080 |
| tacctggcca | gcaaaacctc | tttaacttgt | gttccatggg | ctccttttct gtgggtcaaa | 4140 |
| atcctcctgg | aaccctacaa | tgcaggccct | acagggtgg | gtggtaagtc caacaaacag | 4200 |
| gatttcatct | tctggagctc | ctggatttca | tcgtcccatg | ggccacagtg cagcgacaga | 4260 |
| acctcctcag | ctttctgtat | tgtgctcagg | gcttcgggta | ctgcaaacct gagccaaggg | 4320 |
| aggtaagagg | agttagttca | ctgattcgtg | aggcaaatgt | taattgaggg cctactcaca | 4380 |
| caccgtgaag | aatgtaagat | catttctgtc | atcaaggatc | c | 4421 |

<210> SEQ ID NO 7
<211> LENGTH: 1153
<212> TYPE: DNA
<213> ORGANISM: Mus musculus

<400> SEQUENCE: 7

| | | | | |
|---|---|---|---|---|
| ggagctgccg | caaccacagt | tccgggatgc | aggccctggt | gctactcctc tggactggag | 60 |

| | |
|---|---:|
| ccctcctggg gcacggcagc agccagaacg tccccagcag ctctgagggc tccccagtcc | 120 |
| cggacagcac gggcgagccc gtggaggagg aggacccctt cttcaaggtc cctgtgaaca | 180 |
| agctggcagc agctgtctcc aacttcggct acgatctgta ccgcctgaga tccggtgcca | 240 |
| gcccaacggg caacgtcctg ctgtctccac tcagcgtggc cacggccctc tcggccctct | 300 |
| ctcttggagc tgaacatcga acagagtctg tcattcaccg ggctctctac tacgacctga | 360 |
| tcaccaaccc tgacatccat agcacctaca aggcgctcct tgcctctgtt actgcccctg | 420 |
| agaagaacct caagagtgct tccagaattg tgtttgagag gaaacttcga gtcaaatcca | 480 |
| gctttgttgc ccctctggag aagtcctatg ggaccaggcc ccggatcctc acgggcaacc | 540 |
| ctcgagtaga ccttcaggag attaacaact gggtgcaggc ccagatgaaa gggaagattg | 600 |
| cccggtccac gagggaaatg cccagtgccc tcagcatcct tctccttggc gtggcttact | 660 |
| tcaaggggca gtgggtaacc aagtttgact cgagaaagac caccctccag gattttcatt | 720 |
| tggacgagga caggaccgtg agagtcccca tgatgtcaga tcctaaggcc atcttacgat | 780 |
| acggcttgga ctctgatctc aactgcaaga ttgcccagct gcccttgaca ggaagtatga | 840 |
| gcatcatctt cttcctgccc ctgaccgtga cccagaactt gaccatgata aagagagcc | 900 |
| tcacctctga gttcattcat gacatcgacc gagaactgaa gactatccaa gctgtgctga | 960 |
| ctgtccccaa gcttgaagctg agcttcgaag gcgaacttac caagtctctg caggacatga | 1020 |
| agctacagtc gttgtttgaa tcacccgact tcagcaagat tactggcaaa cccgtgaagc | 1080 |
| tcacccaagt ggaacacagg gctgctttcg agtggaatga agaggggca ggaagcagcc | 1140 |
| ccagcccagg cct | 1153 |

<210> SEQ ID NO 8
<211> LENGTH: 1490
<212> TYPE: DNA
<213> ORGANISM: Homo sapiens

<400> SEQUENCE: 8

| | |
|---|---:|
| ggacgctgga ttagaaggca gcaaaaaaag atctgtgctg gctggagccc cctcagtgtg | 60 |
| caggcttaga gggactaggc tgggtgtgga gctgcagcgt atccacaggc cccaggatgc | 120 |
| aggccctggt gctactcctc tgcattggag ccctcctcgg gcacagcagc tgccagaacc | 180 |
| ctgccagccc cccggaggag ggctccccag accccgacag cacaggggcg ctggtggagg | 240 |
| aggaggatcc tttcttcaaa gtccccgtga caagctggc agcggctgtc tccaacttcg | 300 |
| gctatgacct gtaccgggtg cgatccagca cgagcccac gaccaacgtg ctcctgtctc | 360 |
| ctctcagtgt ggccacggcg ctctcggccc tctcgctggg agcggagcag cgaacagaat | 420 |
| ccatcattca ccgggctctc tactatgact tgatcagcag cccagacatc catggtacct | 480 |
| ataaggagct ccttgacacg gtcactgccc ccagaagaa cctcaagagt gcctcccgga | 540 |
| tcgtctttga aagaagctac gcataaaaat ccagctttgt ggcacctctg aaaagtcat | 600 |
| atgggaccag gccagagtc ctgacgggca accctcgctt ggacctgcaa gagatcaaca | 660 |
| actgggtgca ggcgcagatg aaagggaagc tcgccaggtc cacaaaggaa attcccgatg | 720 |
| agatcagcat tctccttctc ggtgtggcgc acttcaaggg gcagtgggta acaaagtttg | 780 |
| actccagaaa gacttccctc gaggatttct acttggatga agagaggacc gtgagggtcc | 840 |
| ccatgatgtc ggaccctaag gctgttttac gctatggctt ggattcagat ctcagctgca | 900 |
| agattgccca gctgcccttg accggaagca tgagtatcat cttcttcctg cccctgaaag | 960 |

```
tgacccagaa tttgaccttg atagaggaga gcctcacctc cgagttcatt catgacatag    1020
accgagaact gaagaccgtg caggcggtcc tcactgtccc caagctgaag ctgagttacg    1080
aaggcgaagt caccaagtcc ctgcaggaga tgaagctgca atccttgttt gattcaccag    1140
actttagcaa gatcacaggc aaacccatca agctgactca ggtggaacac cgggctggct    1200
ttgagtggaa cgaggatggg gcgggaacca cccccagccc agggctgcag cctgcccacc    1260
tcaccttccc gctggactat caccttaacc agcctttcat cttcgtactg agggacacag    1320
acacaggggc ccttctcttc attggcaaga ttctggaccc caggggcccc taatatccca    1380
gtttaatatt ccaatacccct agaagaaaac ccgagggaca gcagattcca caggacacga    1440
aggctgcccc tgtaaggttt caatgcatac aataaaagag ctttatccct              1490
```

<210> SEQ ID NO 9
<211> LENGTH: 20
<212> TYPE: DNA
<213> ORGANISM: Artificial
<220> FEATURE:
<223> OTHER INFORMATION: Primer

<400> SEQUENCE: 9
acaagctggc agcggctgtc                                               20

<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10
cagaggtgcc acaaagctgg                                               20

<210> SEQ ID NO 11
<211> LENGTH: 20
<212> TYPE: DNA
<213> ORGANISM: Artificial
<220> FEATURE:
<223> OTHER INFORMATION: Primer

<400> SEQUENCE: 11
ccagctttgt ggcacctctg                                               20

<210> SEQ ID NO 12
<211> LENGTH: 20
<212> TYPE: DNA
<213> ORGANISM: Artificial
<220> FEATURE:
<223> OTHER INFORMATION: Primer

<400> SEQUENCE: 12
catcatgggg accctcacgg                                               20

<210> SEQ ID NO 13
<211> LENGTH: 20
<212> TYPE: DNA
<213> ORGANISM: Artificial
<220> FEATURE:
<223> OTHER INFORMATION: Primer

<400> SEQUENCE: 13
aggatgcagg ccctggtgct                                               20

```
<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14
cctcctccac cagcgcccct                                                        20

<210> SEQ ID NO 15
<211> LENGTH: 21
<212> TYPE: DNA
<213> ORGANISM: Artificial
<220> FEATURE:
<223> OTHER INFORMATION: Primer

<400> SEQUENCE: 15
atgtcggacc ctaaggctgt t                                                      21

<210> SEQ ID NO 16
<211> LENGTH: 20
<212> TYPE: DNA
<213> ORGANISM: Artificial
<220> FEATURE:
<223> OTHER INFORMATION: Primer

<400> SEQUENCE: 16
tggggacagt gaggaccgcc                                                        20

<210> SEQ ID NO 17
<211> LENGTH: 20
<212> TYPE: DNA
<213> ORGANISM: Artificial
<220> FEATURE:
<223> OTHER INFORMATION: Primer

<400> SEQUENCE: 17
ggtgtgcaaa tgtgtgcgcc                                                        20

<210> SEQ ID NO 18
<211> LENGTH: 24
<212> TYPE: DNA
<213> ORGANISM: Artificial
<220> FEATURE:
<223> OTHER INFORMATION: Primer

<400> SEQUENCE: 18
gggagctgct ttacctgtgg atac                                                   24

<210> SEQ ID NO 19
<211> LENGTH: 25
<212> TYPE: DNA
<213> ORGANISM: Artificial
<220> FEATURE:
<223> OTHER INFORMATION: Primer

<400> SEQUENCE: 19
ggacgctgga ttagaaggca gcaaa                                                  25

<210> SEQ ID NO 20
<211> LENGTH: 19
<212> TYPE: DNA
<213> ORGANISM: Artificial
<220> FEATURE:
<223> OTHER INFORMATION: Primer
```

-continued

```
<400> SEQUENCE: 20
ccacacccag cctagtccc                                                  19

<210> SEQ ID NO 21
<211> LENGTH: 19
<212> TYPE: PRT
<213> ORGANISM: Artificial
<220> FEATURE:
<223> OTHER INFORMATION: Synthetic Construct

<400> SEQUENCE: 21

Thr Ser Leu Glu Asp Phe Tyr Leu Asp Glu Glu Arg Thr Val Arg Val
1               5                   10                  15

Pro Met Met

<210> SEQ ID NO 22
<211> LENGTH: 26
<212> TYPE: PRT
<213> ORGANISM: Artificial
<220> FEATURE:
<223> OTHER INFORMATION: Synthetic Construct

<400> SEQUENCE: 22

Ser Tyr Gly Thr Arg Pro Arg Val Leu Thr Gly Asn Pro Arg Leu Asp
1               5                   10                  15

Leu Gln Glu Ile Asn Asn Trp Val Gln Ala
            20                  25

<210> SEQ ID NO 23
<211> LENGTH: 14
<212> TYPE: PRT
<213> ORGANISM: Artificial
<220> FEATURE:
<223> OTHER INFORMATION: Synthetic Construct

<400> SEQUENCE: 23

Leu Ala Ala Ala Val Ser Asn Phe Gly Tyr Asp Leu Tyr Arg
1               5                   10

<210> SEQ ID NO 24
<211> LENGTH: 29
<212> TYPE: PRT
<213> ORGANISM: Artificial
<220> FEATURE:
<223> OTHER INFORMATION: Synthetic Construct

<400> SEQUENCE: 24

Ala Leu Tyr Tyr Asp Leu Ile Ser Ser Pro Asp Ile His Gly Thr Tyr
1               5                   10                  15

Lys Glu Leu Leu Asp Thr Val Thr Ala Pro Gln Lys Asn
            20                  25

<210> SEQ ID NO 25
<211> LENGTH: 10
<212> TYPE: PRT
<213> ORGANISM: Artificial
<220> FEATURE:
<223> OTHER INFORMATION: Synthetic Construct

<400> SEQUENCE: 25

Thr Val Gln Ala Val Leu Thr Val Pro Lys
1               5                   10

<210> SEQ ID NO 26
```

```
<211> LENGTH: 11
<212> TYPE: PRT
<213> ORGANISM: Artificial
<220> FEATURE:
<223> OTHER INFORMATION: Synthetic Construct

<400> SEQUENCE: 26

Leu Lys Leu Ser Tyr Glu Gly Glu Val Thr Lys
1               5                   10

<210> SEQ ID NO 27
<211> LENGTH: 30
<212> TYPE: PRT
<213> ORGANISM: Artificial
<220> FEATURE:
<223> OTHER INFORMATION: Synthetic Construct

<400> SEQUENCE: 27

Ala Gly Phe Glu Trp Asn Glu Asp Gly Ala Gly Thr Thr Pro Ser Pro
1               5                   10                  15

Gly Leu Gln Pro Ala His Leu Thr Phe Pro Leu Asp Tyr His
            20                  25                  30

<210> SEQ ID NO 28
<211> LENGTH: 20
<212> TYPE: DNA
<213> ORGANISM: Artificial
<220> FEATURE:
<223> OTHER INFORMATION: Oligonucleotide

<400> SEQUENCE: 28
agyaayttyt aygayctsta                                               20

<210> SEQ ID NO 29
<211> LENGTH: 20
<212> TYPE: DNA
<213> ORGANISM: Artificial
<220> FEATURE:
<223> OTHER INFORMATION: Oligonucleotide

<400> SEQUENCE: 29
ctytcytcrt csagrtaraa                                               20

<210> SEQ ID NO 30
<211> LENGTH: 20
<212> TYPE: DNA
<213> ORGANISM: Artificial
<220> FEATURE:
<223> OTHER INFORMATION: Primer

<400> SEQUENCE: 30
ctgggagcgg acgagcgaac                                               20

<210> SEQ ID NO 31
<211> LENGTH: 20
<212> TYPE: DNA
<213> ORGANISM: Artificial
<220> FEATURE:
<223> OTHER INFORMATION: Primer

<400> SEQUENCE: 31
caccttaacc agcctttatt                                               20

<210> SEQ ID NO 32
<211> LENGTH: 20
<212> TYPE: DNA
```

<210> SEQ ID NO 32
<211> LENGTH: 20
<212> TYPE: DNA
<213> ORGANISM: Artificial
<220> FEATURE:
<223> OTHER INFORMATION: Primer

<400> SEQUENCE: 32
aaccttacag gggcagcctt                                          20

<210> SEQ ID NO 33
<211> LENGTH: 24
<212> TYPE: DNA
<213> ORGANISM: Artificial
<220> FEATURE:
<223> OTHER INFORMATION: Primer

<400> SEQUENCE: 33
tatcccagtt taatattcca atac                                     24

<210> SEQ ID NO 34
<211> LENGTH: 24
<212> TYPE: DNA
<213> ORGANISM: Artificial
<220> FEATURE:
<223> OTHER INFORMATION: Primer

<400> SEQUENCE: 34
ttgtatgcat tgaaaccttacagg                                      24

<210> SEQ ID NO 35
<211> LENGTH: 20
<212> TYPE: DNA
<213> ORGANISM: Artificial
<220> FEATURE:
<223> OTHER INFORMATION: Primer

<400> SEQUENCE: 35
tggggacagt gaggaccgcc                                          20

<210> SEQ ID NO 36
<211> LENGTH: 20
<212> TYPE: DNA
<213> ORGANISM: Artificial
<220> FEATURE:
<223> OTHER INFORMATION: Primer

<400> SEQUENCE: 36
acaagctggc agcggctgtc                                          20

<210> SEQ ID NO 37
<211> LENGTH: 20
<212> TYPE: DNA
<213> ORGANISM: Artificial
<220> FEATURE:
<223> OTHER INFORMATION: Primer

<400> SEQUENCE: 37
cagaggtgcc acaaagctgg                                          20

<210> SEQ ID NO 38
<211> LENGTH: 20
<212> TYPE: DNA
<213> ORGANISM: Artificial
<220> FEATURE:
<223> OTHER INFORMATION: Primer

<400> SEQUENCE: 38
ccagctttgt ggcacctctg                                          20

<210> SEQ ID NO 39
<211> LENGTH: 20
<212> TYPE: DNA
<213> ORGANISM: Artificial
<220> FEATURE:
<223> OTHER INFORMATION: Primer

<400> SEQUENCE: 39
catcatgggg accctcacgg                                              20

<210> SEQ ID NO 40
<211> LENGTH: 20
<212> TYPE: DNA
<213> ORGANISM: Artificial
<220> FEATURE:
<223> OTHER INFORMATION: Primer

<400> SEQUENCE: 40
aggatgcagg ccctggtgct                                              20

<210> SEQ ID NO 41
<211> LENGTH: 20
<212> TYPE: DNA
<213> ORGANISM: Artificial
<220> FEATURE:
<223> OTHER INFORMATION: Primer

<400> SEQUENCE: 41
cctcctccac cagcgcccct                                              20

<210> SEQ ID NO 42
<211> LENGTH: 20
<212> TYPE: DNA
<213> ORGANISM: Artificial
<220> FEATURE:
<223> OTHER INFORMATION: Primer

<400> SEQUENCE: 42
atgtcggacc ctaaggctgt                                              20

<210> SEQ ID NO 43
<211> LENGTH: 20
<212> TYPE: DNA
<213> ORGANISM: Artificial
<220> FEATURE:
<223> OTHER INFORMATION: Primer

<400> SEQUENCE: 43
tggggacagt gaggaccgcc                                              20

<210> SEQ ID NO 44
<211> LENGTH: 24
<212> TYPE: DNA
<213> ORGANISM: Artificial
<220> FEATURE:
<223> OTHER INFORMATION: Primer

<400> SEQUENCE: 44
ggtgtgcaaa tgtgtgcgcc ttag                                         24

<210> SEQ ID NO 45
<211> LENGTH: 24
<212> TYPE: DNA
<213> ORGANISM: Artificial
<220> FEATURE:

```
<223> OTHER INFORMATION: Primer

<400> SEQUENCE: 45
gggagctgct ttacctgtgg atac                                              24

<210> SEQ ID NO 46
<211> LENGTH: 25
<212> TYPE: DNA
<213> ORGANISM: Artificial
<220> FEATURE:
<223> OTHER INFORMATION: Primer

<400> SEQUENCE: 46
ggacgctgga ttagaaggca gcaaa                                             25

<210> SEQ ID NO 47
<211> LENGTH: 19
<212> TYPE: DNA
<213> ORGANISM: Artificial
<220> FEATURE:
<223> OTHER INFORMATION: Primer

<400> SEQUENCE: 47
ccacacccag cctagtccc                                                    19

<210> SEQ ID NO 48
<211> LENGTH: 4
<212> TYPE: PRT
<213> ORGANISM: Artificial
<220> FEATURE:
<223> OTHER INFORMATION: Synthetic Construct

<400> SEQUENCE: 48

Met Asn Arg Ile
1
```